(12) United States Patent
Butler et al.

(10) Patent No.: US 12,193,948 B2
(45) Date of Patent: Jan. 14, 2025

(54) EXPANDABLE IMPLANT ASSEMBLY

(71) Applicant: Life Spine, Inc., Huntley, IL (US)

(72) Inventors: Michael S. Butler, St. Charles, IL (US); Madeline Wolters, Carol Stream, IL (US); Daniel Predick, West Lafayette, IN (US); Garrett D. Lauf, Elgin, IL (US); Katrina Robin Keller, Saint Charles, IL (US)

(73) Assignee: Life Spine, Inc., Huntley, IL (US)

(*) Notice: Subject to any disclaimer, the term of this patent is extended or adjusted under 35 U.S.C. 154(b) by 1125 days.

(21) Appl. No.: 16/904,248

(22) Filed: Jun. 17, 2020

(65) Prior Publication Data

US 2020/0383798 A1 Dec. 10, 2020

Related U.S. Application Data

(63) Continuation-in-part of application No. 16/548,134, filed on Aug. 22, 2019, now Pat. No. 11,103,362, (Continued)

(51) Int. Cl.
*A61F 2/44* (2006.01)
*A61F 2/30* (2006.01)

(52) U.S. Cl.
CPC .............. *A61F 2/447* (2013.01); *A61F 2/446* (2013.01); *A61F 2002/3037* (2013.01); (Continued)

(58) Field of Classification Search
CPC ...... A61B 17/8805; A61F 2/4601; A61F 2/44; A61F 2/442; A61F 2/4455
See application file for complete search history.

(56) References Cited

U.S. PATENT DOCUMENTS 856,481 A 6/1907 Losie, Jr.
904,434 A 11/1908 Co
(Continued)

FOREIGN PATENT DOCUMENTS

CN 102427769 A 4/2012
CN 205866898 U 1/2017
(Continued)

OTHER PUBLICATIONS

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.
(Continued)

*Primary Examiner* — David W Bates
(74) *Attorney, Agent, or Firm* — Foley & Lardner LLP

(57) ABSTRACT

An expandable implant includes an upper portion configured to engage a first portion of bone, a bottom portion configured to engage a second portion of bone, a control assembly coupled to the upper portion and the bottom portion and configured to control relative movement between the upper portion and the bottom portion, wherein the control assembly includes a front portion and a control member, wherein the front portion has an aperture configured to receive the control member, wherein the control member includes a head, and wherein a portion of the head is positioned outside of the aperture as the implant is expanded between a first, collapsed orientation and a second, expanded orientation.

20 Claims, 61 Drawing Sheets

Related U.S. Application Data which is a continuation of application No. 15/497,044, filed on Apr. 25, 2017, now Pat. No. 10,426,632, which is a continuation-in-part of application No. 14/714,821, filed on May 18, 2015, now Pat. No. 9,801,733, which is a continuation-in-part of application No. 13/802,110, filed on Mar. 13, 2013, now Pat. No. 9,034,041.

(52) U.S. Cl.
CPC ............ *A61F 2002/30387* (2013.01); *A61F 2002/30405* (2013.01); *A61F 2002/30428* (2013.01); *A61F 2002/30433* (2013.01); *A61F 2002/30471* (2013.01); *A61F 2002/30507* (2013.01); *A61F 2002/30515* (2013.01); *A61F 2002/30538* (2013.01); *A61F 2002/30556* (2013.01); *A61F 2002/30579* (2013.01); *A61F 2002/30784* (2013.01); *A61F 2002/30841* (2013.01); *A61F 2002/30904* (2013.01); *A61F 2310/00017* (2013.01); *A61F 2310/00023* (2013.01)

(56) References Cited

U.S. PATENT DOCUMENTS

| | | |
|---|---|---|
| 1,925,385 A | 9/1933 | Humes |
| 4,466,426 A | 8/1984 | Blackman |
| 4,636,217 A | 1/1987 | Ogilvie et al. |
| 4,743,256 A | 5/1988 | Brantigan |
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,129,763 A | 10/2000 | Chauvin et al. |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,302,914 B1 | 10/2001 | Michelson |
| 6,375,682 B1 | 4/2002 | Fleischmann et al. |
| 6,409,766 B1 | 6/2002 | Brett |
| 6,443,989 B1 | 9/2002 | Jackson |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 6,800,092 B1 | 10/2004 | Williams et al. |
| 6,849,093 B2 | 2/2005 | Michelson |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 | 1/2009 | Aebi et al. |
| 7,503,933 B2 | 3/2009 | Michelson |
| 7,621,950 B1 | 11/2009 | Globerman et al. |
| 7,695,513 B2 | 4/2010 | Zucherman et al. |
| 7,722,674 B1 | 5/2010 | Grotz |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,850,733 B2 | 12/2010 | Baynham et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,070,817 B2 | 12/2011 | Gradl et al. |
| 8,071,007 B1 | 12/2011 | Teoh et al. |
| 8,105,382 B2 | 1/2012 | Olmos et al. |
| 8,187,332 B2 | 5/2012 | McLuen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Morgenstern Lopez |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,523,944 B2 | 9/2013 | Jimenez et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | McLuen et al. |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,663,332 B1 | 3/2014 | To et al. |
| 8,679,183 B2 | 3/2014 | Glerum et al. |
| 8,685,098 B2 | 4/2014 | Glerum et al. |
| 8,690,883 B2 | 4/2014 | Collins et al. |

(56) References Cited

U.S. PATENT DOCUMENTS

| | | |
|---|---|---|
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |
| 9,149,367 B2 | 10/2015 | Davenport et al. |
| 9,186,258 B2 | 11/2015 | Davenport et al. |
| 9,186,262 B2 | 11/2015 | McLuen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,333,092 B2 | 5/2016 | To et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | McLaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | McAtamney et al. |
| 9,532,821 B2 | 1/2017 | Moskowitz et al. |
| 9,532,883 B2 | 1/2017 | McLuen et al. |
| 9,539,103 B2 | 1/2017 | McLaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | McLuen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | McLuen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | McLaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | McLuen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 | 11/2018 | Dewey et al. |
| 10,143,500 B2 | 12/2018 | Niemiec et al. |
| 10,143,569 B2 | 12/2018 | Weiman et al. |
| 10,154,911 B2 | 12/2018 | Predick et al. |
| 10,159,583 B2 | 12/2018 | Dietzel et al. |
| 10,195,050 B2 | 2/2019 | Palmatier et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | McLuen et al. |
| 10,299,934 B2 | 5/2019 | Seifert et al. |

(56) References Cited

U.S. PATENT DOCUMENTS

| | | |
|---|---|---|
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | McLuen et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,573 B2 | 7/2020 | Weiman et al. |
| 10,709,574 B2 | 7/2020 | McLuen et al. |
| 10,722,379 B2 | 7/2020 | McLaughlin et al. |
| 10,729,560 B2 | 8/2020 | Baker et al. |
| 10,729,562 B2 | 8/2020 | Knapp et al. |
| 10,736,754 B2 | 8/2020 | McLuen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 | 6/2021 | Miller et al. |
| 11,051,951 B2 | 7/2021 | Robinson et al. |
| 11,065,128 B2 | 7/2021 | Zappacosta et al. |
| 11,083,584 B2 | 8/2021 | Lauf et al. |
| 11,304,817 B2 | 4/2022 | Altarac et al. |
| 11,304,818 B2 | 4/2022 | Butler et al. |
| 2002/0010472 A1 | 1/2002 | Kuslich et al. |
| 2002/0029084 A1 | 3/2002 | Paul et al. |
| 2002/0091447 A1 | 7/2002 | Shimp et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2002/0147461 A1 | 10/2002 | Aldrich et al. |
| 2002/0177897 A1 | 11/2002 | Michelson |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm, Jr. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0230309 A1 | 11/2004 | Dimauro et al. |
| 2004/0254643 A1 | 12/2004 | Jackson |
| 2005/0027362 A1 | 2/2005 | Williams et al. |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0122701 A1 | 6/2006 | Kiester |
| 2006/0189999 A1 | 8/2006 | Zwirkoski |
| 2006/0241601 A1 | 10/2006 | Trautwein et al. |
| 2006/0241621 A1 | 10/2006 | Moskowitz et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0213739 A1 | 9/2007 | Michelson |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0119853 A1 | 5/2008 | Felt et al. |
| 2008/0119945 A1 | 5/2008 | Frigg |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0243251 A1 | 10/2008 | Stad et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062833 A1 | 3/2009 | Song |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198338 A1 | 8/2009 | Phan |
| 2009/0198339 A1 | 8/2009 | Kleiner et al. |
| 2009/0222099 A1 | 9/2009 | Liu et al. |
| 2009/0222100 A1 | 9/2009 | Cipoletti et al. |
| 2009/0228109 A1 | 9/2009 | Pointillant et al. |
| 2009/0312837 A1 | 12/2009 | Eisermann et al. |
| 2010/0082109 A1 | 4/2010 | Greenhalgh et al. |
| 2010/0103344 A1 | 4/2010 | Wang et al. |
| 2010/0179655 A1 | 7/2010 | Hansell et al. |
| 2010/0185291 A1 | 7/2010 | Jimenez et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234889 A1 | 9/2010 | Hess |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0029085 A1 | 2/2011 | Hynes et al. |
| 2011/0046682 A1 | 2/2011 | Stephan et al. |
| 2011/0054538 A1 | 3/2011 | Zehavi et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144753 A1 | 6/2011 | Marchek et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172716 A1 | 7/2011 | Glerum |
| 2011/0172774 A1 | 7/2011 | Varela |
| 2011/0178599 A1 | 7/2011 | Brett |
| 2011/0184468 A1 | 7/2011 | Metcalf et al. |
| 2011/0190817 A1 | 8/2011 | Thommen et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |

(56) References Cited

U.S. PATENT DOCUMENTS

| | | |
|---|---|---|
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0059475 A1* | 3/2012 | Weiman .................. A61F 2/44 |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0203347 A1 | 8/2012 | Glerum et al. |
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0144391 A1 | 6/2013 | Siegal et al. |
| 2013/0158663 A1 | 6/2013 | Miller et al. |
| 2013/0158664 A1 | 6/2013 | Palmatier et al. |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 | 11/2014 | Suddaby et al. |
| 2015/0012097 A1 | 1/2015 | Ibarra et al. |
| 2015/0066145 A1 | 3/2015 | Rogers et al. |
| 2015/0100128 A1 | 4/2015 | Glerum et al. |
| 2015/0100130 A1 | 4/2015 | Perrow |
| 2015/0112438 A1 | 4/2015 | McLean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0095718 A1 | 4/2016 | Weiman et al. |
| 2016/0113776 A1 | 4/2016 | Capote |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 | 12/2016 | Faulhaber |
| 2016/0374826 A1 | 12/2016 | Palmatier et al. |
| 2017/0014244 A1 | 1/2017 | Seifert et al. |
| 2017/0056197 A1 | 3/2017 | Weiman et al. |
| 2017/0100255 A1 | 4/2017 | Hleihil et al. |
| 2017/0172756 A1 | 6/2017 | Faulhaber |
| 2017/0216036 A1 | 8/2017 | Cordaro |
| 2017/0224504 A1 | 8/2017 | Butler et al. |
| 2017/0224505 A1 | 8/2017 | Butler et al. |
| 2017/0246006 A1 | 8/2017 | Carnes et al. |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0000609 A1 | 1/2018 | Hessler et al. |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0185163 A1 | 7/2018 | Weiman et al. |
| 2018/0243107 A1 | 8/2018 | Foley et al. |
| 2018/0256359 A1 | 9/2018 | Greenhalgh |
| 2018/0296361 A1 | 10/2018 | Butler et al. |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360616 A1 | 12/2018 | Luu |
| 2019/0021871 A1 | 1/2019 | Baynham |
| 2019/0133779 A1 | 5/2019 | McLaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0129307 A1 | 4/2020 | Hunziker et al. |
| 2020/0360153 A1 | 11/2020 | Weiman et al. |
| 2021/0045891 A1 | 2/2021 | Rogers et al. |
| 2021/0045892 A1 | 2/2021 | Rogers et al. |
| 2021/0077274 A1 | 3/2021 | Robie |
| 2021/0113349 A1 | 4/2021 | Weiman et al. |
| 2021/0137699 A1 | 5/2021 | Jang et al. |
| 2021/0259849 A1 | 8/2021 | Robinson et al. |
| 2021/0322181 A1 | 10/2021 | Predick |
| 2021/0353428 A1 | 11/2021 | Predick et al. |
| 2022/0133495 A1 | 5/2022 | Glerum et al. |
| 2022/0304823 A1 | 9/2022 | Melchor |
| 2022/0387184 A1 | 12/2022 | Josse et al. |

FOREIGN PATENT DOCUMENTS

| | | |
|---|---|---|
| DE | 94 07 806 U1 | 7/1994 |
| DE | 20314708 U1 | 11/2003 |
| DE | 10 2020 200 882 A1 | 7/2020 |
| EP | 0 880 950 A1 | 12/1998 |
| EP | 1 925 272 A1 | 5/2008 |
| EP | 2 777 633 A2 | 9/2014 |
| EP | 3 031 424 A1 | 6/2016 |
| EP | 3 245 982 | 11/2017 |
| EP | 3 366 263 A1 | 8/2018 |
| EP | 3 479 799 A1 | 5/2019 |
| EP | 3 769 725 A1 | 1/2021 |
| FR | 2717068 A1 | 4/1996 |
| FR | 2727003 B1 | 4/1997 |
| FR | 2894130 A1 | 6/2007 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 | 6/2004 |
| WO | WO-2005/009299 A1 | 2/2005 |
| WO | WO-2006/102485 | 9/2006 |
| WO | WO-2006/105437 A2 | 10/2006 |
| WO | WO-2009/124269 A1 | 10/2009 |
| WO | WO-2010/148112 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-2016/051095 A1 | 4/2016 |
| WO | WO-2016/077610 A1 | 5/2016 |
| WO | WO-2016/127139 A1 | 8/2016 |
| WO | WO-2017/027277 A1 | 2/2017 |

(56) References Cited

FOREIGN PATENT DOCUMENTS

| WO | WO-2017/027873 A1 | 2/2017 |
|---|---|---|
| WO | WO-2017/066463 A1 | 4/2017 |
| WO | WO-2017/106614 A1 | 6/2017 |
| WO | WO-2018/049227 A1 | 3/2018 |
| WO | WO-2018/200507 A1 | 11/2018 |
| WO | WO-2018/200530 A1 | 11/2018 |
| WO | WO2019/0014139 A1 | 1/2019 |
| WO | WO-2019/014139 A1 | 1/2019 |
| WO | WO-2019/126213 A1 | 6/2019 |
| WO | WO-2019/241687 A1 | 12/2019 |
| WO | WO-2021/030645 A1 | 2/2021 |

OTHER PUBLICATIONS

Schizas, C., "Spinal Fusion: Techniques Results and Limitations." European Cells and Materials. 2005, vol. 10, Suppl. 3, p. 1.
"MectaLIF Oblique & Posterior Intervertebral Body Fusion Device." Brochure. 2004, Medacta International, San Pietro, Switzerland.
"Wedge." Encyclopedia Brittanica. Aug. 14, 2008. britannica.com/print/article/638734.
Kambin, P., et al., "Arthroscopic Discectomy of the Lumbar Spine." Clinical Orthopaedics and Related Research. Apr. 1997, No. 337, pp. 49-57.
Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.
Kim, Y, et al., "Clinical Applications of the Tubular Retractor on Spinal Disorders." Journal of Korean Neurosurgery, Nov. 2007, No. 42, pp. 244-250.
Moore, J., et al, "Mechanics Map—Wedges." Aug. 20, 2022, mechanicsmap.psu.edu/websites/7_friction/7-3_wedges/wedges.
Peltier, L. "Orthopedics: A History and Iconography" 1993, Norman Publishing, San Francisco, CA.
Sasso, R., et al., "Anterior Lumbar Interbody Fusion." Surgical Management of Low Back Pain. 2009, Chapter 10, pp. 87-95.
Tsuang, Y., et al., "Comparison of cage application modality in posterior lumbar interbody fusion with posterior instrumentation—A finite element study." Medical Engineering & Physics 31. 2009, pp. 565-570.
Virk, S., et al. "History of Spinal Fusion: Where We Came from and Where We Are Going." Current Concepts in Spinal Fusion. HSS Journal, 2020, No. 16, pp. 137-142.
Xiao, Y, et al., "Unilateral Transforaminal Lumbar Interbody Fusion: a Review of the Technique, Indications and Graft Materials." The Journal of International Medical Research. 2009, No. 37, pp. 908-917.
International Search Report and Written Opinion in PCT PCT/US2021/030261 dated Aug. 31, 2021 (18 pages).
International Search Report and Written Opinion in PCT/US2021/031596 dated Sep. 28, 2021 (12 pages).
International Search Report and Written Opinion in PCT/US2021/033832 dated Sep. 17, 2021.
International Search Report and Written Opinion received for Life Spine, Inc. for PCT app. PCT/US2021/026606 dated Jul. 15, 2021, 20 pages.
International Search Report and Written Opinion received for Life Spine, Inc., for PCT app. No. PCT/US2021026610 dated Jul. 20, 2021, 18 pages.
Bacfuse® Spinous Process Fusion Plate Surgical Technique, 2011, Pioneer Surgical, 12 pages.
Extended European Search Report for European Application No. 14159101.6, dated Jun. 18, 2014, 6 pages.
Extended European Search Report for European Application No. 16169890.7, dated Oct. 21, 2016, 7 pages.
Foreign Action other than Search Report on EP 06740268.5 DTD Jan. 2, 2020, 4 pages.
Foreign Action other than Search Report on PCT PCT/US2018/029120 DTD Nov. 7, 2019, 9 pages.
Foreign Action other than Search Report on PCT PCT/US2018/029149 DTD Nov. 7, 2019, 8 pages.
Foreign Action other than Search Report on PCT PCT/US2018/041306 DTD Jan. 23, 2020, 6 pages.
Foreign Search Report on PCT PCT/US2019/037275 DTD Sep. 24, 2019, 12 pages.
International Preliminary Report on Patentability for Application No. PCT/US06/12060 dated Sep. 30, 2007, 3 pages.
International Search Report and Written Opinion for International Application No. PCT/US2006/012060, mail date Apr. 5, 2007, 4 pages.
International Search Report and Written Opinion for International Application No. PCT/US2012/057324, mail date Dec. 20, 2012, 10 pages.
International Search Report for Application No. PCT/US06/12060, date of mailing Apr. 5, 2007, 1 page.
International Search Report for International Application No. PCT/US2018/029120, mail date Jun. 28, 2018, 17 pages.
International Search Report for International Application No. PCT/US2018/029149, mail date Jun. 25, 2018, 13 pages.
Search Report for International Application No. PCT/US2018/041306, mail date Sep. 28, 2018, 12 pages.
Written Opinion of the International Searching Authority for Application No. PCT/US06/12060, date of mailing Apr. 5, 2007, 3 pages.
International Search Report on PCT/US2020/037020, Sep. 29, 2020, 20 pages.
International Search Report and Written Opinion in PCT/US2022/053230 dated May 3, 2023 (18 pages).
International Search Report and Written Opinion on PCT/US2020/036809 DTD Sep. 14, 2020, 12 pages.
Final Office Action on U.S. Appl. No. 16/850,795 DTD Jul. 20, 2022.
Non-Final Office Action on U.S. Appl. No. 16/438,031 DTD Jul. 25, 2022.
International Search Report and Written Opinion in PCT/US2023/021528 dated Aug. 24, 2023 (17 pages).

* cited by examiner (A-A)

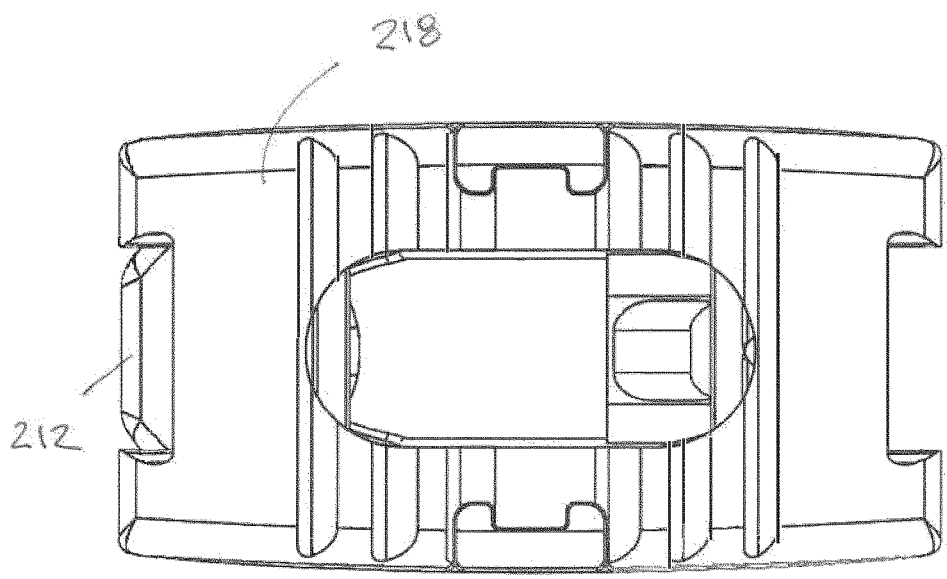
FIG. 34
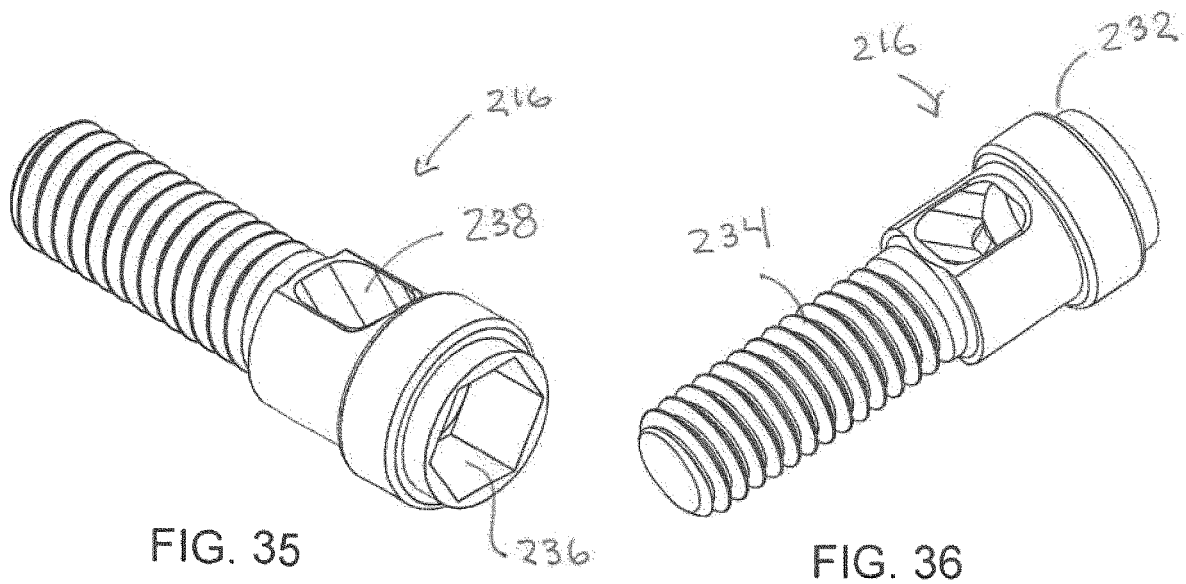
FIG. 35
FIG. 36

EXPANDABLE IMPLANT ASSEMBLY

CROSS-REFERENCE TO RELATED PATENT APPLICATIONS

This application is a continuation-in-part of U.S. application Ser. No. 16/548,134, filed on Aug. 22, 2019, which is continuation of U.S. application Ser. No. 15/497,044, filed Apr. 25, 2017 and granted Oct. 1, 2019 as U.S. Pat. No. 10,426,632, which is a continuation-in-part of U.S. application Ser. No. 14/714,821, filed May 18, 2015 and granted Oct. 31, 2017 as U.S. Pat. No. 9,801,733, which is a continuation-in-part of U.S. application Ser. No. 13/802,110, filed Mar. 13, 2013 and granted May 19, 2015 as U.S. Pat. No. 9,034,041, all of which are incorporated herein by reference in their entireties. This application is related to U.S. application Ser. No. 15/497,011, filed Apr. 25, 2017 and granted Aug. 20, 2019 as U.S. Pat. No. 10,383,741, which is incorporated herein by reference in its entirety.

BACKGROUND

The present disclosure relates to spinal interbody and intravertebral body devices and, more particularly, to vertebral interbody and intravertebral devices that are expandable after spinal placement thereof.

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posterolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

SUMMARY

One embodiment relates to an expandable implant, comprising a top support assembly defining an upper surface configured to engage a first portion of vertebral bone; a bottom support assembly defining a lower surface configured to engage a second portion of vertebral bone; a control assembly coupled to the top support assembly and the bottom support assembly and configured to control relative movement between the top support assembly and the bottom support assembly between a collapsed position and an expanded position; wherein in the collapsed position, the upper surface is generally parallel to the lower surface, and wherein in the expanded position, a portion of the upper surface extends at an acute angle relative to a portion of the lower surface.

Another embodiment relates to an expandable implant comprising a top support assembly defining an upper surface configured to engage a first portion of vertebral bone; a bottom support assembly defining a lower surface configured to engage a second portion of vertebral bone; a first wedge member slidably coupled to the top and bottom support assemblies; a second wedge member slidably coupled to the top and bottom support assemblies; and a control assembly coupled to the first and second wedge members and configured to control relative movement between the top support assembly and the bottom support assembly between a collapsed position and an expanded position; wherein in the collapsed position, the upper surface is generally parallel to the lower surface, and wherein in the expanded position, a portion of the upper surface extends at an angle relative to a portion of the lower surface.

Another embodiment relates to a method of using an expandable implant, comprising providing an expandable implant comprising a top support assembly, a bottom support assembly, and a control assembly coupled to the top and bottom support assemblies; manipulating the control assembly in a first manner to move the top support assembly in a linear fashion relative to the bottom support assembly; and manipulating the control assembly in a second manner to move at least a portion of the top support assembly in a non-linear fashion relative to at least a portion of the bottom support assembly.

Another embodiment relates to an expandable implant, comprising a top support configured to engage a first portion of vertebral bone; a bottom support configured to engage a second portion of vertebral bone; and a control assembly coupled to the top support and the bottom support and configured to control relative movement between the top support and the bottom support, wherein the control assembly includes a control member including a head and a body portion; and wherein the head includes a recess and the body portion includes at least one access port in fluid communication with the recess to enable delivery of fluid to an interior of the implant via the recess and at least one access port.

Another embodiment relates to an expandable implant, comprising a top support including a top surface configured to engage a first portion of vertebral bone; a bottom support including a bottom surface configured to engage a second portion of vertebral bone, wherein the top and bottom surfaces define a taper; and a control assembly coupled to the top support and the bottom support and configured to control relative movement between the top support and the bottom support, wherein the control assembly includes a control member having a recess and at least one access port in fluid communication with the recess to enable delivery of fluid to an interior of the implant via the recess and at least one access port.

Another embodiment relates to an implant comprising a top support configured to engage a first portion of vertebral bone; a bottom support configured to engage a second portion of vertebral bone; and a control assembly coupled to the top support and the bottom support and configured to control relative movement between the top support and the bottom support, wherein the control assembly includes a front portion configured to slidably engage the top and bottom supports; a rear portion configured to slidably engage the top and bottom supports; and a control member including a head disposed within the rear portion, and a threaded portion threadingly engaging the front portion; wherein the head includes a recess and at least one access port in fluid communication with the recess to enable delivery of fluid to an interior of the implant via the recess and at least one access port.

Another embodiment relates to an expandable implant. The expandable implant includes a top support configured to engage a first portion of bone, a bottom support configured to engage a second portion of bone, a control assembly coupled to the top support and the bottom support and configured to control relative movement between the top support and the bottom support, wherein the control assembly includes a front member and a control member, wherein the front member has an aperture configured to receive the control member, wherein the control member includes a head, and wherein a portion of the head is positioned outside of the aperture as the implant is expanded between a first, collapsed orientation and a second, expanded orientation.

Another embodiment relates to a method of installing an expandable implant. The method includes inserting the implant into a desired location. The implant includes an upper support configured to engage a first portion of bone, a lower support configured to engage a second portion of bone, and a control assembly comprising a control member including a head, a front member including an aperture configured to receive the control member, and a rear member, wherein the control assembly is configured to control relative movement between the upper support and the lower support. The method includes manipulating the control member to cause relative sliding movement between the front member and both the upper support and the lower support, and the rear member and both the upper support and the lower support, to expand the implant to a desired height, wherein a portion of the head is positioned outside of the aperture as the implant is expanded between a first, collapsed orientation and a second, expanded orientation.

Another embodiment relates to an implant. The implant includes an upper support configured to engage a first portion of bone, a lower support configured to engage a second portion of bone, a control assembly configured to control relative movement between the upper support and the lower support. The control assembly includes a front portion configured to engage the upper support at the first end of the upper support, a rear portion configured to engage the upper support at a second end of the upper support, the second end being opposite the first end, and a control member adjustably engaging the front portion and the rear portion.

BRIEF DESCRIPTION

The foregoing and other features of the present invention will become more apparent to one skilled in the art upon also reading the following description of embodiments with reference to the accompanying drawings.

FIGS. 31-38 show various views of an expandable implant according to an alternative embodiment.

Figure 1:
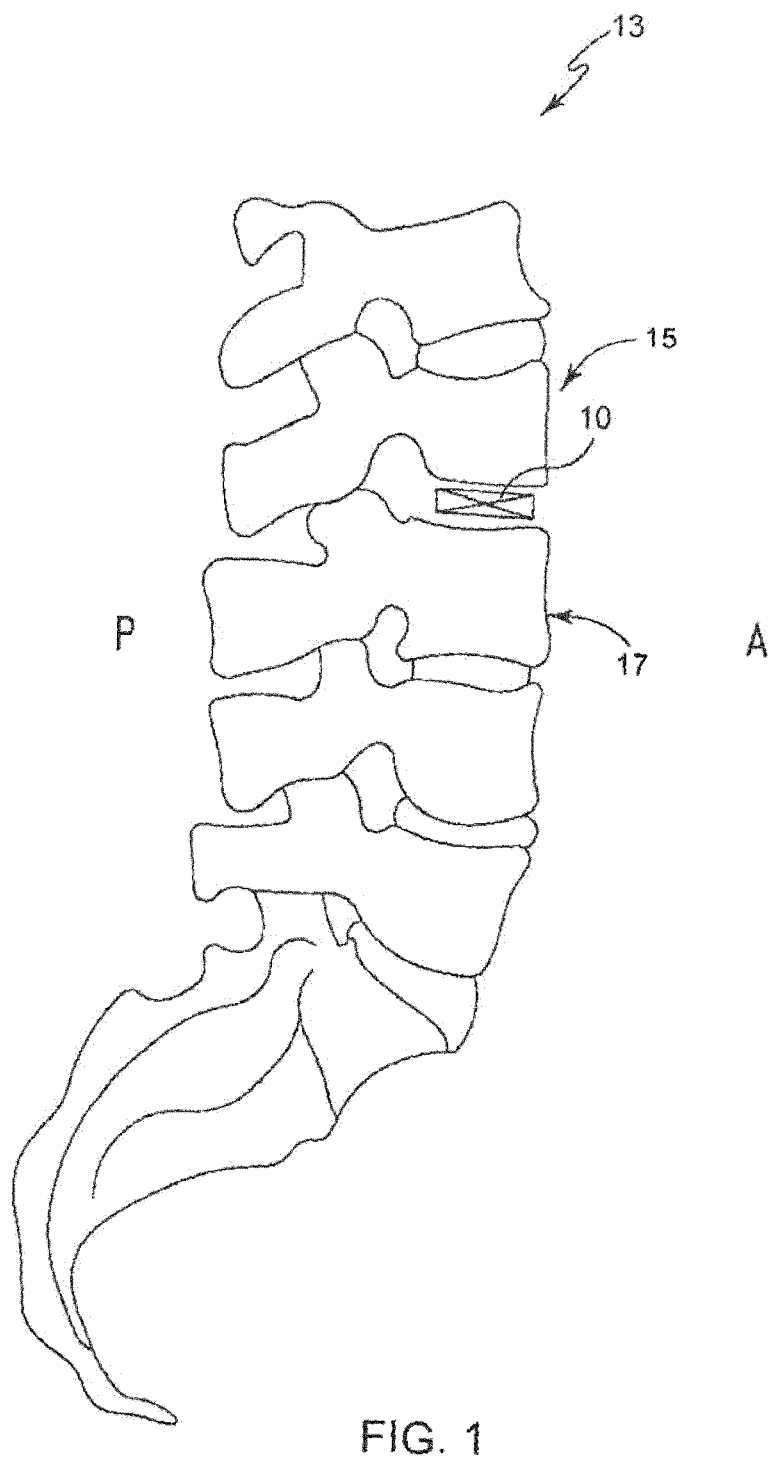
FIG. 1 is a side view of a portion of a human spine illustrating inter-vertebral placement of an expandable inter-body/intravertebral body device in accordance with the principles of the present invention.
Figure 2:
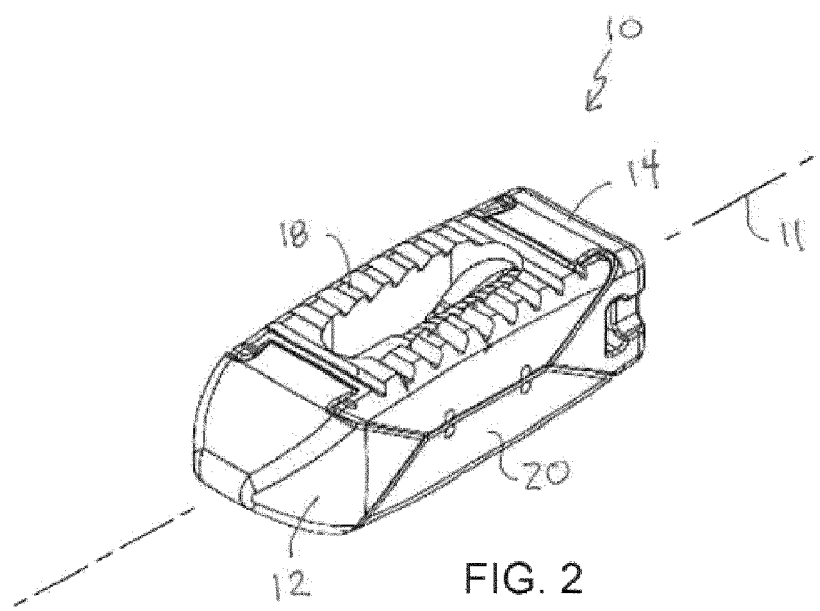
FIGS. 2-15 show various views of an expandable implant according to one embodiment.
Figure 3:
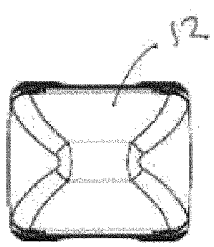
Figure 4:
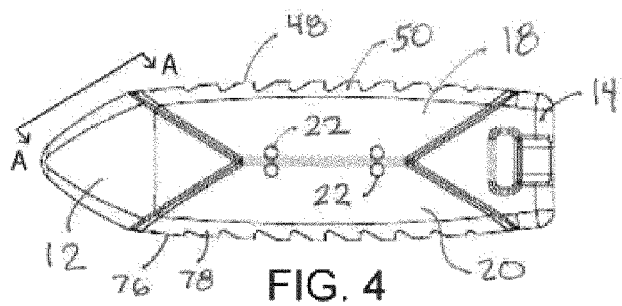
Figure 5:
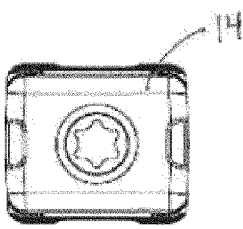
Figure 6:
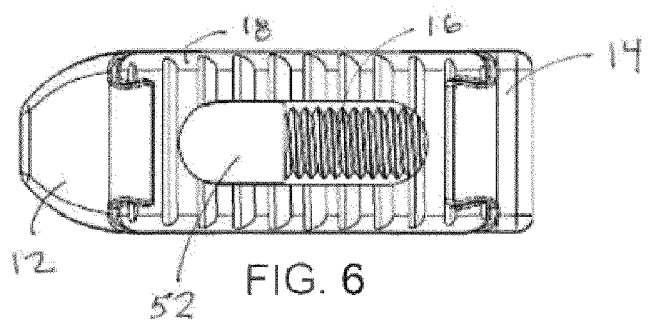
Figure 7:
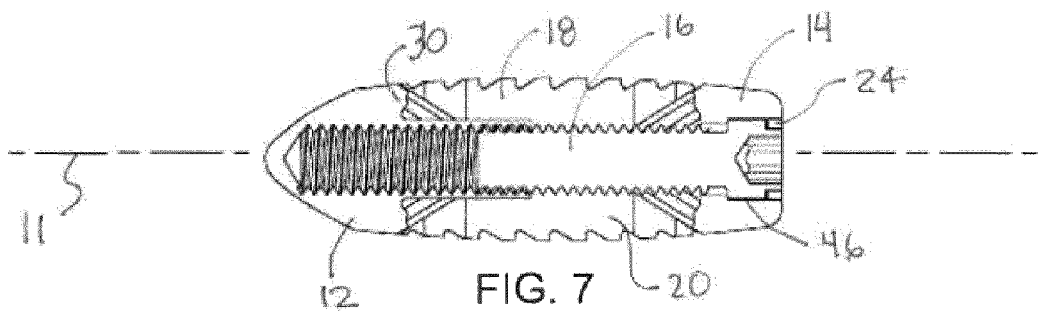
Figure 8:
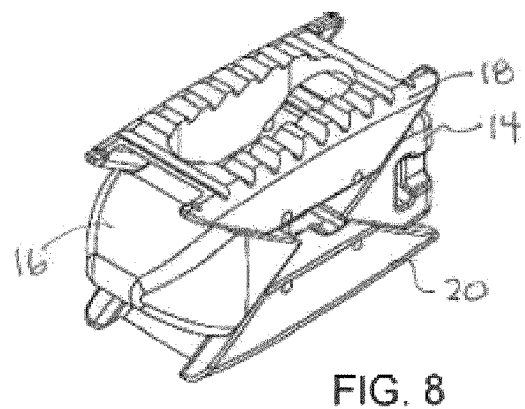
Figure 9:
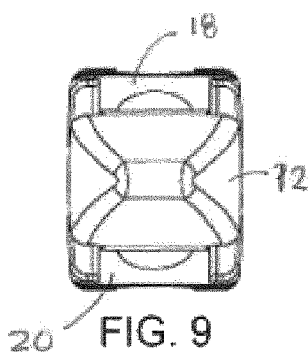
Figure 10:
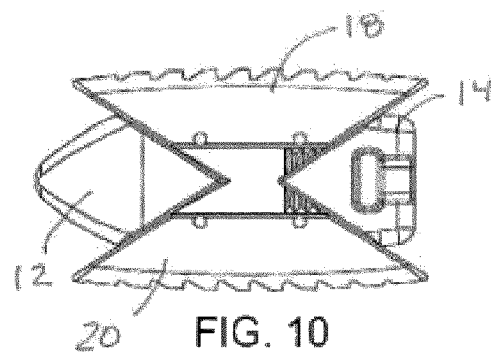
Figure 11:
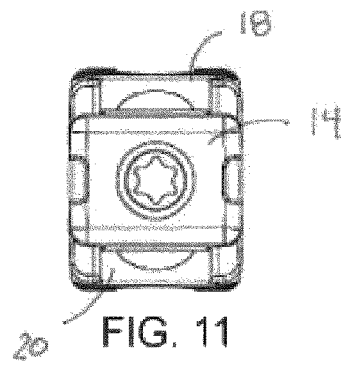
Figure 12:
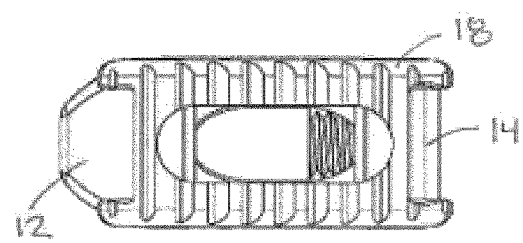
Figure 13:
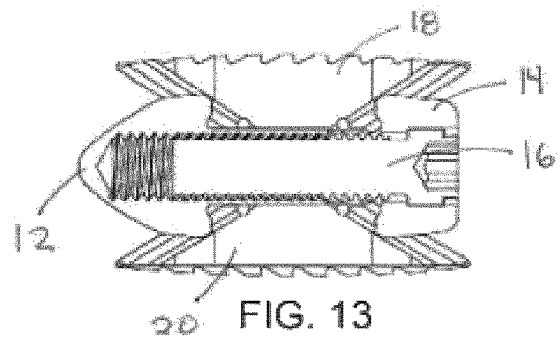

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION

The present disclosure relates to expandable and/or dynamic interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present disclosure provides various versions of dynamic (expandable and/or expandable and retractable) interbody/intravertebral body devices that are usable in a spinal column of a human.

As representative of each one of the various versions of the present invention, FIG. 1 illustrates a representative dynamic spinal body device or expandable implant 10. The implant 10 is depicted as implanted or inserted into a human spine 13 of which only a lower portion of the spine 13 is shown. The implant 10 is illustrated implanted between adjacent upper and lower vertebrae 15, 17 of the spine 13 in FIG. 1 (hence interbody or intervertebral). Vertebrae 15 and 17 have portions that face anteriorly ("A", and from the right as viewed in FIG. 1) and portions that face posteriorly ("P", and from the left as viewed in FIG. 1).

According to various exemplary embodiments, the components of implant 10 may be made of any suitable material(s), including a variety of metals, plastics, composites, or other suitable bio-compatible materials. In some embodiments, one or more components of implant 10 may be made of the same material, while in other embodiments, different materials may be used for different components of implant 10.

Referring now to FIGS. 2-15, expandable implant 10 is shown according to an exemplary embodiment. Implant 10 is usable, for example, between and/or within vertebral bodies of the spine, and may share many of the features of the other inter/intra-body implants discussed elsewhere herein. It should be understood that implant 10 may in some embodiments be usable in other portions of the body in addition to the spine, and all such applications are to be understood to be within the scope of the present disclosure.

According to an exemplary embodiment, implant 10 includes a first, or front portion 12 (e.g., a first wedge member), a second, or rear portion 14 (e.g., a second wedge member), and a third, intermediate, or control member or portion 16, which collectively form a body or control assembly that extends along a longitudinal axis 11 of implant 10. A first, or upper support 18 (e.g., an upper plate, support member, assembly, etc.) and a second, lower support 20 (e.g., a lower plate, support member, assembly), are coupled to the body assembly and extend generally between front and rear portions 12, 14. According to an exemplary embodiment, first and second supports 18, 20 define a height of implant 10 extending between outer or top surface 48 of first support 18 and outer or lower surface 76 of second support 20.

In one embodiment, front portion 12 includes a rounded, or bull nose portion intended to facilitate insertion of implant 10 into a patient. Front portion 12 also includes ramped surfaces 26, 28 and projections 30, 32 that facilitate controlled sliding movement between front portion 12 and first and second supports 18, 20. An aperture 34 may be threaded to receive control member 16 to provide an adjustable control mechanism for implant 10.

Figure 14:
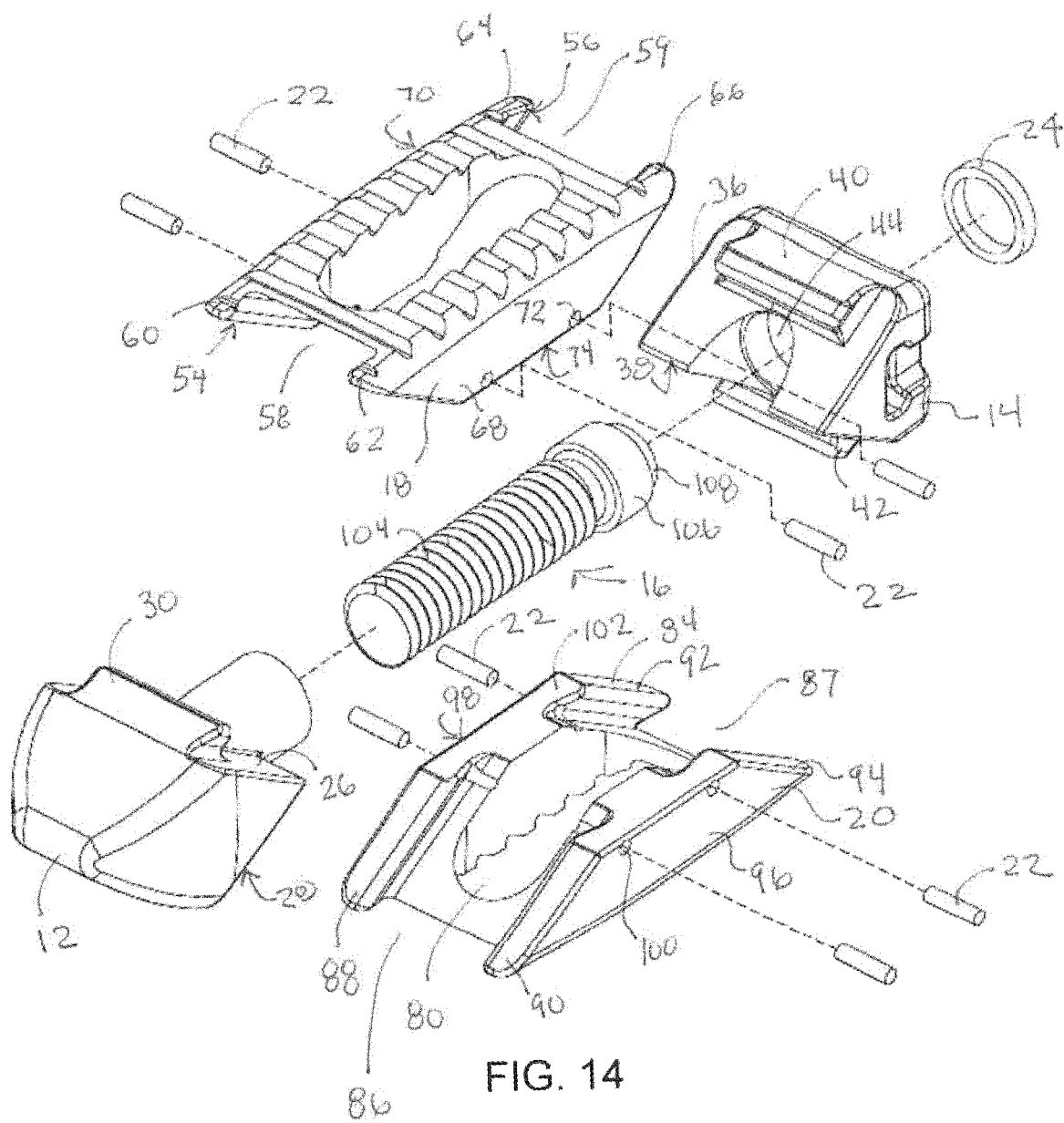
Figure 15:
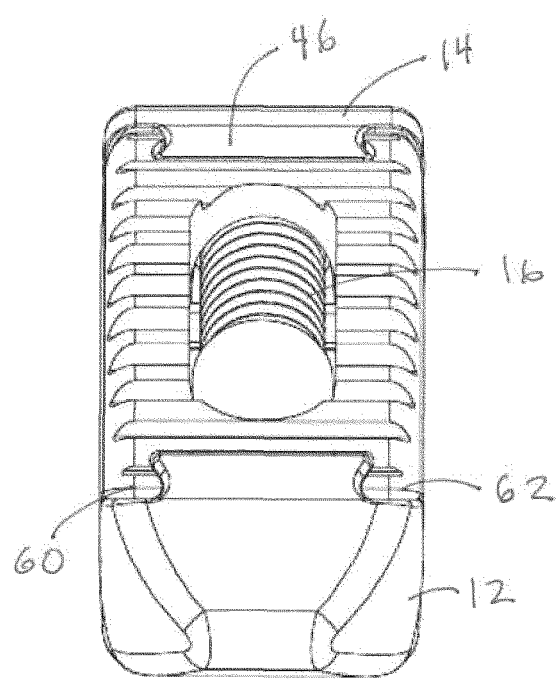

Referring to FIG. 14, ramped surface 26 extends at an angle relative to axis 11, and projection 30 extends upward relative to ramped surface 26. Ramped surface 26 is a generally flat surface configured to engage a correspondingly ramped surface (surface 54) on first support 18. Projection 30 extends laterally across front portion 12. In some embodiments, projection 30 may have a dovetail shape, while in other embodiments, projection 30 may take other shapes, including having an undercut portion, etc. The dovetail shape provides a relatively larger top portion and an undercut lower portion such that front portion 12 and first support 18 can slide relative to one another, but the parts cannot be separated, for example, by merely lifting first support 18 away from front portion 12 (e.g., in an upward direction generally perpendicular to axis 11).

Ramped surface 28 and projection 32 share similar features to ramped surface 26 and projection 30, except that ramped surface 28 and projection 32 interface with corresponding surfaces on second support 20, rather than first support 18. It should be noted that ramped surfaces 26, 28 may be inclined relative to axis 11 to provide any desirable adjustment features, as changing the incline of the ramped surfaces will change the rate at which the first and second support members move up/down.

Referring further to FIG. 14, according to an exemplary embodiment, rear portion 14 includes ramped surfaces 36, 38, projections 40, 42, an aperture, or through-hole 44, and a counterbore 46. Rear portion 14 may define a generally flat rearward-most surface being generally rectangular in shape. In other embodiments, the shape of rear portion 14 may be varied to suit a particular application.

Ramped surface 36 extends at an angle relative to axis 11, and projection 40 extends upward relative to ramped surface 36. Ramped surface 36 is a generally flat surface configured to engage a correspondingly ramped surface (surface 56) on first support 18. Projection 40 extends laterally across rear portion 14. In some embodiments, projection 40 may have a dovetail shape (see, e.g., FIG. 15), while in other embodiments, projection 40 may take other shapes, including having an undercut portion etc. The dovetail shape provides a relatively larger top portion and an undercut lower portion such that rear portion 14 and first support 18 can slide relative to one another, but the parts cannot be separated, for example, by merely lifting first support 18 away from rear portion 14 (e.g., in an upward direction generally perpendicular to axis 11).

Ramped surface 38 and projection 42 share similar features to ramped surface 36 and projection 40, except that ramped surface 38 and projection 42 interface with corresponding surfaces on second support 20, rather than first support 18. It should be noted that ramped surfaces 36, 38 may be inclined relative to axis 11 to provide any desirable adjustment features, as changing the incline of the ramped surfaces will change the rate at which the first and second support members move up/down.

According to an exemplary embodiment, first and second supports 18, 20 are configured to be moveable relative to the body or control assembly (e.g., front and rear portions 12, 14 and control portion 16) such that implant 10 is reconfigurable between a first configuration (e.g., a retracted, collapsed, or minimal configuration), as shown in FIGS. 2-7, and a second configuration (e.g., an expanded or maximum configuration), as shown in FIGS. 8-13 and any intermediate position therebetween. Control member 16 is rotatable and threadingly received by front portion 12 such that rotation of control member 16 in a first (e.g., clockwise) direction causes front and rear portions 12, 14 to move toward each other, thereby causing first and second supports 18, 20 to move outward toward the expanded configuration. Conversely, rotation of control member 16 in a second (e.g., counter-clockwise) direction causes front and rear portions 12, 14 to move away from each other, thereby causing first and second supports 18, 20 to move inward toward the collapsed configuration. It should be noted that in use, control member 16 may be adjusted so as to maintain first and second supports 18, 20 in a fully collapsed configuration, a fully expanded configuration, or any desired configuration or intermediate position therebetween.

First and second supports 18, 20 and front and rear portions 12, 14 have corresponding geometric features (e.g., correspondingly ramped surfaces) such that displacement of front portion 12 relative to rear portion 14 along axis 11 causes relative planar and/or linear displacement of first and second supports 18, 20. As discussed above, the geometric features of the various components may be varied to provide for varying adjustment features for first and second supports 18, 20.

In one embodiment, first and second supports 18, 20 are generally similar in structure. Referring to FIG. 14, first support 18 includes outer, or top surface 48, ramped surfaces 54, 56, channels 58, 59, and two pairs of opposing projections—projections 60, 62, and projections 64, 66. First support 18 further includes sidewalls 68, 70, pin or retaining member apertures 72, and inner, or bottom surface 74. Top surface 48 includes a number of ridges, or projections 50, intended to provide a gripping surface for adjacent vertebrae, and a bone graft cavity, or window 52 intended to provide a space to receive bone graft material.

In use, control member 16 extends through through-hole 44 in rear portion 14 and into front portion 12. Head portion 106 of control member 16 seats in counterbore 46 of rear portion 14, and threaded portion 104 threadingly engages aperture 34 of front portion 12. Head portion 106 may include an annular recess 108 configured such that a collar 24 can be positioned (e.g., press-fit, welded, etc.) into counterbore 46 rearward of head portion 106 to retain control member 16 in place. As a user rotates control member 16, front portion 12 and rear portion 14 move toward/away from each other (depending on the direction of rotation), and first and second supports 18, 20 in turn move away from/toward each other.

As shown in FIG. 14, opposing projections 60, 62 on first support 18 form a recess, or channel 58. In one embodiment, channel 58 has a dovetail shape corresponding in shape to projection 30 on front portion 12. Likewise, projections 64, 66 in first support 18 form channel 59 having a dovetail shape similar in shape to projection 40 on rear portion 14. Projections 30, 40 slide within channels 58, 59 as first support 18 moves up/down. Retaining members or pins 22 extend through first and second supports 18, 20 and act to limit the range of movement of first and second supports 18, 20 relative to front and rear portions 12, 14, and prevent first and second supports 18, 20 from being completely removed from front and rear portions 12, 14.

Second support 20 is similar to first support 18 and includes outer, or bottom surface 76, ramped surfaces 82, 84, channels 86, 87, and two pairs of opposing projections—projections 88, 90, and projections 92, 94. Second support 20 further includes sidewalls 96, 98, pin or retaining member apertures 80, and inner, or top surface 102. Bottom surface 76 includes a number of ridges, or projections 78, intended to provide a gripping surface for adjacent vertebrae, and a bone graft cavity, or window 80 intended to provide a space to receive bone graft material. In one embodiment, the components of second support 20 are similar in structure and function to the corresponding components of first support 18. In other embodiments, the components of second support 20 may provide additional and/or different structural and/or functional features relative to the corresponding components of first support 18.

It should be noted that implant 10 may share various features with the other implants described herein, and be made of the same, similar, or different materials. For example, various components of implant 10 may be made of metal, plastic, composites, or other suitable bio-compatible materials. Further, implant 10 may be usable in connection with the spine or other parts of the body.

Referring now to FIGS. 16-30, an expandable implant 110 is shown according to an exemplary embodiment. Implant 110 is usable, for example, between and/or within vertebral bodies of the spine, and may share many of the features of the other inter/intra-body implants discussed elsewhere herein. It should be understood that implant 110 may in some embodiments be usable in other portions of the body in addition to the spine, and all such applications are to be understood to be within the scope of the present disclosure. Implant 110 is generally similar to implant 10 in structure and function except with respect to the additional alignment features discussed below.

According to an exemplary embodiment, implant 110 includes a first, or front portion 112, a second, or rear portion 114, and a third, intermediate, or control member or portion 116, which collectively form a body or control assembly that extends along a longitudinal axis 111 of implant 110. A first, or upper support 118 (e.g., an upper plate or support member, etc.) and a second, lower support 120 (e.g., a lower plate or support member), are coupled to the body or control assembly and may extend generally between front and rear portions 112, 114. According to an exemplary embodiment, first and second supports 118, 120 define a height of implant 110 extending between outer or top surface 148 of first support 118 and outer or lower surface 176 of second support 120.

In one embodiment, front portion 112 includes a rounded, or bull nose portion intended to facilitate insertion of implant 110 into a patient. Front portion 112 also includes ramped surfaces and projections (e.g., similar to ramped surfaces 26, 28 and projections 30, 32) that facilitate controlled sliding movement between front portion 112 and first and second supports 118, 120. An aperture may be threaded to receive control member 116 to provide an adjustable control mechanism for implant 110.

Figure 20:
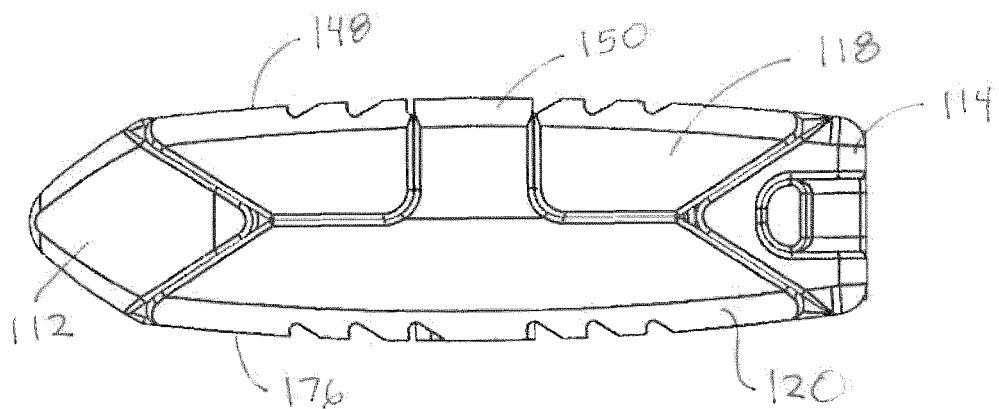
Figure 21:
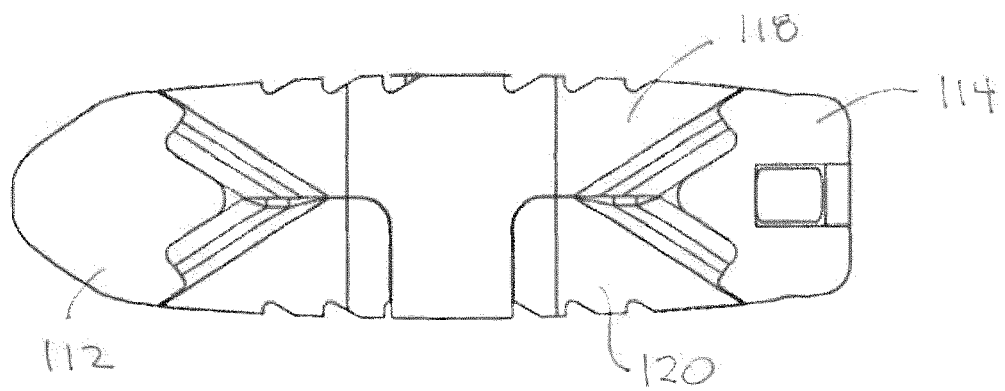
Figure 22:
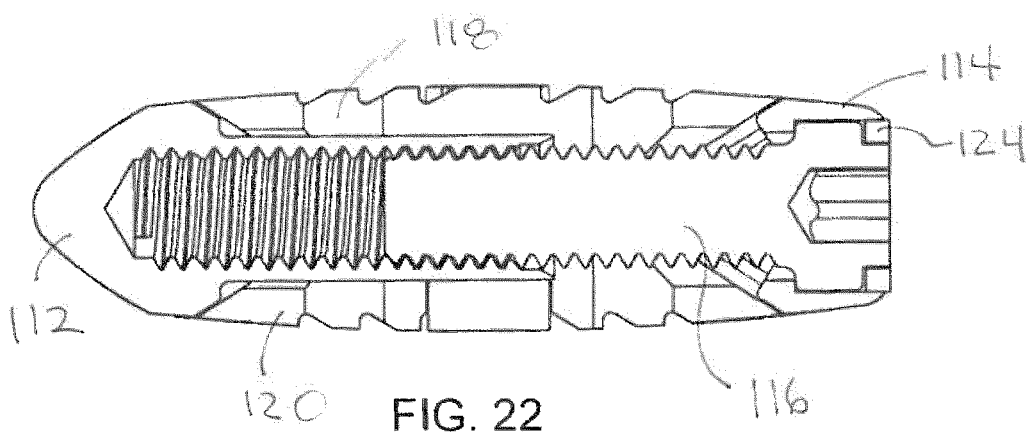
Figure 23:
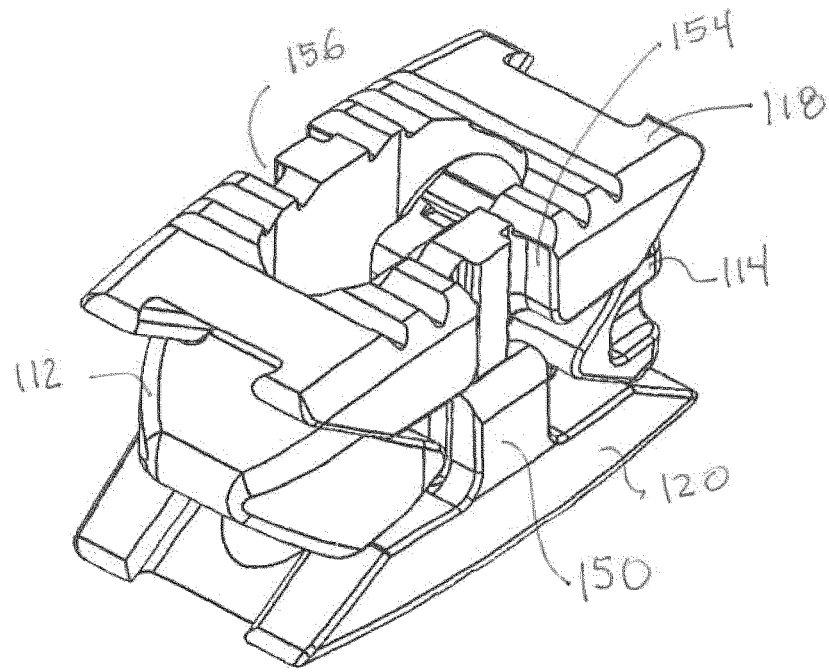
Figure 24:
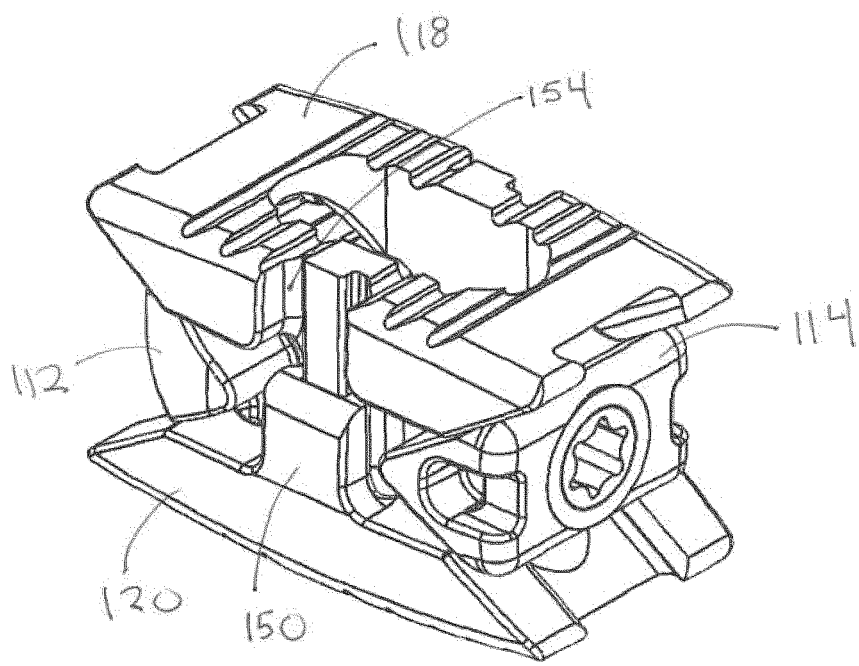
Figure 25:
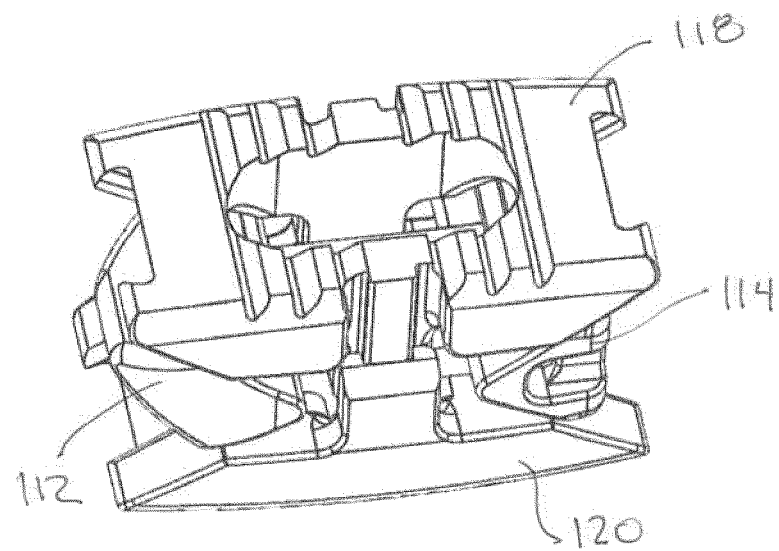
Figure 26:
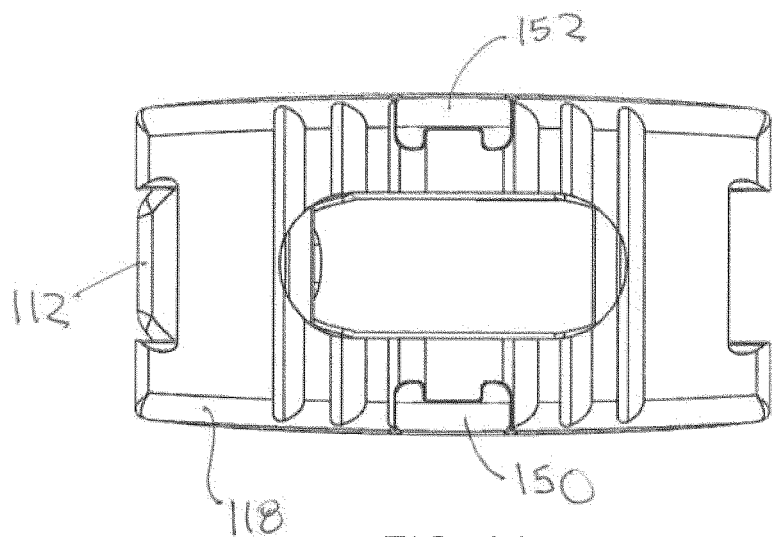
Figure 27:
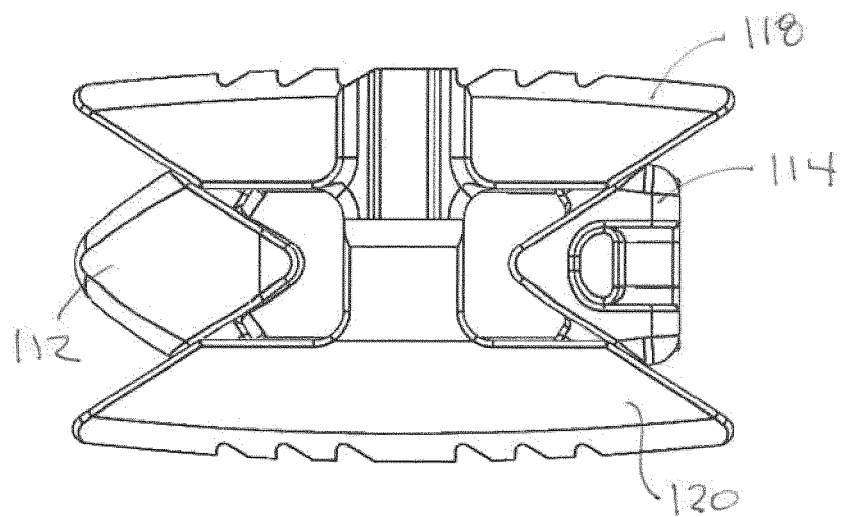
Figure 28:
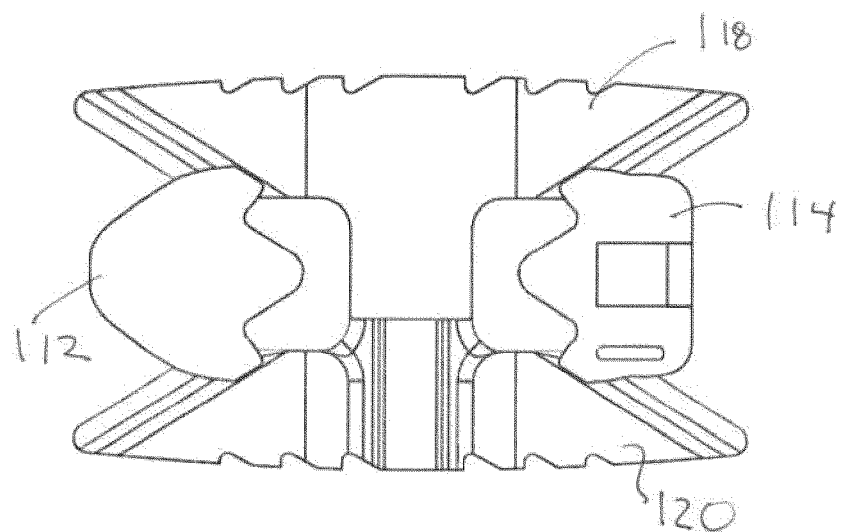
Figure 29:
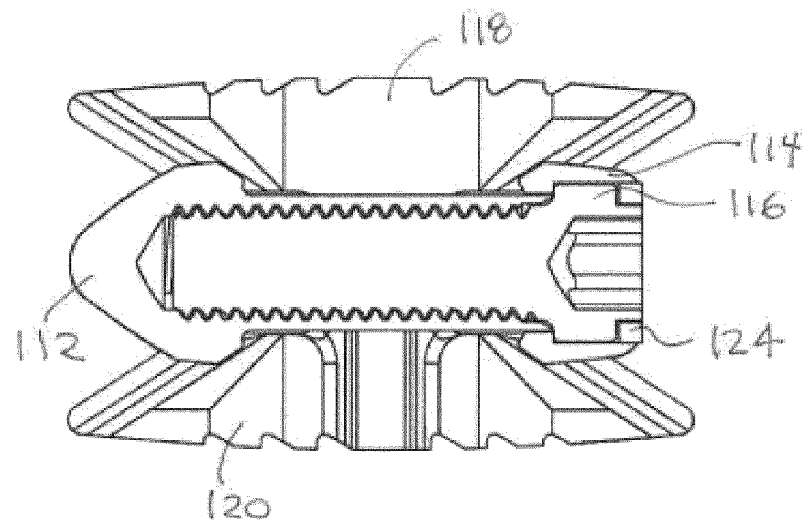
Figure 30:
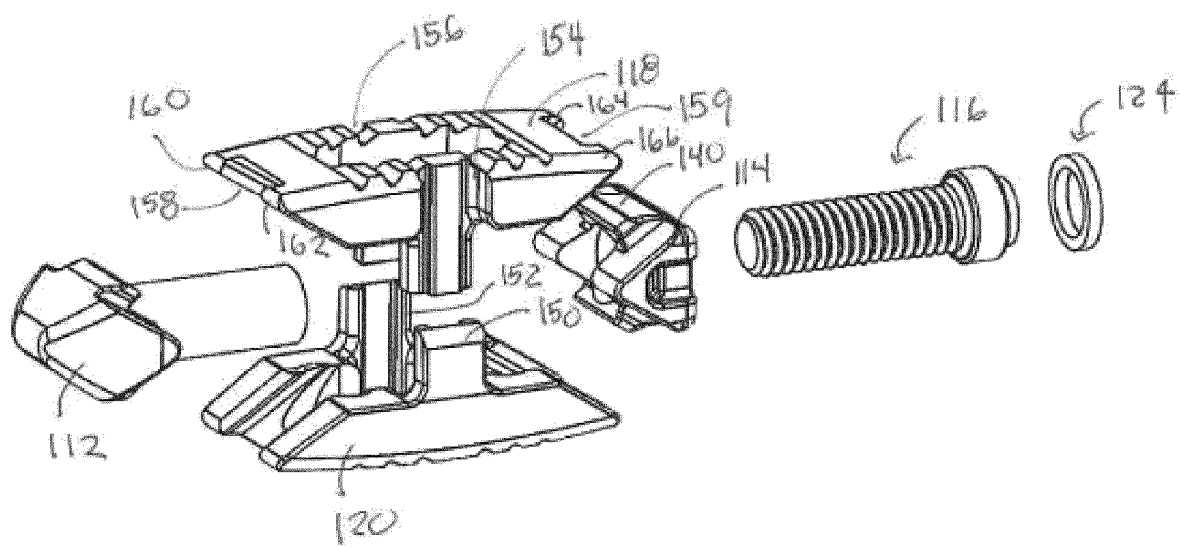
Figure 31:
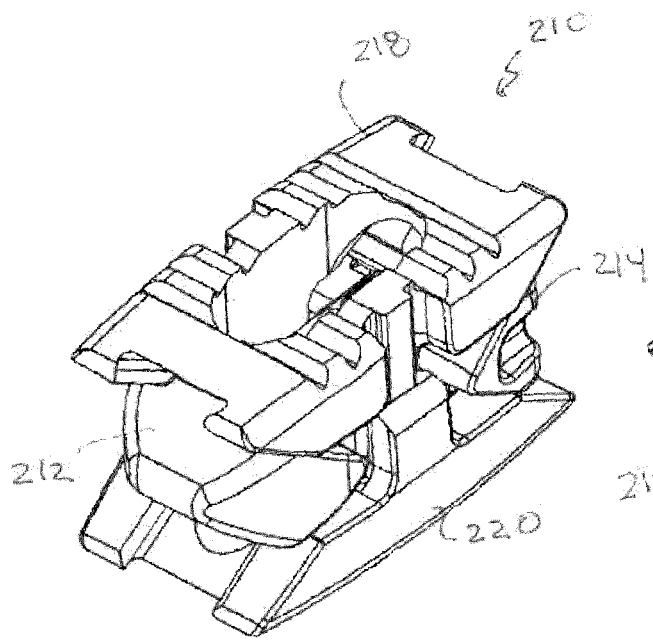
Figure 32:
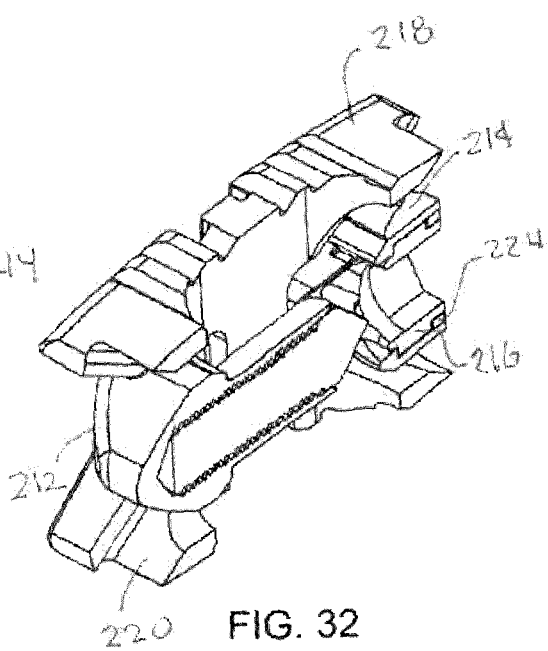
Figure 33:
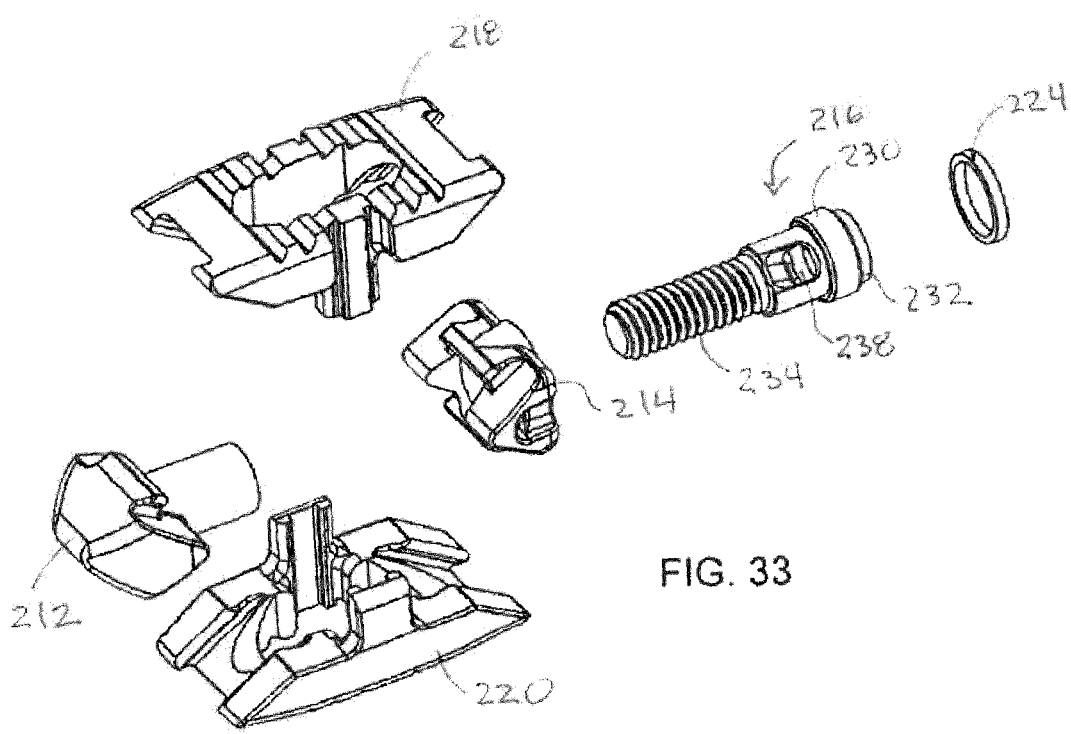
Figure 37:
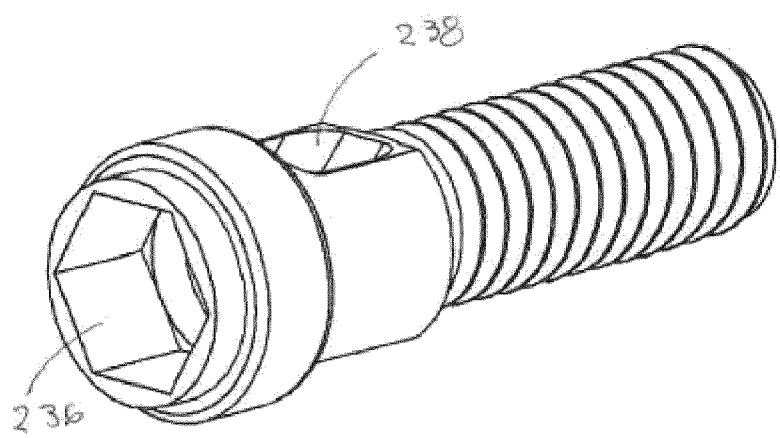
Figure 38:
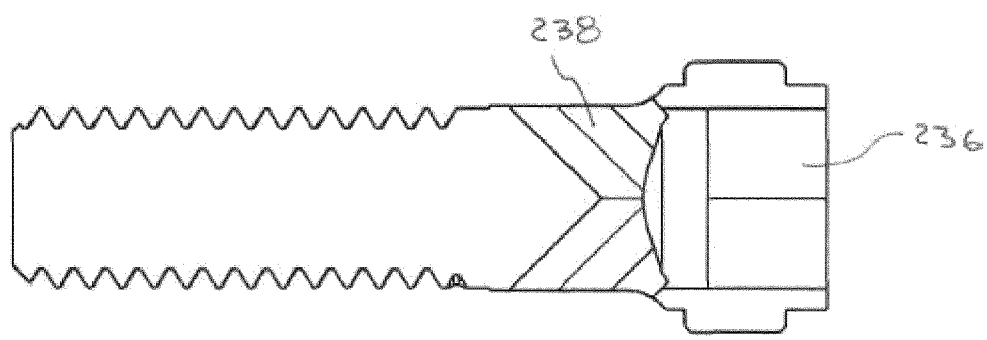
Figure 39:
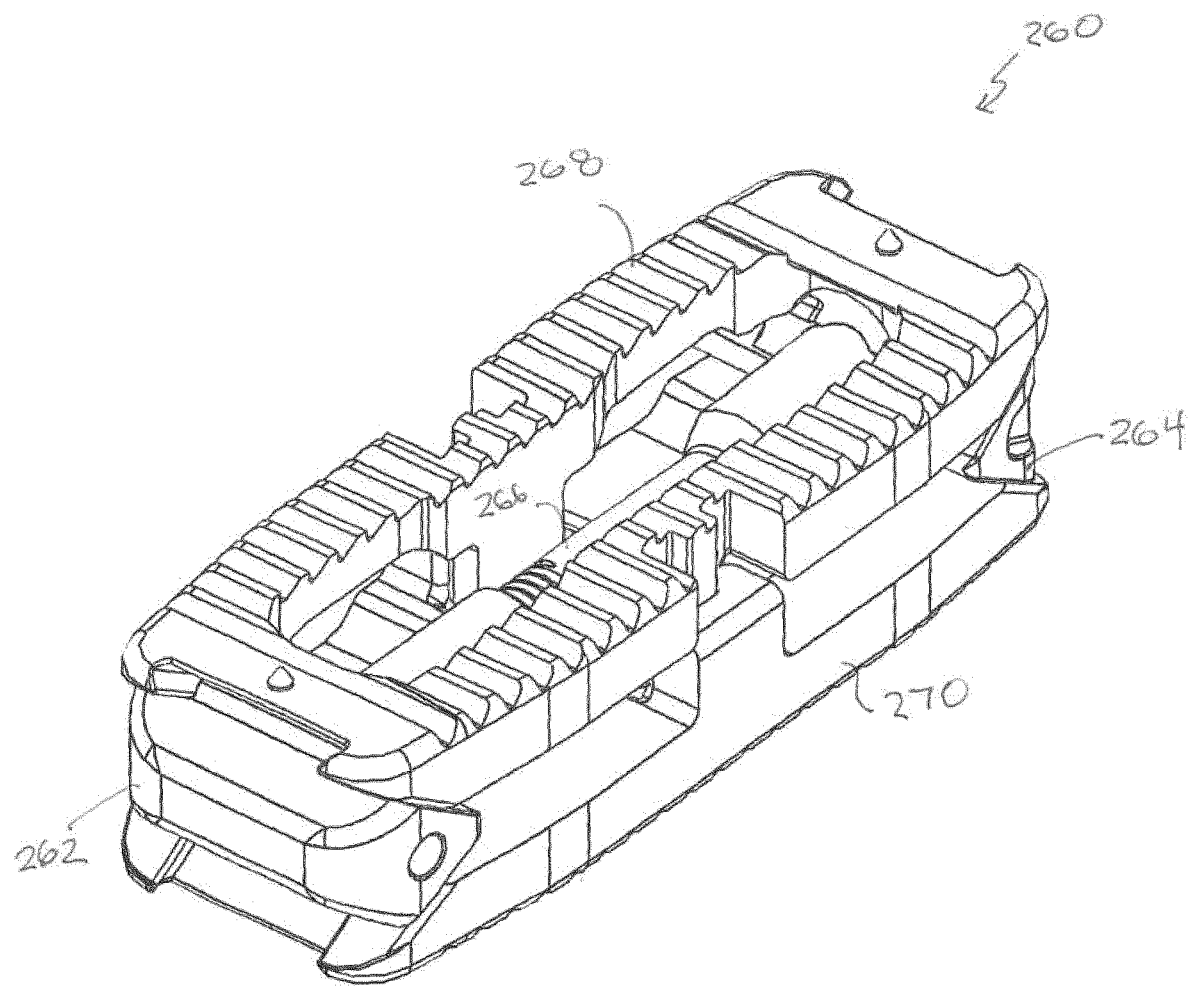
FIGS. 39-46 show various views of an expandable implant according to an alternative embodiment.
Figure 40:
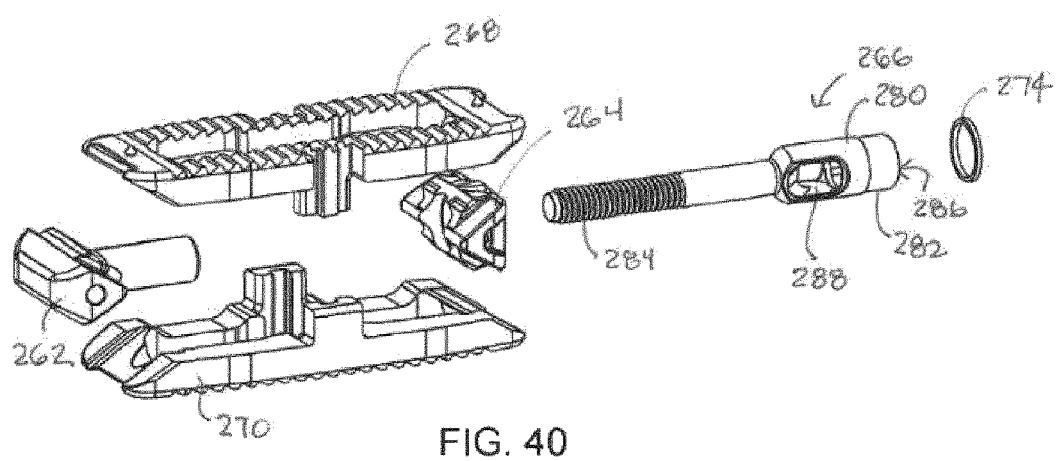
Figure 41:
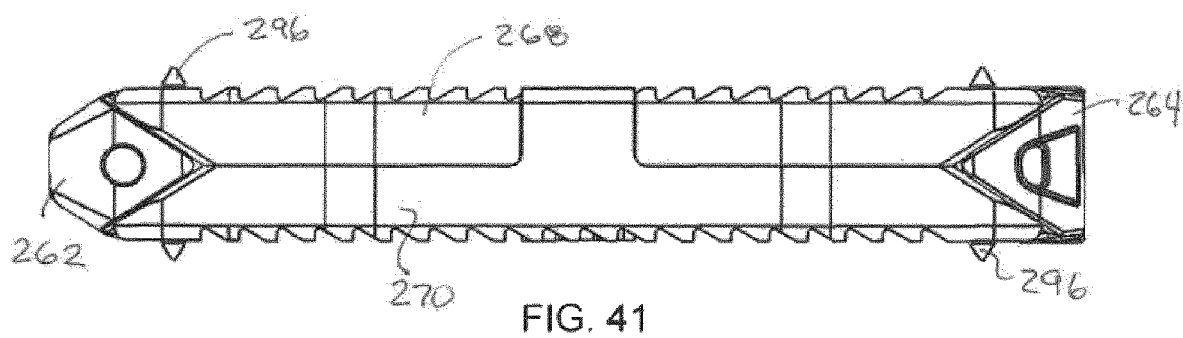

As shown in FIGS. 20-22, the ramped surfaces extend at an angle relative to axis 111, and the projections extend upward/downward relative to the ramped surfaces. The ramped surfaces are generally flat surfaces configured to engage a correspondingly ramped surface on first support 118. The projections extend laterally across front portion 112. In some embodiments, the projections may have a dovetail shape, while in other embodiments, the projections may take other shapes, including having an undercut portion, etc. The dovetail shape provides a relatively larger top portion and an undercut lower portion such that front portion 112 and first support 118 can slide relative to one another, but the parts cannot be separated, for example, by merely lifting first support 118 away from front portion 112 (e.g., in an upward direction generally perpendicular to axis 111). It should be noted that similar to implant 10, implant 110 includes front and rear, upper and lower ramped surfaces and projections configured to provide the interface between front and rear portions 112, 114 and first and second supports 118, 120.

As with implant 10, according to an exemplary embodiment, first and second supports 118, 120 and front and rear portions 112, 114 have corresponding geometric features (e.g., correspondingly ramped surfaces) such that displacement of front portion 112 relative to rear portion 114 along axis 111 causes relative planar and/or linear displacement of first and second supports 118, 120. As discussed above, the geometric features of the various components may be varied to provide for varying adjustment features for first and second supports 118, 120.

In use, control member 116 includes a head portion and a body portion and extends through a through-hole in rear portion 114 and into front portion 112. The head portion of control member 116 seats in a counterbore of rear portion 114, and the threaded portion of the body threadingly engages an aperture of front portion 112. The head portion may include an annular recess (similar to head portion 106 of implant 10) configured such that a collar 124 can be positioned (e.g., press-fit, welded, etc.) into the counterbore rearward of the head portion to retain control member 116 in place. As a user rotates control member 116, front portion 112 and rear portion 114 move toward/away from each other (depending on the direction of rotation), and first and second supports 118, 120 in turn move away from/toward each other. While the Figures generally show control member 116 threadingly engaging front portion 112, in other embodiments, other adjustment mechanisms may be used (e.g., ratchet mechanisms, indents/detents, etc.).

Opposing projections 160, 162 on first support 118 form a recess, or channel 158. In one embodiment, channel 158 has a dovetail shape corresponding in shape to projection 130 on front portion 112. Likewise, projections 164, 166 in first support 118 form channel 159 having a dovetail shape similar in shape to projection 140 on rear portion 114. Projections 130, 140 slide within channels 158, 159 as first support 118 moves up/down. In some embodiments, retaining members or pins (e.g., similar to pins 22) extend through first and second supports 118, 120 and act to limit the range of movement of first and second supports 118, 120 relative to front and rear portions 112, 114, and prevent first and second supports 118, 120 from being completely removed from front and rear portions 112, 114. Second support 120 includes similar features such as an outer, or bottom surface, ramped surfaces, channels, and two pairs of opposing projections.

Figure 16:
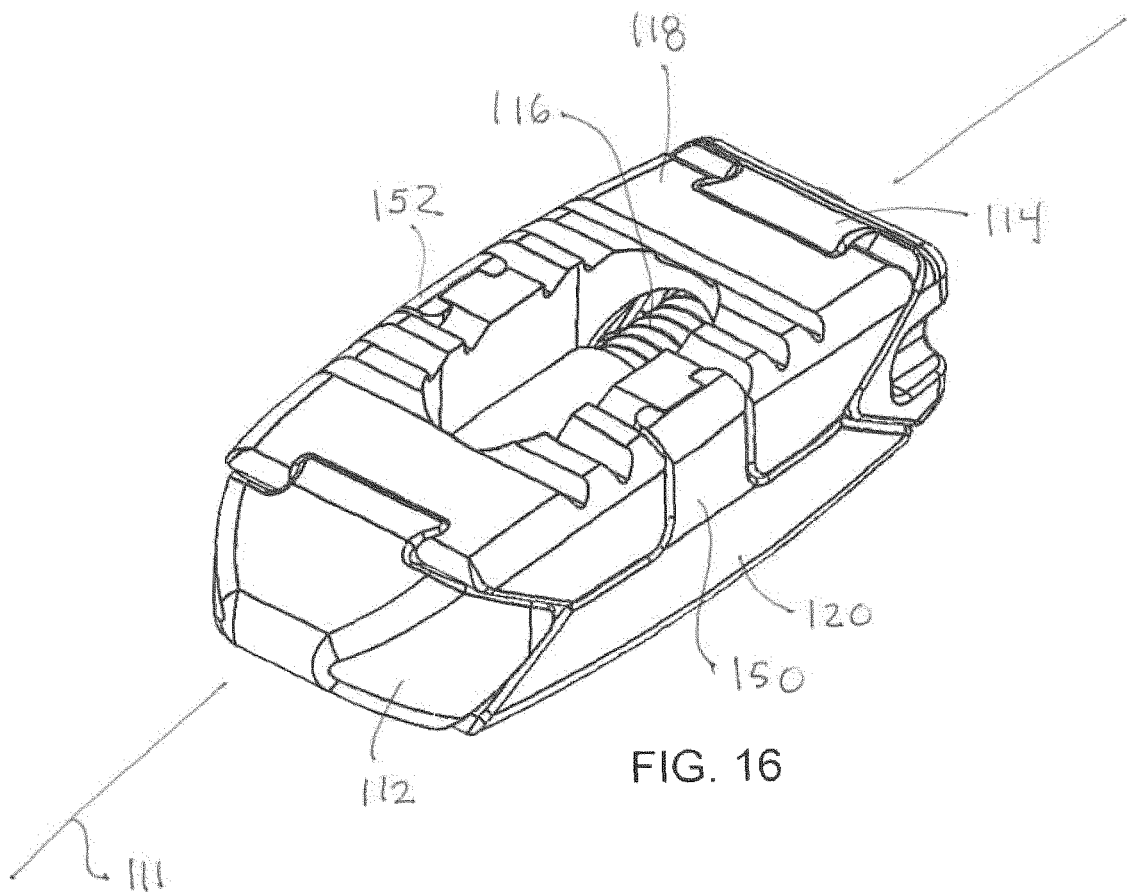
FIGS. 16-30 show various views of an expandable implant according to an alternative embodiment.
Figure 17:
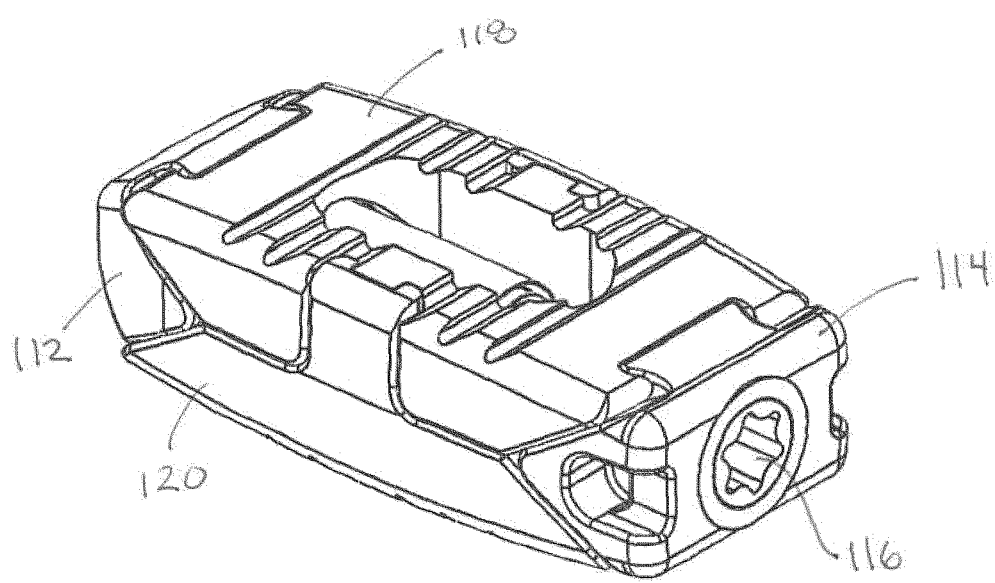
Figure 18:
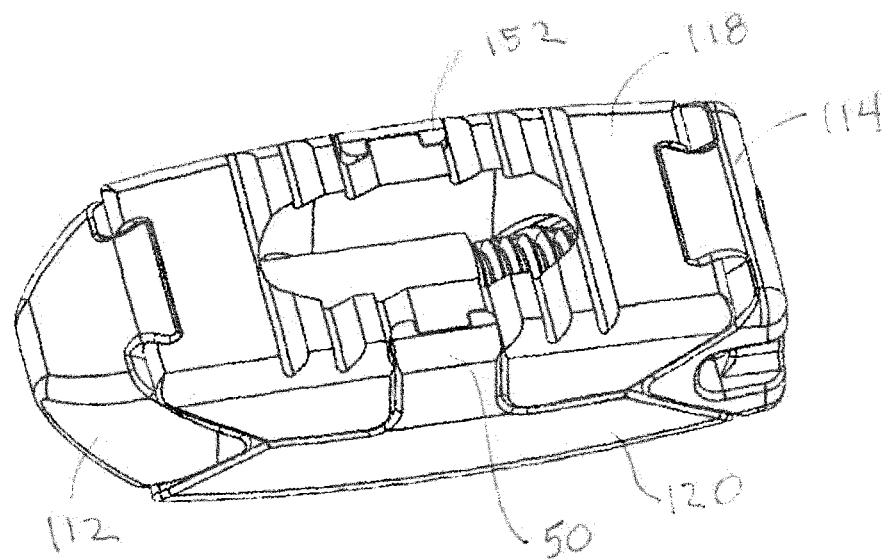
Figure 19:
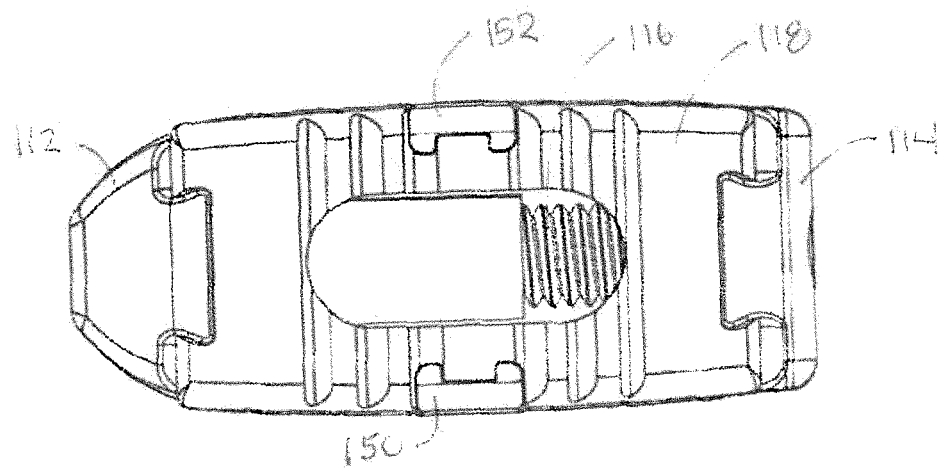

In addition to including various features of implant 10, implant 110 further includes an alignment feature intended to maintain alignment between first and second supports 118, 120 during use. In one embodiment, second support 120 includes one or more alignment members 150, 152 (e.g., extensions, projections, etc.) that extend generally upward as shown in FIG. 19 (e.g., in a direction generally perpendicular to axis 111). Members 150, 152 are received in recesses 154, 156 (e.g., channels, grooves, slots, etc.), respectively, formed in first support 118. Members 150, 152 and recesses 154, 156 have corresponding geometric features to ensure a snug fit between components. For example, as shown in FIG. 16, members 150, 152 are generally U-shaped in cross-section, and recesses 154, 156 are shaped to receive the U-shaped members. The alignment features prevent relative "rocking" of the supports, and in some embodiments serve to maintain a generally parallel relationship between the supports. In some embodiments, spaces or gaps may be provided between members 150, 152 and recesses 154, 156 to enable a predetermined amount of angular offset between the supports.

In one embodiment members 150, 152 are formed so as to be generally flush with the exterior surface of first support 118 (e.g., along a side or top surface). In other embodiments, members 150 may be recessed from, or alternatively protrude beyond, the exterior surface of first support 118. Further, while FIGS. 16-30 show two alignment members 150, 152 in various alternative embodiments, fewer or more alignment members and/or recesses may be utilized (e.g., 1, 3, 4, etc.). Further yet, members 150, 152 may be integrally formed with, or removably coupled to, a remainder portion of second support 120. In further embodiments, the relative positions of alignment members 150, 152 and recesses 154, 156 are reversed (e.g., such that members 150, 152 are provided on first support 118 and recesses 154, 156 are provided on second support 120). Other variations in the size, number, and placement of members 150, 152 and recesses 154, 156 may be made according to various embodiments.

It should be noted that implant 110 may share various features with the other implants described herein, and be made of the same, similar, or different materials. For example, various components of implant 110 may be made of metal, plastic, composites, or other suitable bio-compatible materials. Further, implant 110 may be usable in connection with the spine or other parts of the body. Further yet, pins similar to pins 22 may be used in conjunction with implant 110 or any of the other implants shown and described herein.

In various embodiments, the implants shown in FIGS. 1-15 and 16-30 share various common features. For example, the control member or screw (e.g., 16, 116) is contained within the device, such that neither end of the control member or screw protrudes past the end members. For example, as shown in FIG. 14, control member 16 may be received by or through rear portion 14 in a counterbore and held captive by collar or ring 24, such that control member 16 is free to rotate within rear portion 14, but does not threadingly engage rear portion 14. As such, rear portion 14 remains fixed relative to control member 16 as control member 16 is rotated. Control member 16 threadingly engages a threaded aperture 34 defined by a boss extending rearward from front portion 12, such that as control member 16 rotates, front portion 12 moves relative to control member 16 (e.g., control member 16 moves into or out of the threaded boss of front portion 12). As such, control member 16 is contained entirely within the periphery of front and rear portions 12, 14. The control member 16 may in some embodiments be configured to be flush with the outer sides of front and rear portions 12, 14. In other embodiments, the control member 16 is recessed within front and/or rear portions 12, 14. For example, as shown in FIG. 14, front portion 12 has a solid, bull-nose configuration such that control member 16 is concealed therein. In various embodiments, the implants include grooves that may help secure the implant in the body of a patient, by providing spaces for structures in the body of a patient to engage the grooves.

Referring now to FIGS. 31-38, an implant 210 is shown according to an exemplary embodiment. Implant 210 is usable, for example, between and/or within vertebral bodies of the spine, and may share many of the features of the other inter/intra-body implants discussed elsewhere herein. It should be understood that implant 210 may in some embodiments be usable in other portions of the body in addition to the spine, and all such applications are to be understood to be within the scope of the present disclosure. Implant 210 is generally similar to implants 10 and 110 in structure and function except with respect to the additional access port features discussed below. As such, implant 210 is understood to include any or all of the features of implants 10 and 110 to the extent consistent with the additional features of implant 210 described herein (e.g., retention pins, dovetail projections and ramped surfaces, alignment features, etc.).

According to an exemplary embodiment, implant 210 includes a first, or front portion 212, a second, or rear portion 214, and a third, intermediate, or control member or portion 216, which collectively form a body or control assembly that extends along a longitudinal axis of implant 210. A first, or upper support 218 (e.g., an upper plate or support member, etc.) and a second, lower support 220 (e.g., a lower plate or support member), are coupled to the body assembly and may extend generally between front and rear portions 212, 214. According to an exemplary embodiment, first and second supports 218, 220 define a height of implant 210 extending between the outer or top surface of first support 218 and the outer or lower surface of second support 220.

In one embodiment, control member 216 includes a head portion 230, a collar recess 232, a threaded portion 234, a tool recess 236, and access ports 238. Threaded portion 234 and the non-threaded portion of control member 216 including access ports 238 collectively form a body portion for control member 216. Head portion 230 is received within a counterbore in rear portion 214. Collar recess 232 is configured to enable placement of collar 224 into a position to retain head portion 230 within the counterbore in rear portion 214. Threaded portion 234 is configured to threadingly engage a threaded aperture provided by front portion 212. Tool recess 236 is formed in the rearward portion of head portion 230 and communicates with access ports 238, which extend to opposite sides of control member 216. Tool recess 236 is configured to receive a tool to enable threading manipulation of control member 216. Tool recess 236 and access ports 238 are collectively configured to provide a fluid path to an interior of implant 210 and enable delivery of fluid, bone growth material, or other material to an interior of implant 210.

As shown in FIGS. 35-38, in one embodiment, two access ports 238 are in communication with tool recess 236 and extend to opposite sides of control member 216. In other embodiments, more or fewer access ports 238 may be utilized, and the size and shape of the individual access ports 238 may be varied to suit a particular application, size of implant, and the like. Access ports 238 are positioned to provide fluid communication with an interior area of implant 210.

Referring to FIGS. 39-46, an implant 260 is shown according to an exemplary embodiment. Implant 260 is usable, for example, between and/or within vertebral bodies of the spine, and may share many of the features of the other inter/intra-body implants discussed elsewhere herein. It should be understood that implant 260 may in some embodiments be usable in other portions of the body in addition to the spine, and all such applications are to be understood to be within the scope of the present disclosure. Implant 260 is generally similar to implants 10, 110, and 210 (and the other implants described herein) in structure and function except with respect to the additional conical projection, side bone graft window, and elongated component features discussed below. As such, implant 260 is understood to include any or all of the features of the other implants described herein to the extent consistent with the additional features of implant 260 described herein (e.g., retention pins, dovetail projections and ramped surfaces, alignment features, control member access port(s), etc.).

According to an exemplary embodiment, implant 260 includes a first, or front portion 262, a second, or rear portion 264, and a third, intermediate, or control member or portion 266, which collectively form a body or control assembly that extends along a longitudinal axis of implant 260. A first, or upper support 268 (e.g., an upper plate or support member, etc.) and a second, lower support 270 (e.g., a lower plate or support member), are coupled to the body assembly and may extend generally between front and rear portions 262, 264. According to an exemplary embodiment, first and second supports 268, 270 define a height of implant 260 extending between the outer or top surface of first support 268 and the outer or lower surface of second support 270.

In one embodiment, control member 266 includes a head portion 280, a collar recess 282, a threaded portion 284, a tool recess 286, and access ports 288. Head portion 280 is received within a counterbore in rear portion 264. Collar recess 282 is configured to enable placement of collar 274 into a position to retain head portion 280 within the counterbore of rear portion 264. Threaded portion 284 is configured to threadingly engage a threaded aperture provided by front portion 262. Tool recess 286 is formed in the rearward portion of head portion 280 and communicates with access ports 288, which extend to opposite sides of control member 266. Tool recess 286 is configured to receive a tool to enable threading manipulation of control member 266. Tool recess 286 and access ports 288 are collectively configured to provide a fluid path to an interior of implant 260 and enable delivery of fluid, bone growth material, or other material to an interior of implant 260.

Figure 45:
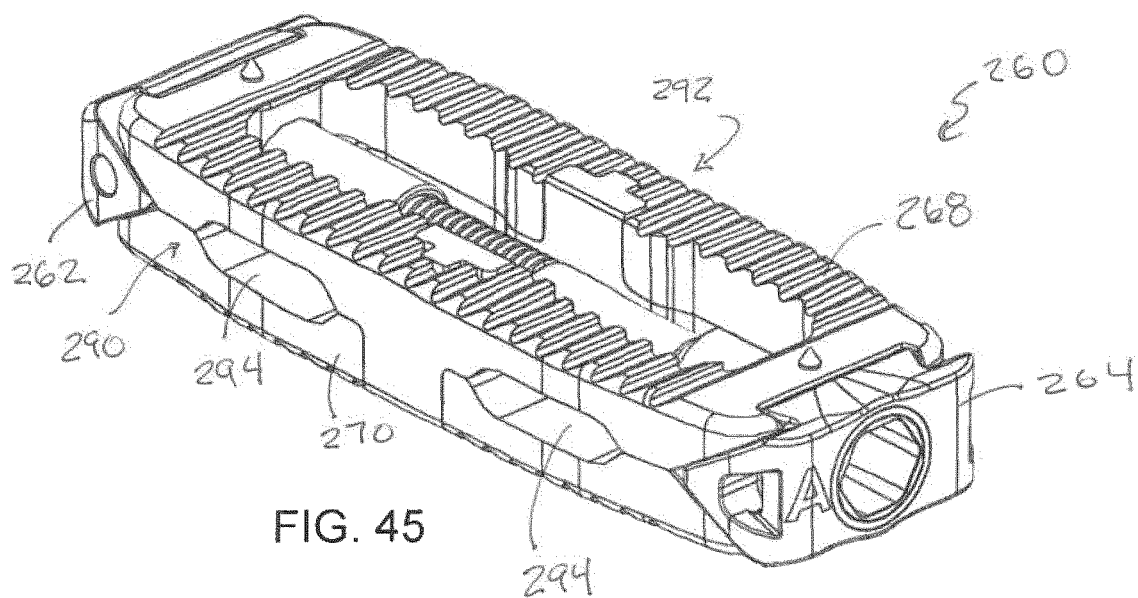
Figure 46:
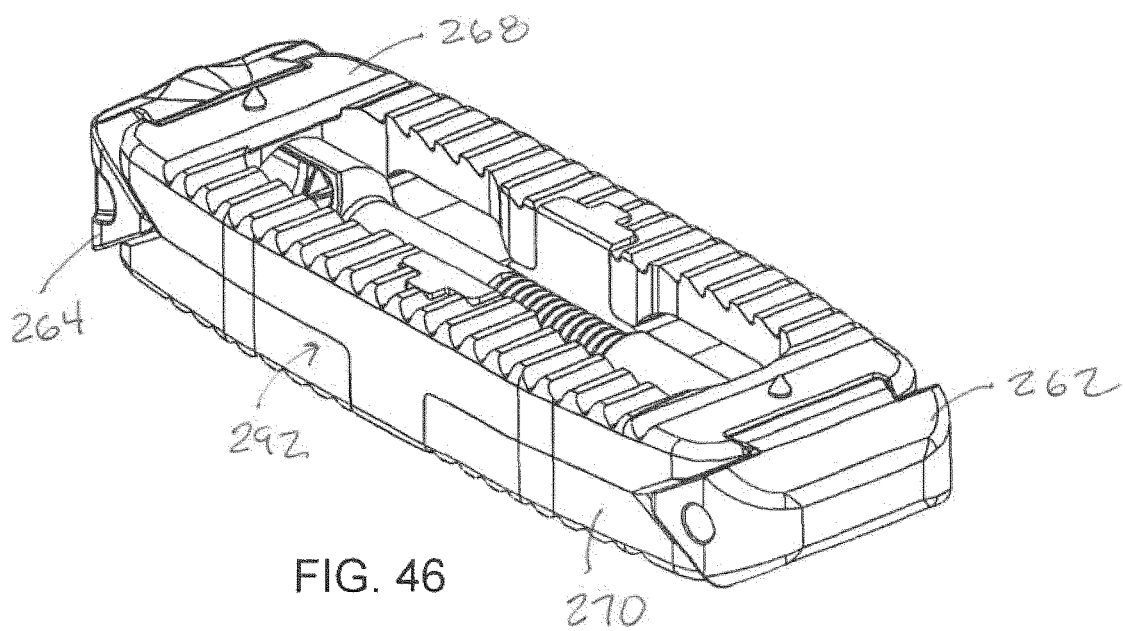

Referring to FIGS. 45-46, in one embodiment implant 260 defines a first side 290 and a second, opposite side 292. First and second sides 290, 292 are generally formed by the sidewalls of top and bottom supports 268, 270. In one embodiment, one or both of first and second sides 290, 292 include side bone graft apertures or windows. For example, as shown in FIG. 45, in some embodiments, first side 290 includes side apertures 294 and second side 292 forms a generally solid sidewall. While FIG. 45 illustrates first side 290 as including two bone graft apertures 294, according to various alternative embodiments, one or both of first side 290 and second side 292 may include more or fewer side apertures. In some embodiments, one or both of top and bottom supports 268, 270 may include a projection 296 (e.g., a conical projection) at one or both ends. Projections 296 may extend above the other portions of top and bottom supports 268, 270 (e.g., teeth, etc.)

Figure 42:
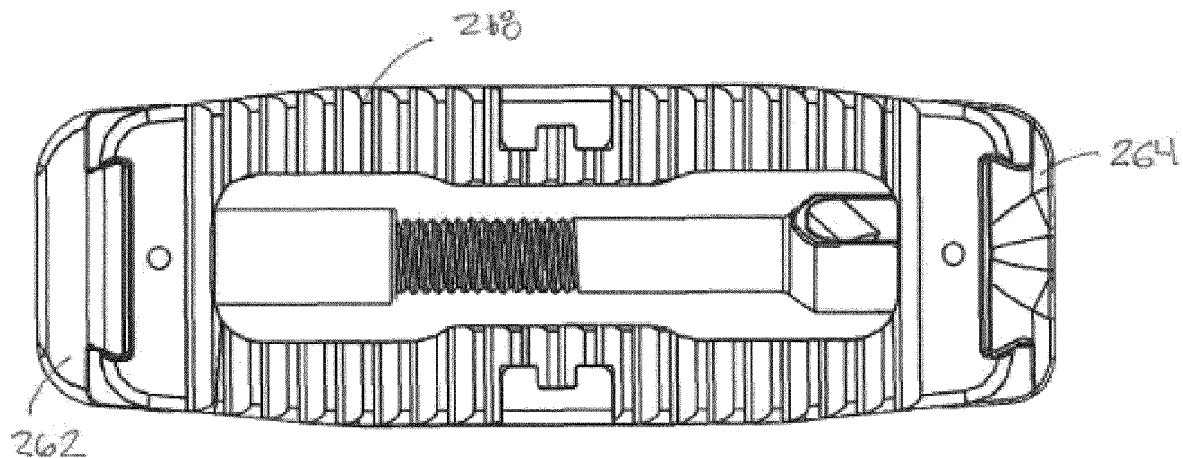
Figure 43:
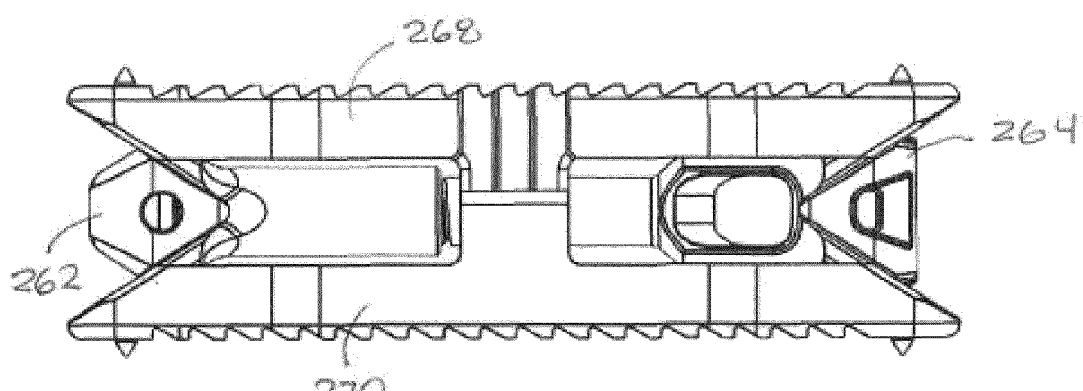
Figure 44:
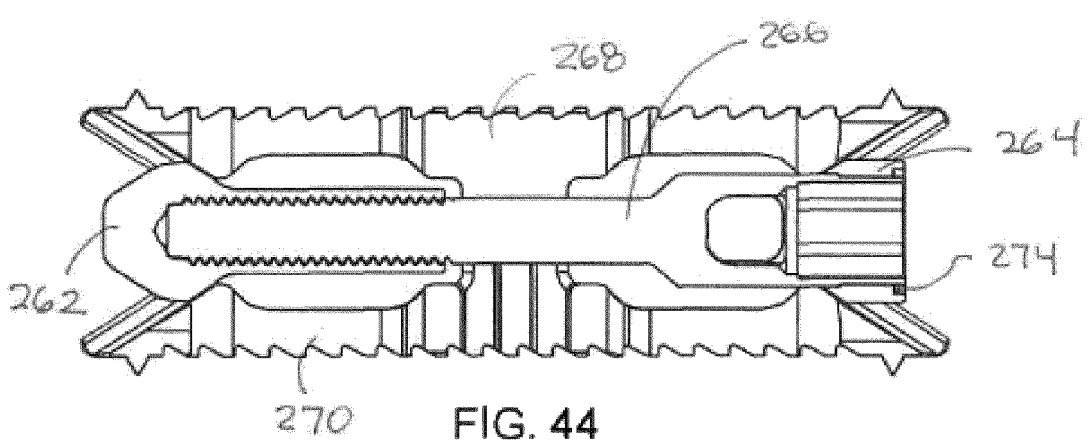

In some embodiments, top and bottom supports 268, 270 have a generally symmetric profile about control member 266, as shown for example, in FIG. 42. Implant 260 may further be elongated relative to other implants illustrated herein, having an overall length to overall width ratio (in the collapsed configuration) of 2, 3, 4, or more (or another ratio, such as a range of between 2 and 5, between 2 and 4, etc.).

Figure 47:
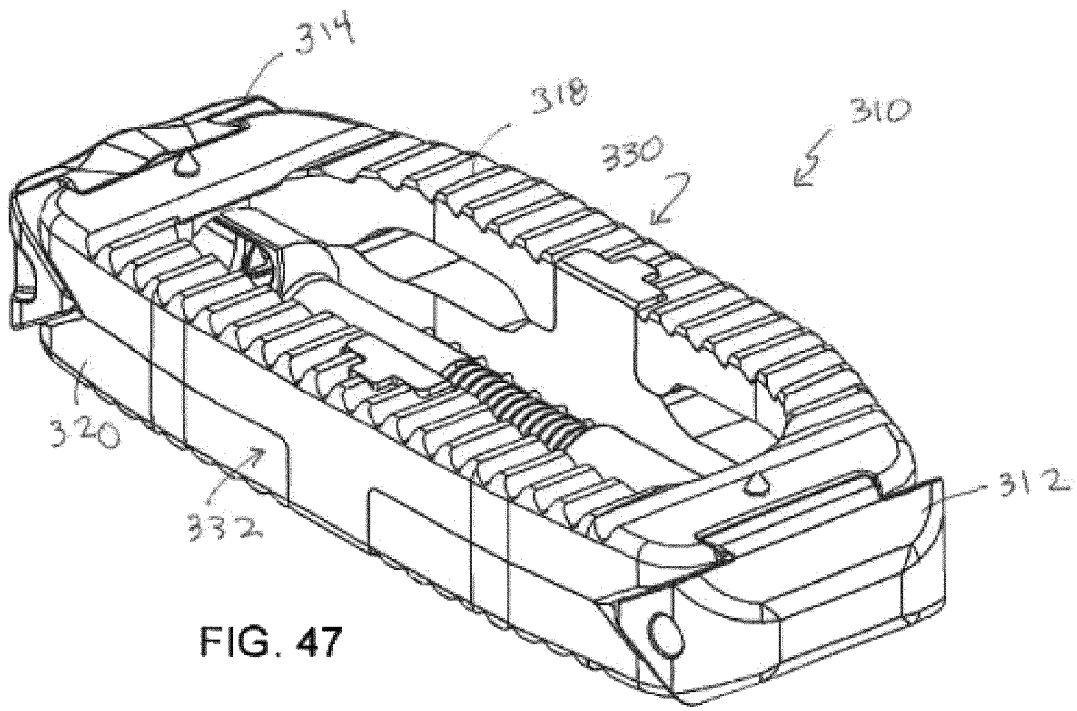
FIGS. 47-49 show various views of an expandable implant according to an alternative embodiment.
Figure 48:
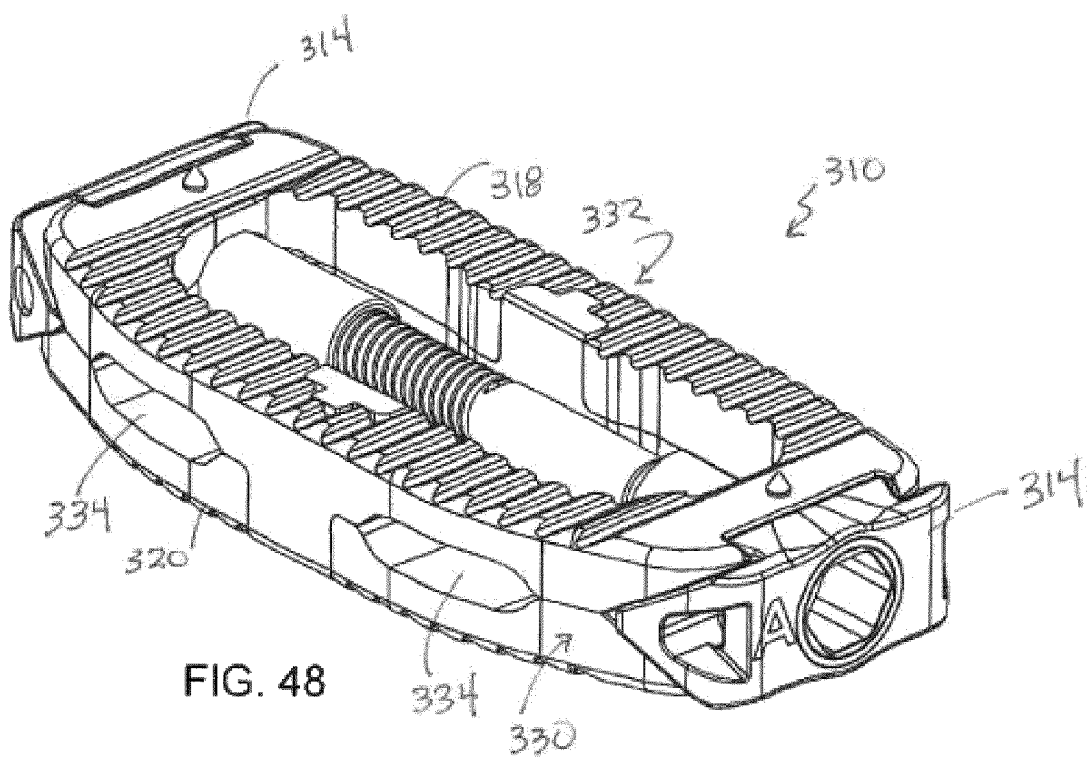
Figure 49:
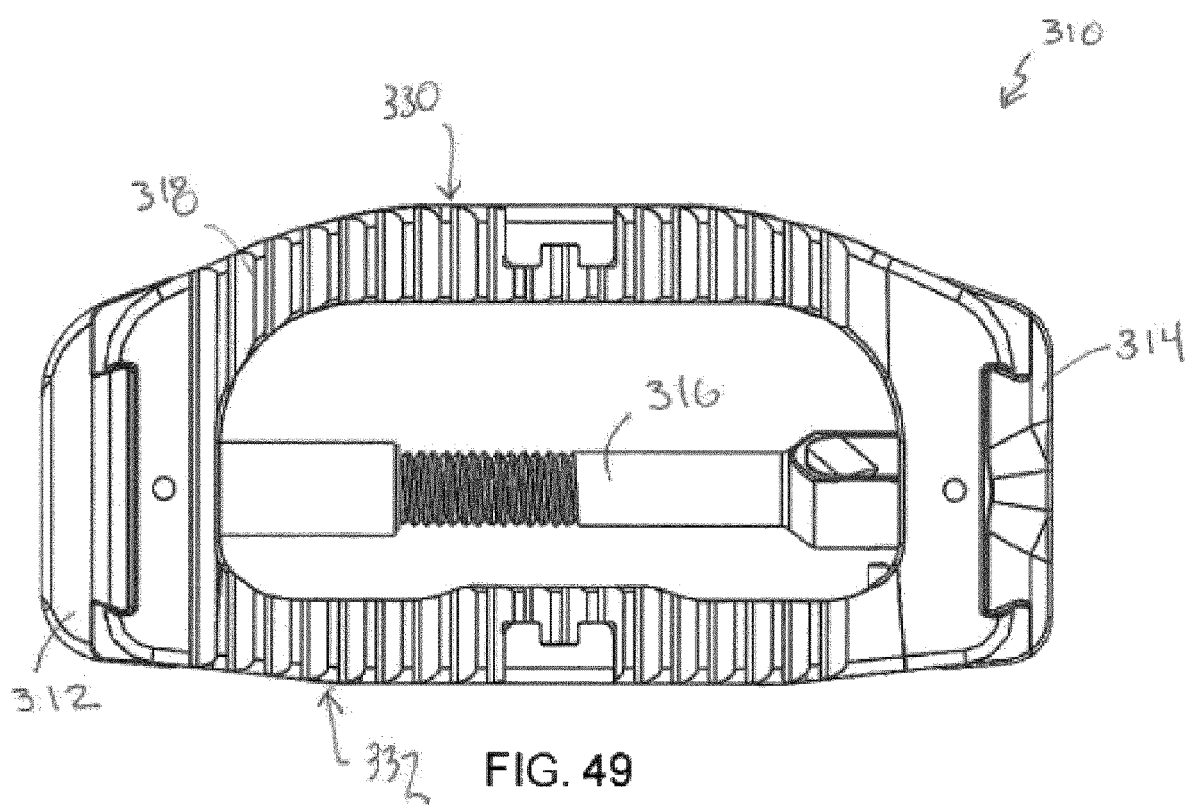

Referring to FIGS. 47-49, an implant 310 is shown according to an exemplary embodiment. Implant 310 is usable, for example, between and/or within vertebral bodies of the spine, and may share many of the features of the other inter/intra-body implants discussed elsewhere herein. It should be understood that implant 310 may in some embodiments be usable in other portions of the body in addition to the spine, and all such applications are to be understood to be within the scope of the present disclosure. Implant 310 is generally similar to implants 260 (and the other implants described herein) in structure and function except with respect to the additional asymmetric component features discussed below. As such, implant 310 is understood to include any or all of the features of the other implants described herein to the extent consistent with the additional features of implant 310 described herein (e.g., retention pins, dovetail projections and ramped surfaces, alignment features, control member access port(s), etc.).

According to an exemplary embodiment, implant 310 includes a first, or front portion 312, a second, or rear portion 314, and a third, intermediate, or control member or portion 316, which collectively form a body or control assembly that extends along a longitudinal axis of implant 310. A first, or upper support 318 (e.g., an upper plate or support member, etc.) and a second, lower support 320 (e.g., a lower plate or support member), are coupled to the body assembly and may extend generally between front and rear portions 312, 314. According to an exemplary embodiment, first and second supports 318, 320 define a height of implant 310 extending between the outer or top surface of first support 318 and the outer or lower surface of second support 320.

In one embodiment, implant 310 defines a first side portion 330 and a second side portion 332. In one embodiment, one or both of first and second side portions 330, 332 include side bone graft apertures or windows. For example, as shown in FIG. 48, in some embodiments, first side 330 includes side apertures 334. While FIG. 48 illustrates first side 330 as including two bone graft apertures 334, according to various alternative embodiments, one or both of first side 330 and second side 332 may include more or fewer side apertures.

In some embodiments, first side portion 330 and second side portion 332 provide an asymmetric profile about control member 316, as shown for example in FIG. 49. In some embodiments, a portion of first side portion 330 extends away from control member 316 a further distance than the corresponding portions of second side portion 332, forming an asymmetric shape (e.g., a "D" or similar shape). Providing an asymmetric profile may provide benefits in particular applications where additional support is desired and/or when placement of implant 310 is difficult. While FIGS. 47-49 shown implant 310 having a general "D" asymmetric shape, according to various alternative embodiments, other asymmetric shapes and configurations may be utilized.

Referring to FIGS. 50-53, an implant 360 is shown according to an exemplary embodiment. Implant 360 is usable, for example, between and/or within vertebral bodies of the spine, and may share many of the features of the other inter/intra-body implants discussed elsewhere herein. It should be understood that implant 360 may in some embodiments be usable in other portions of the body in addition to the spine, and all such applications are to be understood to be within the scope of the present disclosure. Implant 360 is generally similar to implants 260 and 310 (and the other implants described herein) in structure and function except with respect to the additional lateral taper features discussed below. As such, implant 360 is understood to include any or all of the features of the other implants described herein to the extent consistent with the additional features of implant 360 described herein (e.g., retention pins, dovetail projections and ramped surfaces, alignment features, control member access port(s), etc.).

According to an exemplary embodiment, implant 360 includes a first, or front portion 362, a second, or rear portion 364, and a third, intermediate, or control member or portion 366, which collectively form a body or control assembly that extends along a longitudinal axis of implant 360. A first, or upper support 368 (e.g., an upper plate or support member, etc.) and a second, lower support 370 (e.g., a lower plate or support member), are coupled to the body or control assembly and may extend generally between front and rear portions 362, 364. According to an exemplary embodiment, first and second supports 368, 370 define a height of implant 360 extending between the outer or top surface of first support 368 and the outer or lower surface of second support 370. As discuss in greater detail below, the height of implant 360 decreases in a lateral direction.

Figure 50:
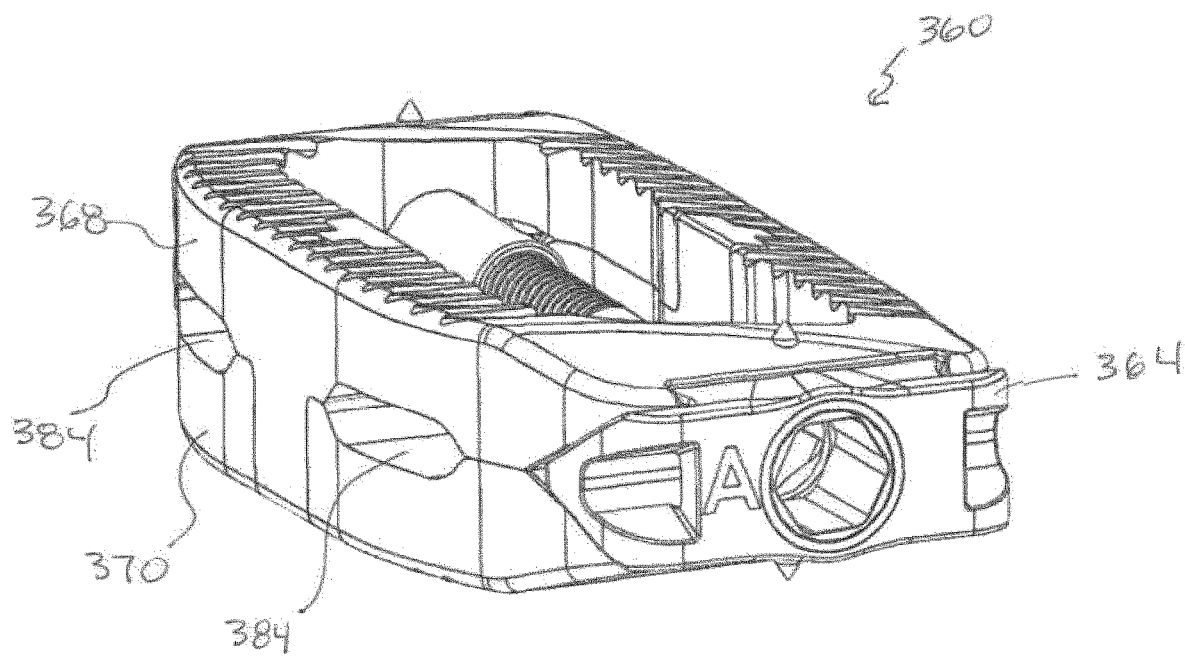
FIGS. 50-53 show various views of an expandable implant according to an alternative embodiment.

In one embodiment, implant 360 defines a first side portion 380 and a second side portion 382. In one embodiment, one or both of first and second side portions 380, 382 include side bone graft apertures or windows. For example, as shown in FIG. 50, in some embodiments, second side 382 includes side apertures 384. While FIG. 50 illustrates second side 382 as including two bone graft apertures 384, according to various alternative embodiments, one or both of first side 380 and second side 382 may include more or fewer side apertures.

Figure 51:
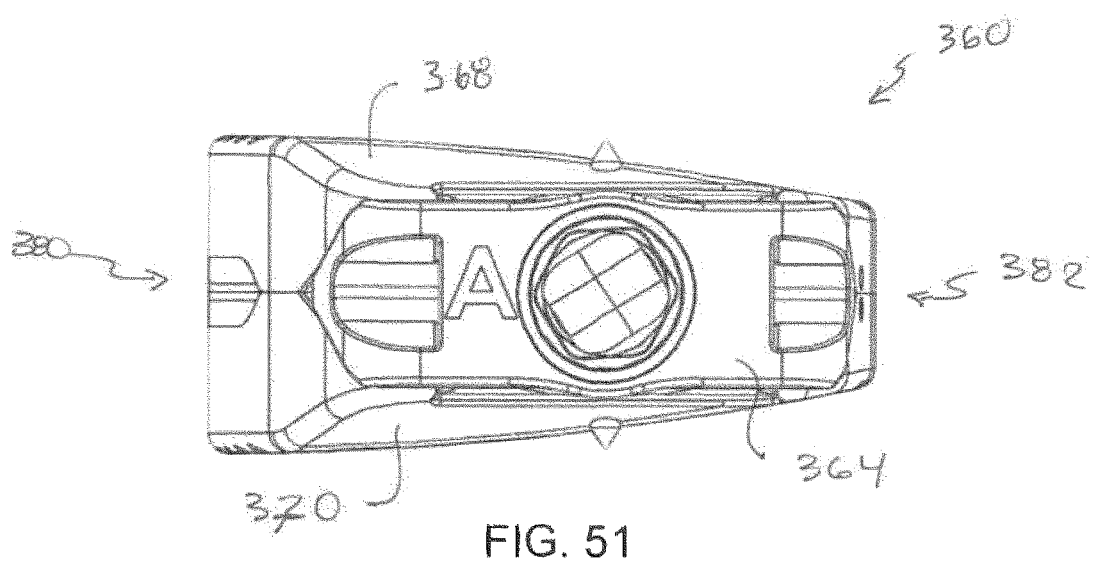
Figure 52:
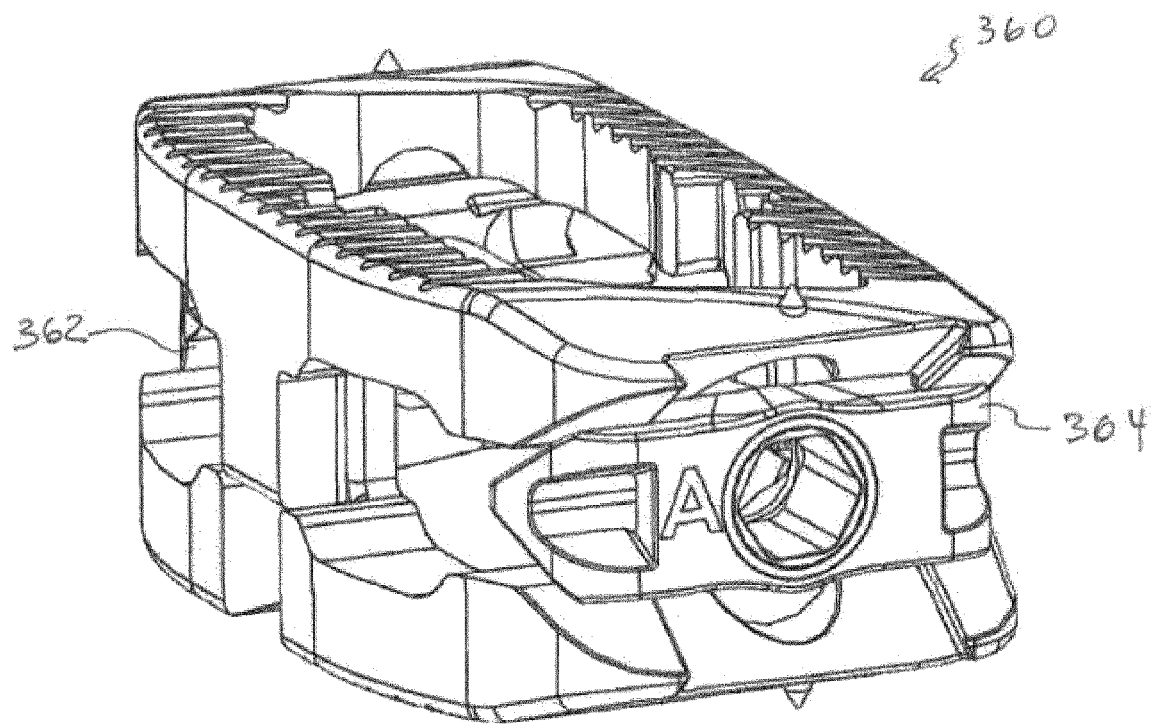
Figure 53:
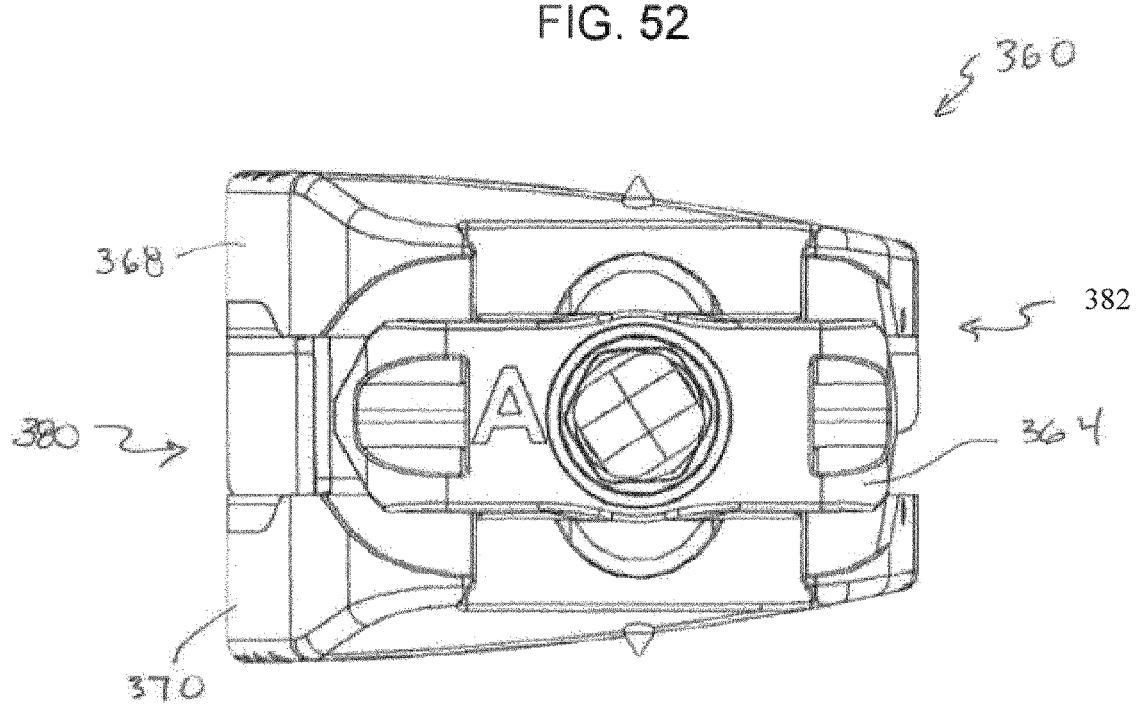
Figure 54:
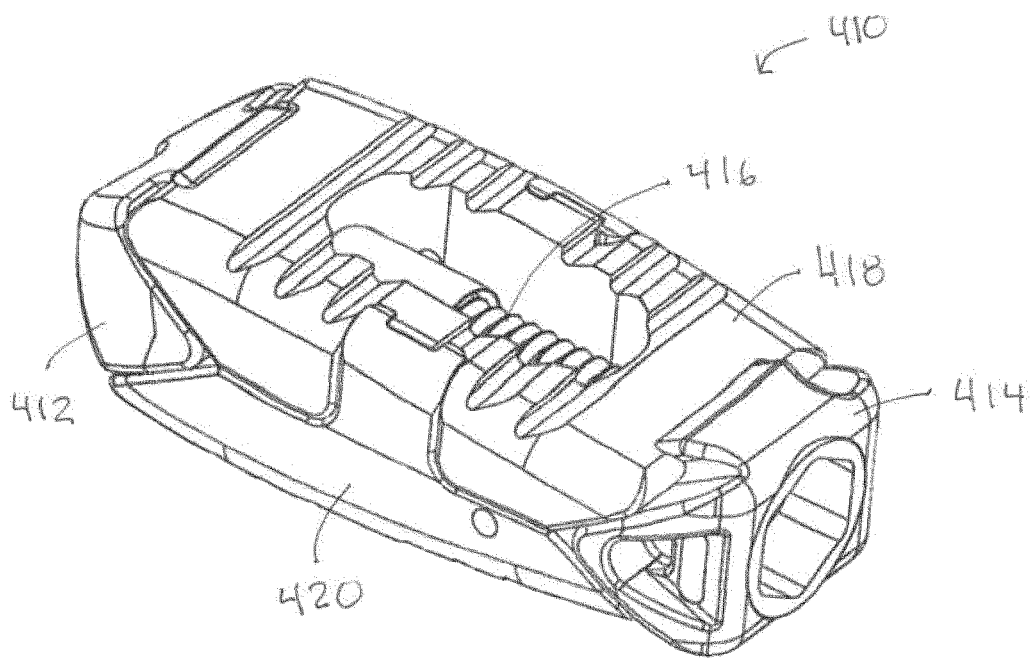
FIGS. 54-65 show various views of an expandable implant according to an alternative embodiment.
Figure 55:
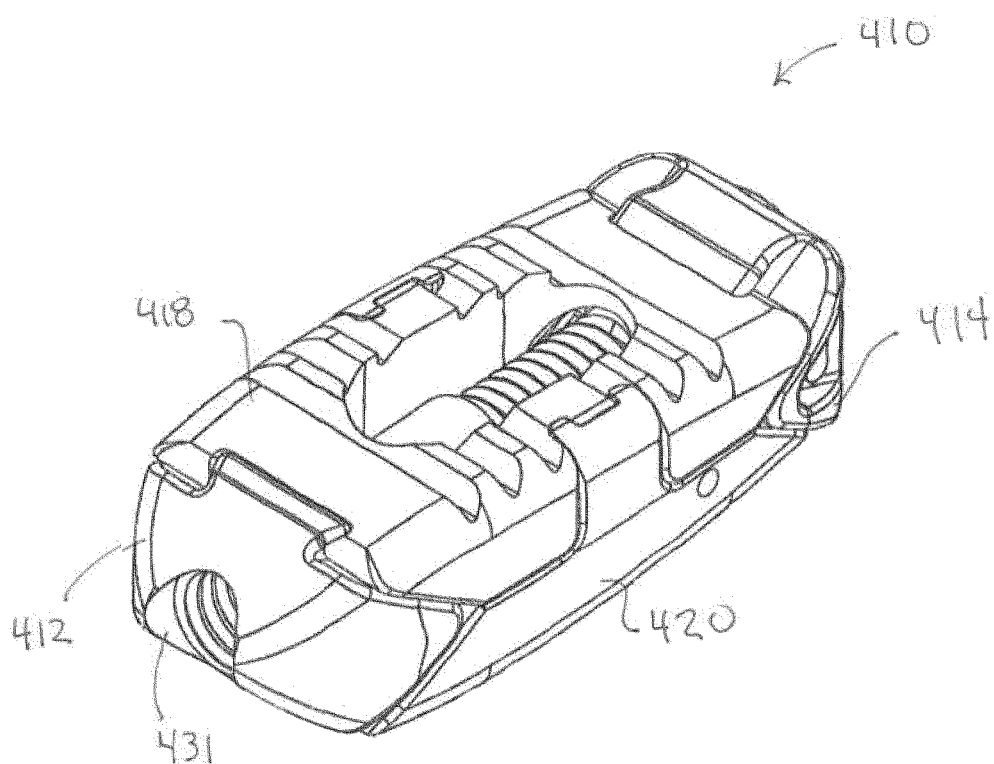
Figure 56:
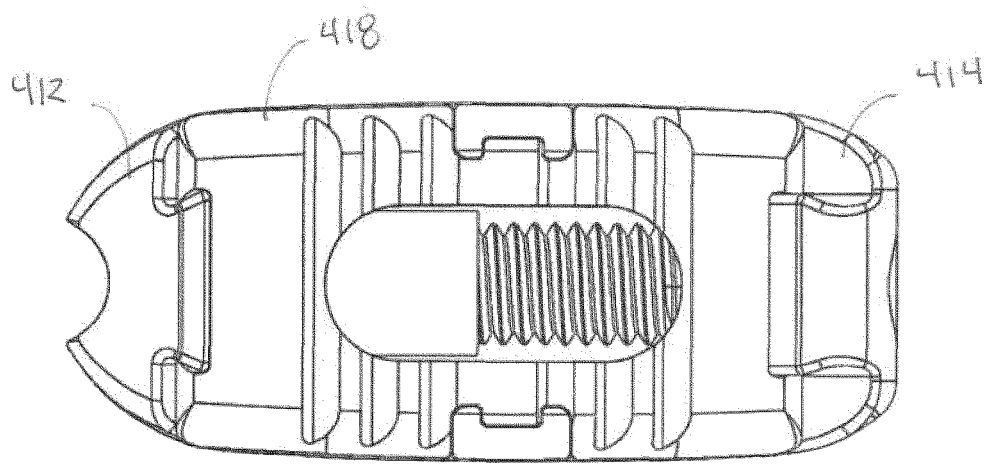

In one embodiment, implant 360 is configured to provide a predetermined lateral taper that remains constant as implant 360 is moved between a collapsed configuration (see FIGS. 50-51) and an expanded configuration (see FIGS. 52-53). For example, referring to FIG. 51, in a collapsed configuration, a first lateral side such as side 380 may have a first height that is larger than a height of second lateral side 382. The degree of taper between the first and second lateral sides 380, 382 may be adjusted to suit a particular embodiment (e.g., a desired spinal curvature). As such, both the top and bottom supports 368, 370 may include outer surfaces (e.g. top and bottom surfaces) that define a lateral angular offset from a parallel configuration (e.g., a configuration where the top and bottom supports 368, 370 are generally parallel).

As shown in FIGS. 51 and 53, top and bottom supports 368 and 370 move toward and away from each other in a linear manner, such that the degree of taper remains constant. In other embodiments, other configurations may be utilized to provide non-linear movement and a varying lateral taper. Furthermore, while FIGS. 50-53 illustrate an implant having a constant lateral taper, according to various alternative embodiments, implants may be provided having a variable longitudinal taper.

Referring to FIGS. 54-65, an implant 410 is shown according to an exemplary embodiment. Implant 410 is usable, for example, between and/or within vertebral bodies of the spine, and may share many of the features of the other inter/intra-body implants discussed elsewhere herein. It should be understood that implant 410 may in some embodiments be usable in other portions of the body in addition to the spine, and all such applications are to be understood to be within the scope of the present disclosure. Implant 410 is generally similar to implants 260 and 310 (and the other implants described herein) in structure and function except with respect to the additional longitudinal taper features discussed below. As such, implant 410 is understood to include any or all of the features of the other implants described herein to the extent consistent with the additional features of implant 410 described herein (e.g., retention pins, dovetail projections and ramped surfaces, alignment features, control member access port(s), etc.).

According to an exemplary embodiment, implant 410 includes a first, or front portion 412, a second, or rear portion 414, and a third, intermediate, or control member or portion 416, which collectively form a body or control assembly that extends along a longitudinal axis of implant 410. In some embodiments, front portion 412 includes a through hole 431 configured to enable control member 416 to extend through front portion 412. A first, or upper support 418 (e.g., an upper plate or support member, etc.) and a second, lower support 420 (e.g., a lower plate or support member), are coupled to the body or control assembly and may extend generally between front and rear portions 412, 414. According to an exemplary embodiment, first and second supports 418, 420 define a height of implant 410 extending between the outer or top surface of first support 418 and the outer or lower surface of second support 420. As discussed in greater detail below, the height of implant 410 decreases in a longitudinal direction (e.g., to provide a longitudinal taper feature).

Figure 57:
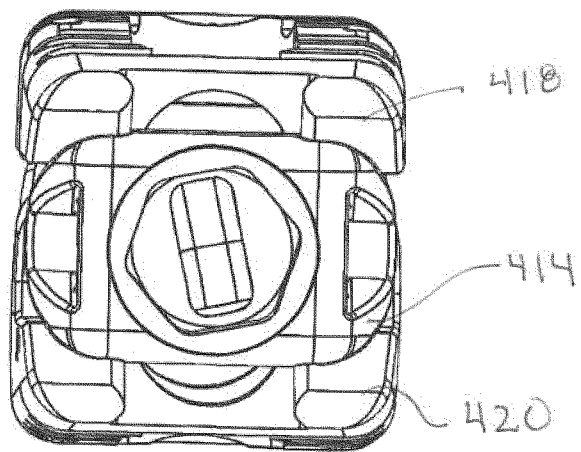
Figure 58:
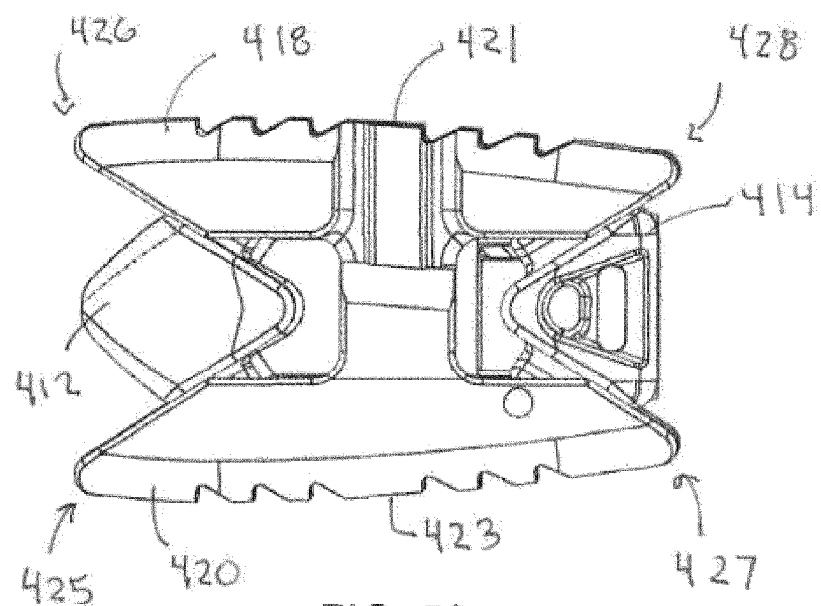
Figure 59:
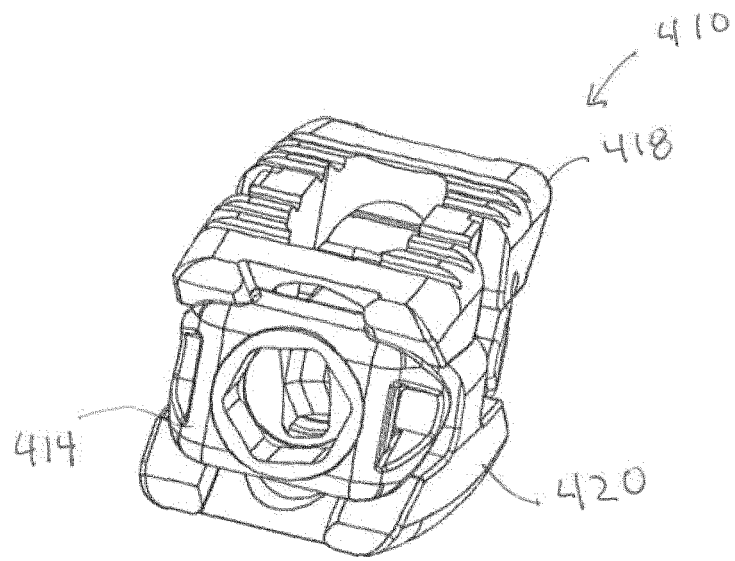
Figure 60:
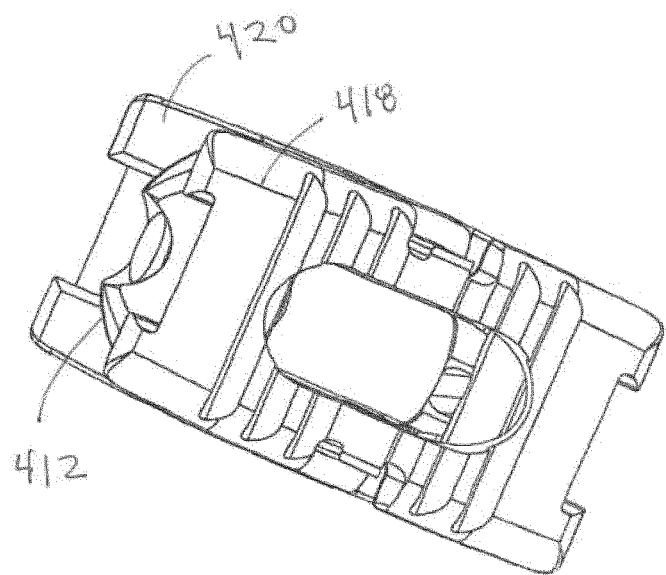

In one embodiment, implant 410 is configured to provide a predetermined longitudinal taper that remains constant as implant 410 is moved between a collapsed configuration (see FIGS. 54-55) and an expanded configuration (see FIGS. 57-58). As such, both the top and bottom supports 418, 420 may include outer surfaces (e.g. top and bottom surfaces) that define a lateral angular offset from a parallel configuration (e.g., a configuration where the top and bottom supports 418, 420 are generally parallel).

In some embodiments, implant 410 defines a longitudinal axis extending along control member 416. Top support 418 defines a first end 426, a second end 428, and a top surface 421 extending between first and second ends 426, 428. First and second ends 426, 428 define an overall taper to top surface 421. In some embodiments, top surface 421 may define an arcuate shape between first end 426 and second end 428 (e.g., such that top surface 421 has a slight curvature between first and second ends 426, 428). In other embodiments, top surface 421 may define a substantially planar surface between first and second ends 426, 428. Bottom support 420 defines a first end 425, a second end 427, and a bottom surface 423 extending between first and second ends 425, 427. First and second ends 425, 427 define an overall taper to top surface 423. In some embodiments, top surface 423 may define an arcuate shape between first end 425 and second end 427 (e.g., such that top surface 423 has a slight curvature between first and second ends 425, 427). In other embodiments, top surface 423 may define a substantially planar surface between first and second ends 425, 427.

As shown in FIGS. 54-58, top and bottom supports 418 and 420 move toward and away from each other in a linear manner, such that the degree of taper remains constant. In other embodiment, other configurations may be utilized to provide non-linear movement and a varying longitudinal taper. Furthermore, while FIGS. 54-58 illustrate an implant having a constant longitudinal taper, according to various alternative embodiments, implants may be provided having a variable longitudinal taper.

Figure 61:
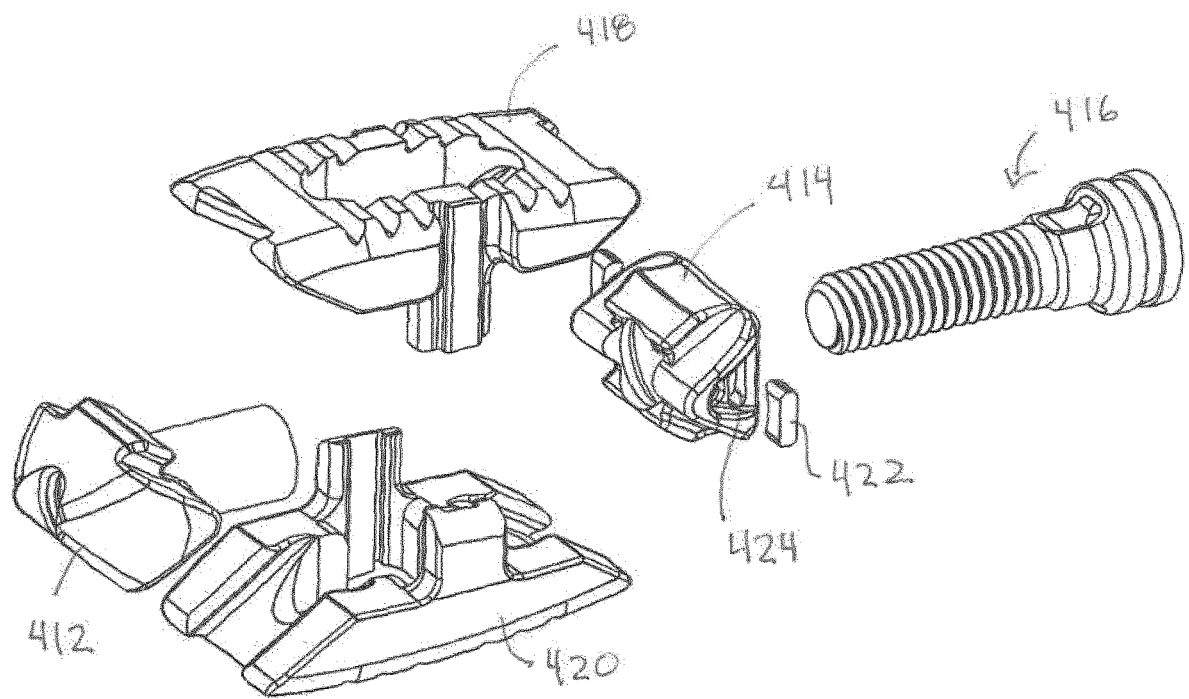
Figure 62:
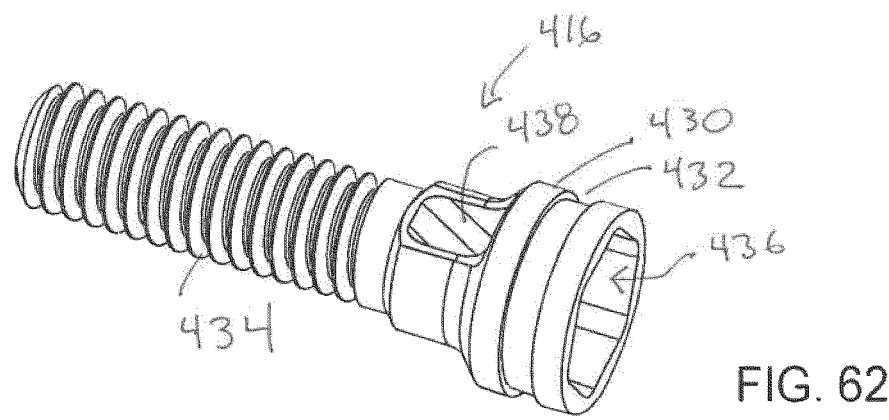
Figure 63:
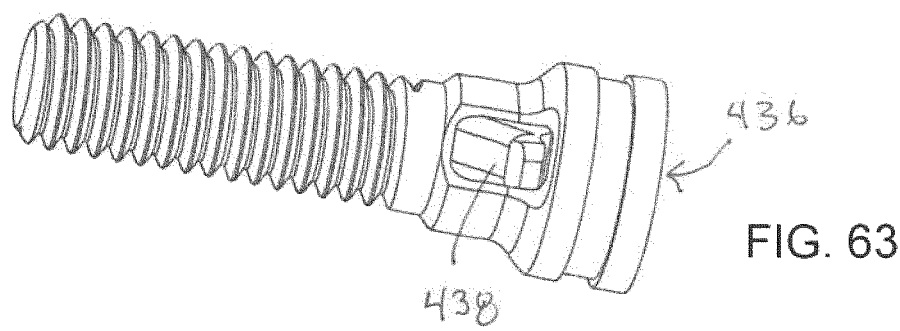
Figure 64:
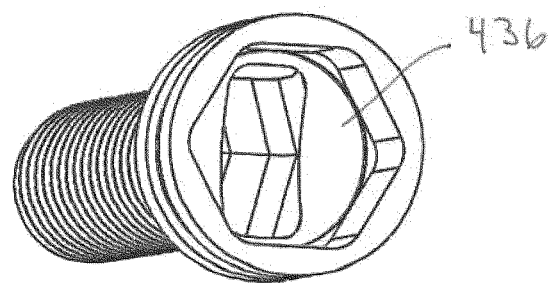
Figure 65:
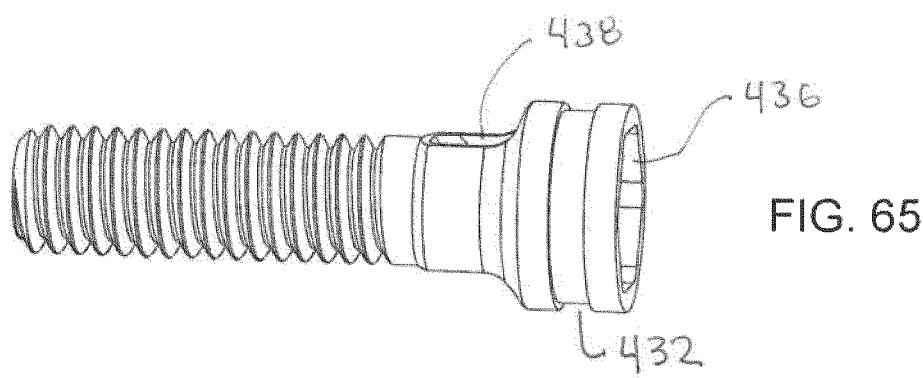
Figure 66:
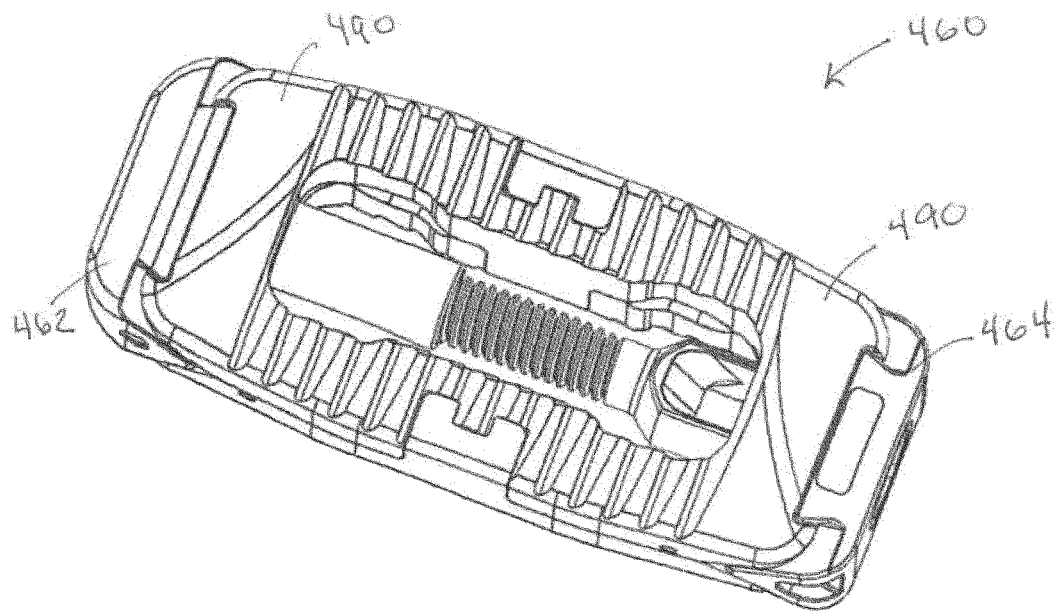
FIGS. 66-70 show various views of an expandable implant according to an alternative embodiment.
Figure 67:
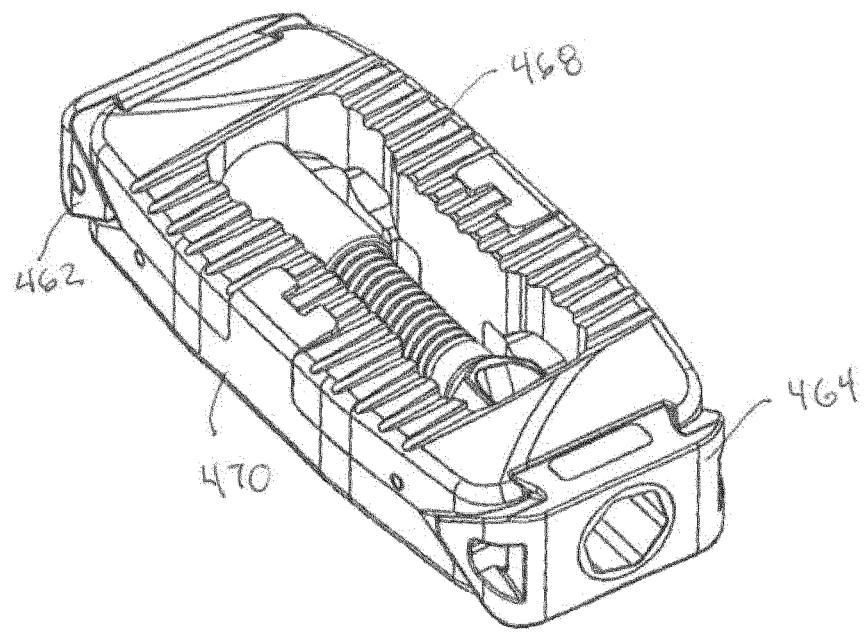
Figure 68:
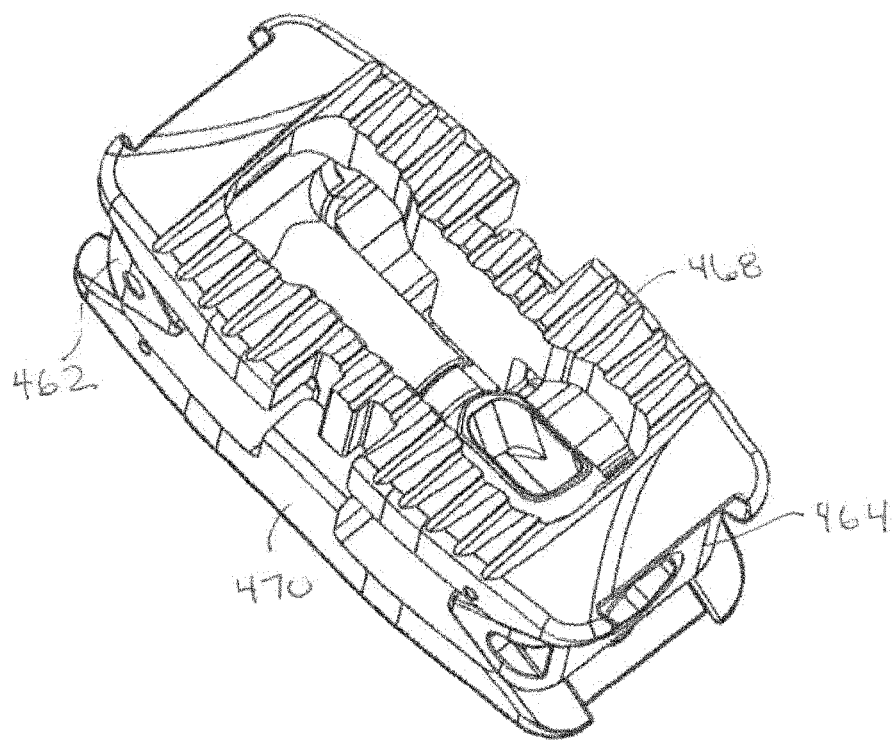

Referring to FIGS. 61-65, in some embodiments, implant 410 includes one or more retaining members to retain control member 416 in a desired longitudinal position. For example, as shown in FIG. 61, in one embodiment, implant 410 includes retaining members 422 received in side apertures 424 on opposing sides of rear support 414. Control member 416 includes a head portion 430, a groove 432, and a threaded portion 434. Control member 416 further includes a tool recess 436 in fluid communication with access ports 438. Retaining members 422 are configured to extend through rear support 414 and be received within groove 432 of control member 416, such that control member 416 is longitudinally fixed relative to rear support 414, but also rotatable relative to rear support 414. FIG. 61 illustrates retaining members 422 extending into rear support 414 from opposing lateral sides. In various alternative embodiments, retaining members may be used that extend through other portions, such as opposing top and bottom sides.

For example, referring to FIGS. 66-70, an implant 460 is shown according to an exemplary embodiment. Implant 460 is usable, for example, between and/or within vertebral bodies of the spine, and may share many of the features of the other inter/intra-body implants discussed elsewhere herein. It should be understood that implant 460 may in some embodiments be usable in other portions of the body in addition to the spine, and all such applications are to be understood to be within the scope of the present disclosure. Implant 460 is generally similar to the other implants described herein in structure and function except with respect to the additional retaining member features discussed below. As such, implant 460 is understood to include any or all of the features of the other implants described herein to the extent consistent with the additional features of implant 460 described herein (e.g., retention pins, dovetail projections and ramped surfaces, alignment features, control member access port(s), etc.).

According to an exemplary embodiment, implant 460 includes a first, or front portion 462, a second, or rear portion 464, and a third, intermediate, or control member or portion 466, which collectively form a body or control assembly that extends along a longitudinal axis of implant 460. A first, or upper support 468 (e.g., an upper plate or support member, etc.) and a second, lower support 470 (e.g., a lower plate or support member), are coupled to the body or control assembly and may extend generally between front and rear portions 462, 464. According to an exemplary embodiment, first and second supports 468, 470 define a height of implant 460 extending between the outer or top surface of first support 468 and the outer or lower surface of second support 470. In some embodiments, top and bottom supports 468, 470 may include tapered corner sections 490, 492 to facilitate insertion/removal of implant 460, etc.

Figure 70:
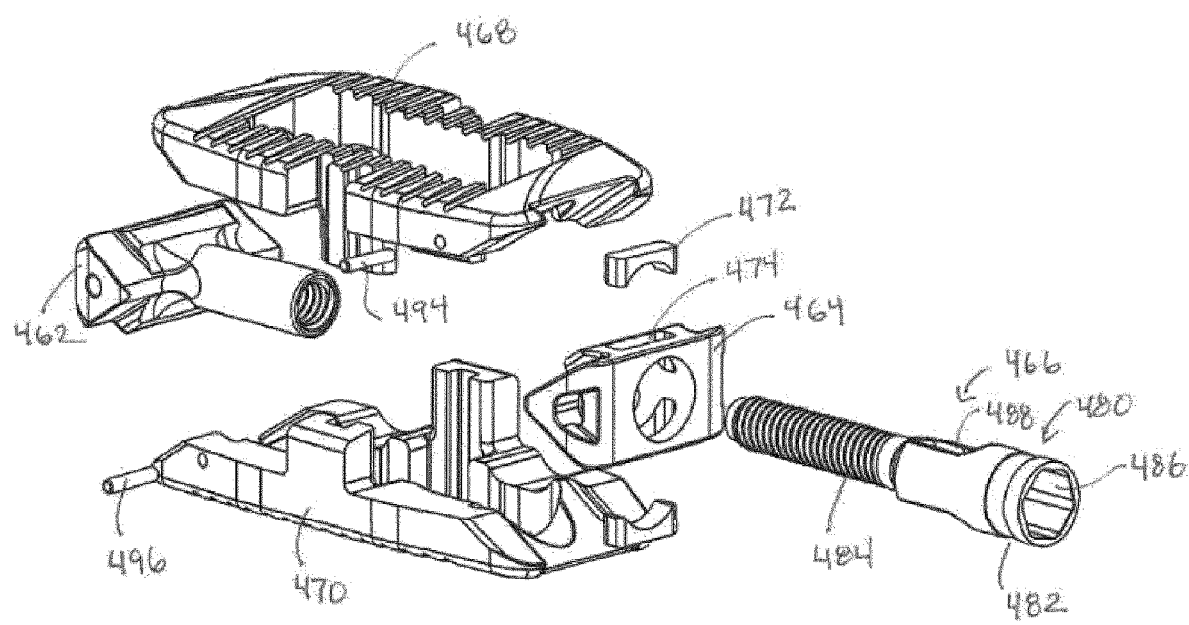

In one embodiment, top and bottom supports 468, 470 are retained by upper and lower pins 494, 496. In one embodiment, upper pins 494 extend through opposite sides of one end of top support 468, and lower pins 496 extend through opposite sides of an opposite end of bottom support 470. Pins 494, 496 act to limit expansion of implant 460 and prevent removal of top and bottom supports 468, 470 from front and rear portions 462, 464. As shown in FIG. 70, in one embodiment, two retaining pins extend into each side of implant 460. In other embodiments, other numbers of retaining pins may be used, as shown for example in various other embodiments herein.

Referring further to FIG. 70, in some embodiments, implant 460 includes one or more retaining members to retain control member 466 in a desired longitudinal position. For example, as shown in FIG. 70, in one embodiment, implant 460 includes retaining members 472 received in top and bottom apertures 474 on opposing top and bottom sides of rear support 464. Control member 466 includes a head portion 480, a groove 482, and a threaded portion 484. Control member 466 further includes a tool recess 486 in fluid communication with access ports 488. Retaining members 472 are configured to extend through rear support 464 and be received within groove 482 of control member 466, such that control member 466 is longitudinally fixed relative to rear support 464, but also rotatable relative to rear support 464. FIG. 70 illustrates retaining members 472 extending into rear support 464 from opposing top and bottom sides.

In various alternative embodiments, retaining members may be used that extend through other portions, such as opposing lateral sides (e.g., as discussed with respect to implant 410).

Referring now to FIGS. 71-75, an implant 510 is shown according to an exemplary embodiment. Implant 510 is usable, for example, between and/or within vertebral bodies of the spine, and may share many of the features of the other inter/intra-body implants discussed elsewhere herein. It should be understood that implant 510 may in some embodiments be usable in other portions of the body in addition to the spine, and all such applications are to be understood to be within the scope of the present disclosure. Implant 510 is generally similar to the other implants discussed herein in structure and function except with respect to the two-piece top and bottom support member features discussed below. As such, implant 510 is understood to include any or all of the features of the other implants described herein to the extent consistent with the additional features of implant 510 described herein.

According to an exemplary embodiment, implant 510 includes a first, or front portion 512, a second, or rear portion 514, and a third, intermediate, or control member or portion 516, which collectively form a body or control assembly that extends along a longitudinal axis of implant 510. A first, or upper support assembly 518 (e.g., an upper plate or support member, etc.) and a second, lower support assembly 520 (e.g., a lower plate or support member), are coupled to the control assembly and may extend generally between front and rear portions 512, 514. According to an exemplary embodiment, first and second support assemblies 518, 520 define a height of implant 520 extending between the outer or top surface of first support assembly 518 and the outer or lower surface of second support assembly 520.

Front portion 512 includes ramped surfaces 562 and a threaded bore 564. Rear portion 514 includes dovetailed projections 566 and recess or aperture 568. Ramped surfaces 562 and dovetailed projections 566 facilitate controlled expansion and contraction of top support assembly 518 and bottom support assembly 520 relative to one another.

In one embodiment, top support assembly 518 includes a first portion 522 and a second portion 524 pivotally coupled to first portion 522 by way of a top pivot pin 530. First portion 522 defines an extension portion 532 that at least partially extends into a recess 534 in second portion 524. Top guide pins 526 extend through second portion 524 and into upper slots 528 in first portion 522 to limit the range of pivotal motion of first portion 522 relative to second portion 524 about top pivot pin 530. First portion 522 includes a ramped surface 536, and second portion 524 includes a dovetailed recess 538. Ramped surface 536 slidingly interfaces with a corresponding ramped surface 562 on front portion 512, and dovetailed recess 538 slidingly interfaces with a dovetailed projection 566 on rear portion 514.

In one embodiment, bottom support assembly 520 includes a first portion 542 and a second portion 544 pivotally coupled to first portion 542 by way of a bottom pivot pin 550. First portion 542 defines an extension portion 552 that at least partially extends into a recess 554 in second portion 524. Bottom guide pins 546 extend through second portion 544 and into bottom slots 548 in first portion 542 to limit the range of pivotal motion of first portion 542 relative to second portion 544 about bottom pivot pin 550. First portion 542 includes a ramped surface 556, and second portion 524 includes a dovetailed recess 558. Ramped surface 556 slidingly interfaces with a corresponding ramped surface 562 on front portion 512, and dovetailed recess 558 slidingly interfaces with a dovetailed projection 566 on rear portion 514.

In one embodiment, implant 510 includes alignment features configured to maintain proper alignment between at least a portion of top support assembly 518 and at least a portion of bottom support assembly 520. For example, an upper alignment guide 540 on second portion 524 of top support assembly 518 slidingly engages a correspondingly shaped lower alignment guide 560 on second portion 544 of bottom support assembly 520. As such, as first portions 522 and 542 angulate away from each other, second portions 524, 544 remain aligned (e.g., move in a linear fashion relative to one another).

Figure 71:
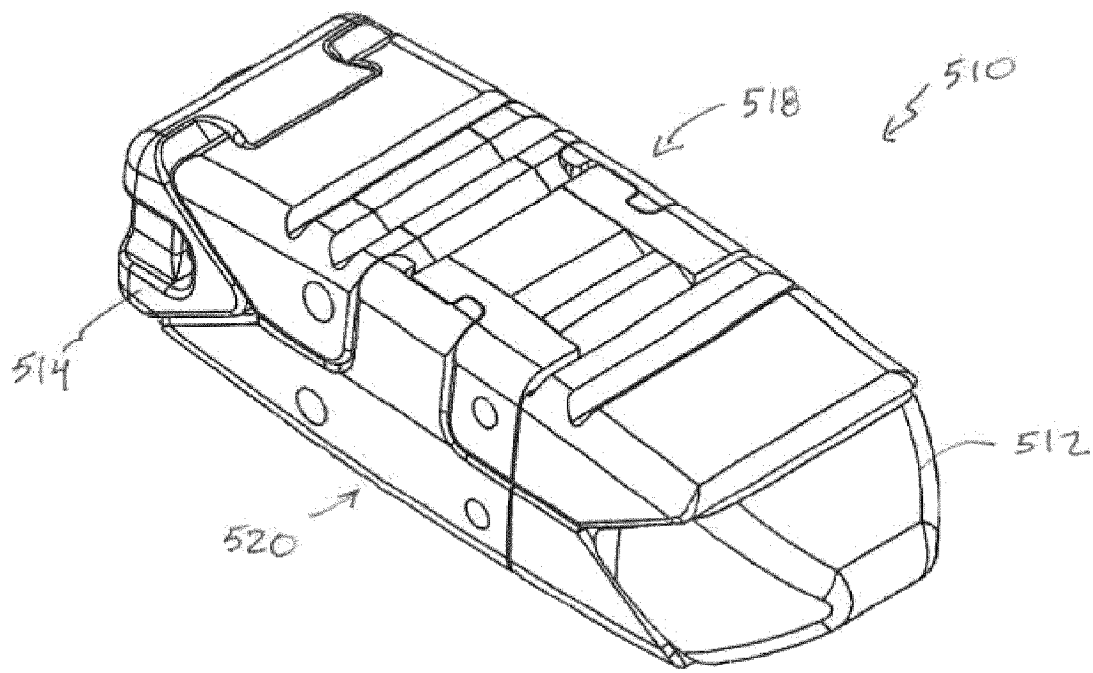
FIGS. 71-75 show various views of an expandable implant according to an alternative embodiment.
Figure 72:
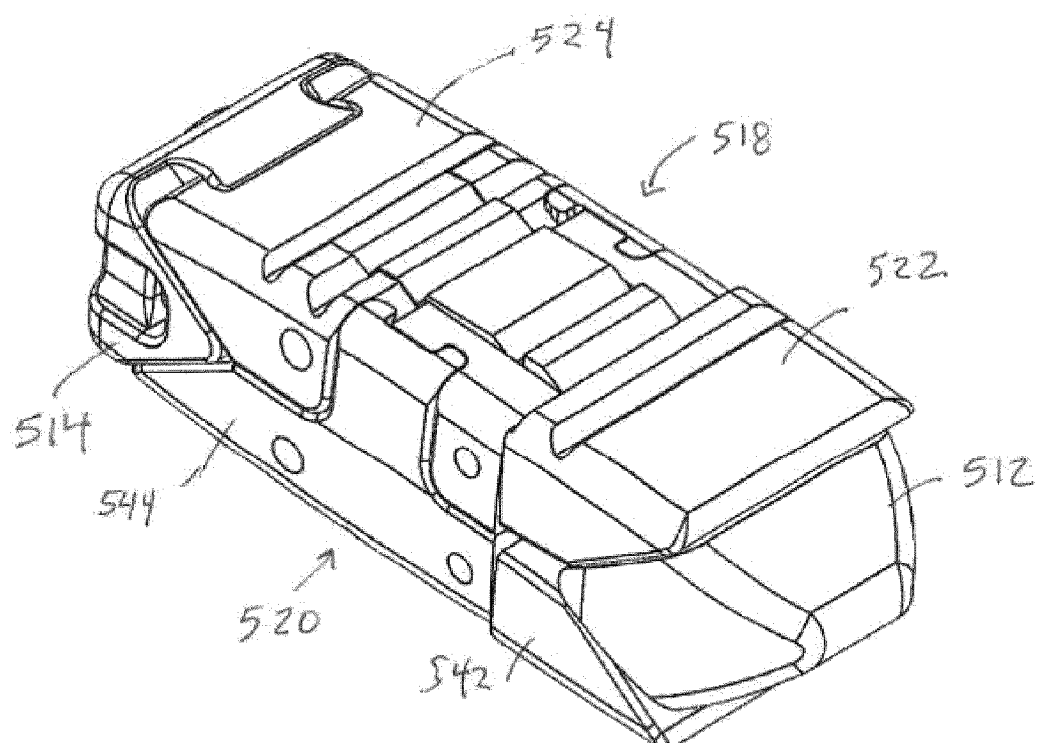
Figure 73:
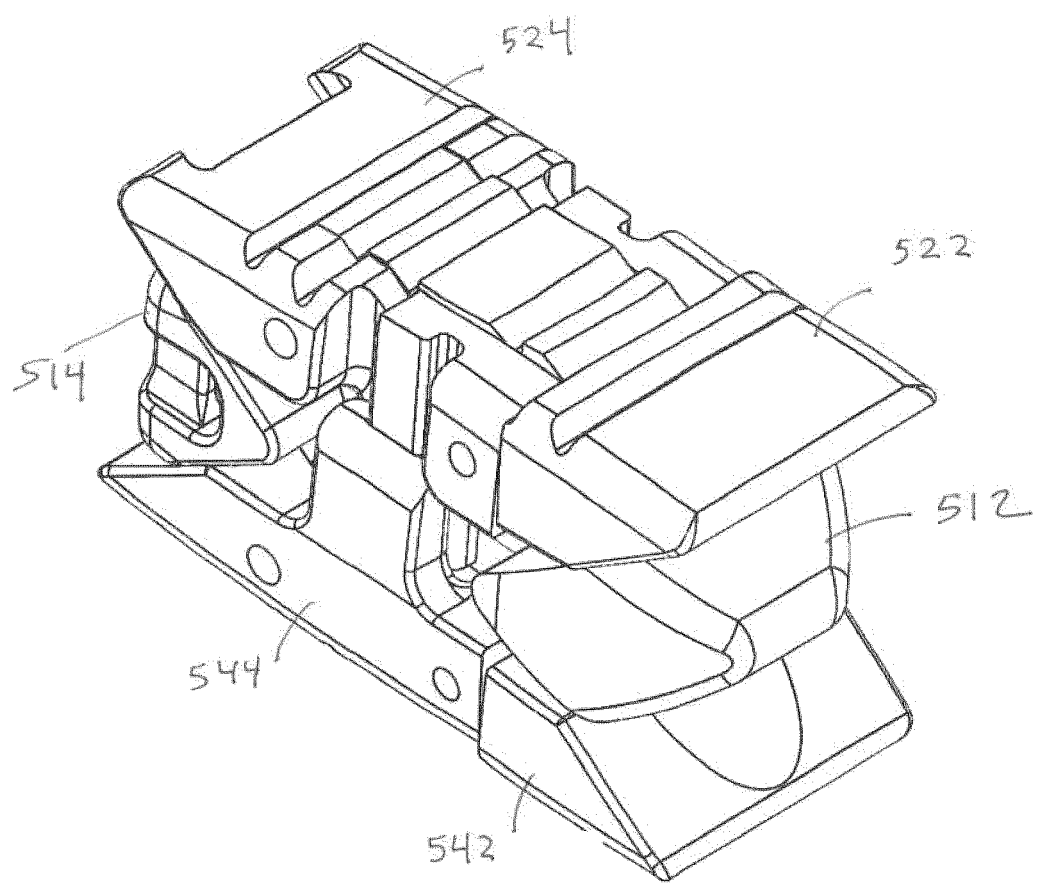
Figure 74:
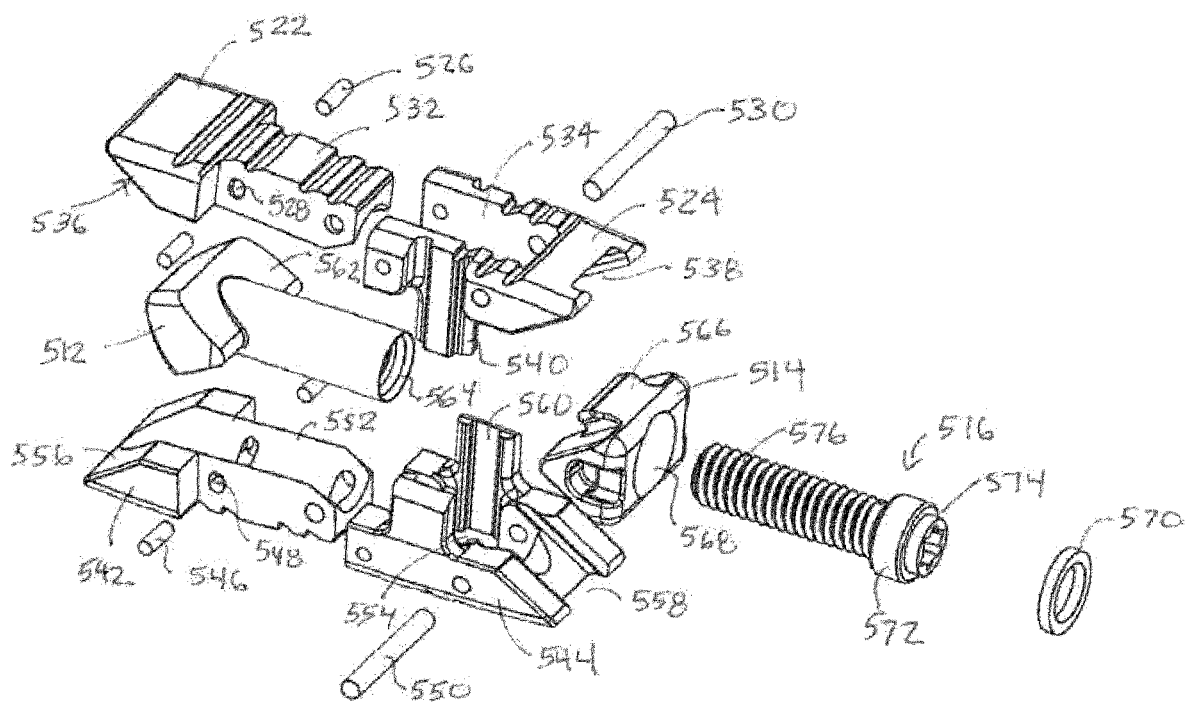
Figure 75:
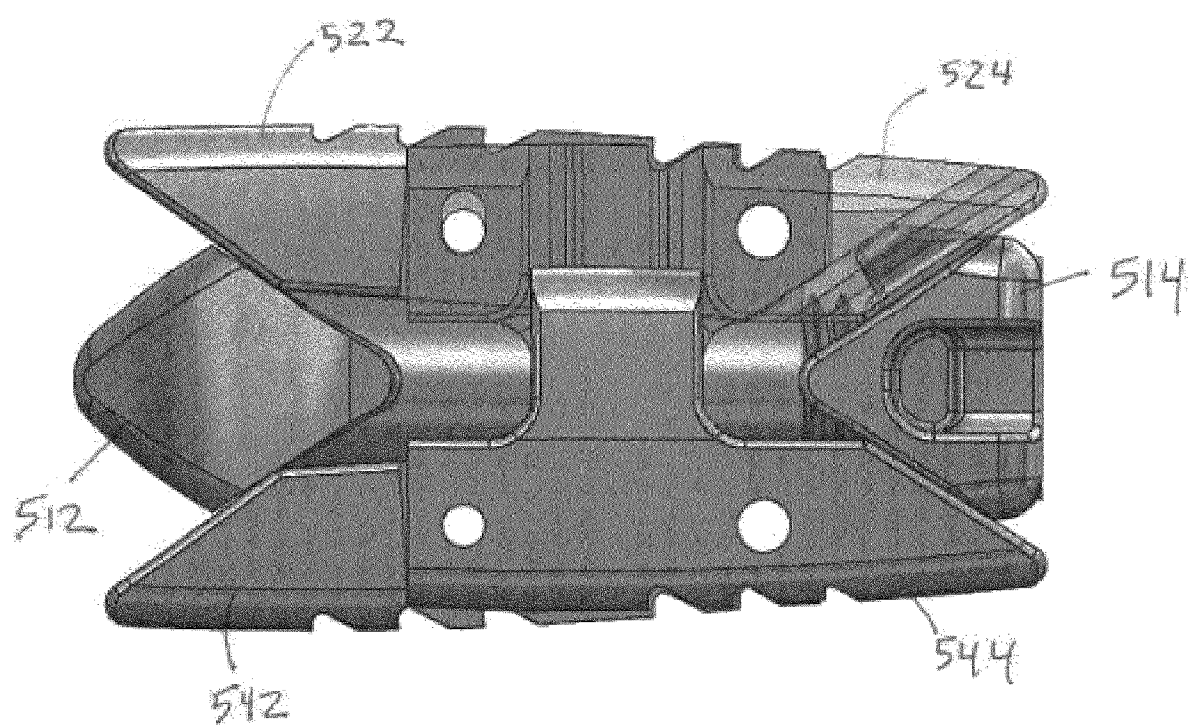

In one embodiment, implant 510 is moveable from a first, fully collapsed and aligned position, as shown in FIG. 71, to a second, collapsed and angulated position, as shown in FIG. 72, to a third, expanded and angulated position, as shown in FIG. 73. Implant 510 may be positioned at any desired intermediate position between the first, second, and third positions. In use, a first amount of rotation of control member 516 causes angulation of first portions 522, 542 relative to second portions 524, 544. As control member 516 is threaded into threaded bore 564, first portion 522 rotates about top pivot pin 530 and first portion 542 rotates about bottom pivot pin 550. First portions 522, 542 continue to angulate until top and bottom guide pins 526, 546 are retained by upper and lower slots 528, 548, which define the maximum amount of angulation for first portions 522, 542.

Once maximum angulation is reached, further rotation of control member 516 causes expansion of second members 524, 544 (and therefore also first members 522, 542) relative to one another in a generally linear fashion (e.g., through the interaction of alignment guides 540, 560). It should be noted that to enable angulation of first portions 522, 542, front portion 512 and first portions 522, 542 have generally flat, correspondingly shaped ramped surfaces 562 (on front portion 512), 536 (on first portion 522 of top support assembly 518), and 556 (on first portion 542 of bottom support assembly 520). To facilitate linear movement of second portions 524, 544, rear portion 514 includes dovetailed projections 566, which are received within dovetailed recesses 438 (on second portion 524 of top support assembly 518) and 558 (on second portion 544 of bottom support assembly 520).

The angulation and expansion features enable a user to initially install implant 510 in a collapsed, aligned position, as shown in FIG. 71, which may facilitate initial insertion and adjustment of the device. Once in proper position, implant 510 may be moved to a desired angulated and/or expanded configuration, as shown in FIGS. 72 and 73. In the fully expanded and angulated position, as shown in FIG. 73, the outer surfaces (e.g., top and bottom surfaces) of first portions 522, 542 are offset (e.g. angularly offset) from the outer surfaces of second portions 524, 544, and angularly offset from the longitudinal axis of implant 510 (e.g., an axis extending along control member 516). The amount of angulation may be varied to suit a particular application (e.g., an amount of spinal curvature to be accommodated by the implant, etc.).

Referring now to FIGS. 76-83, an implant 610 is shown according to an exemplary embodiment. Implant 610 is usable, for example, between and/or within vertebral bodies of the spine, and may share many of the features of the other inter/intra-body implants discussed elsewhere herein. It should be understood that implant 610 may in some embodiments be usable in other portions of the body in addition to the spine, and all such applications are to be understood to be within the scope of the present disclosure. Implant 610 is generally similar to the other implants discussed herein in structure and function except with respect to the two-piece top and bottom support member and specific control member features discussed below. As such, implant 610 is understood to include any or all of the features of the other implants described herein to the extent consistent with the additional features of implant 610 described herein.

According to an exemplary embodiment, implant 610 includes a first, or front portion 612, a second, or rear portion 614, a first, or inner, control member 615, a second, or outer, control member 616, and a receiver member 617, which collectively form a body or control assembly that extends along a longitudinal axis of implant 610. A first, or upper support assembly 618 (e.g., an upper plate or support member, etc.) and a second, lower support assembly 620 (e.g., a lower plate or support member), are coupled to the control assembly and may extend generally between front and rear portions 612, 614. According to an exemplary embodiment, first and second support assemblies 618, 620 define a height of implant 610 extending between the outer or top surface of first support assembly 618 and the outer or lower surface of second support assembly 620.

Front portion 612 includes ramped surfaces 654 and a receiver recess or bore 656. Rear portion 614 includes ramped surfaces 658 and control recess or bore 660. Ramped surfaces 654, 658 facilitate controlled expansion and contraction of top support assembly 618 and bottom support assembly 620 relative to one another.

In one embodiment, top support assembly 618 includes a first or inner portion 622 and a second or outer portion 624 pivotally coupled to first portion 622 by way of a top pivot pin 626. First portion 622 at least partially extends into a recess 628 in second portion 624. First portion 622 includes a ramped surface 630, and second portion 624 includes a ramped surface 632. Ramped surface 630 slidingly interfaces with a corresponding ramped surface 654 on front portion 612, and ramped surface 632 slidingly interfaces with a corresponding ramped surface 658 on rear portion 614.

In one embodiment, bottom support assembly 620 includes a first or inner portion 638 and a second or outer portion 640 pivotally coupled to first portion 638 by way of a bottom pivot pin 642. First portion 638 at least partially extends into a recess 644 in second portion 640. First portion 638 includes a ramped surface 646, and second portion 640 includes a ramped surface 648. Ramped surface 646 slidingly interfaces with a corresponding ramped surface 654 on front portion 612, and ramped surface 648 slidingly interfaces with ramped surface 658 on rear portion 614.

In one embodiment, implant 610 includes alignment features configured to limit a degree of angulation of second portions 624, 640 relative to first portions 622, 638. For example, in some embodiments, first portion 622 of top support assembly 618 includes a single alignment guide or member 634 that is received between two alignment guides or members 650 on first portion 638 of bottom support assembly 620. Alignment guides 634, 650 are collectively received in a top alignment recess in second portion 624 of top support assembly 618 and a bottom alignment recess 644 in second portion 640 of bottom support assembly 620. The various alignment components may be configured to enable a predetermined amount of angulation between first portions 622, 63 and second portions 624, 640.

Figure 76:
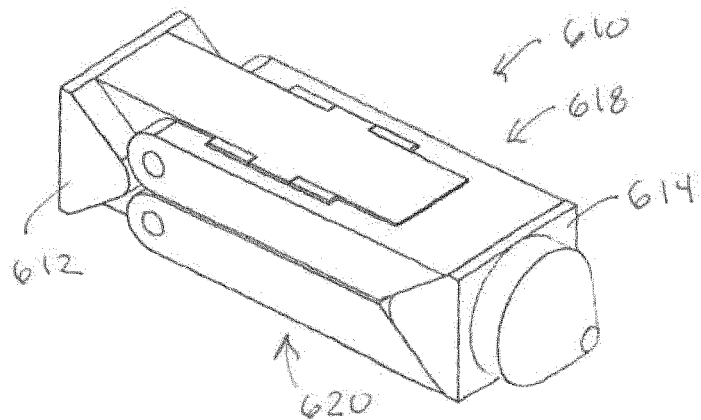
FIGS. 76-83 show various views of an expandable implant according to an alternative embodiment.
Figure 77:
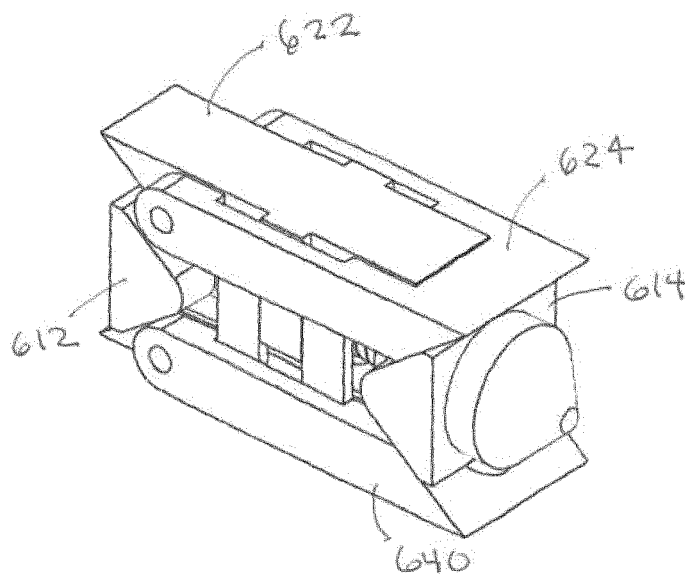
Figure 78:
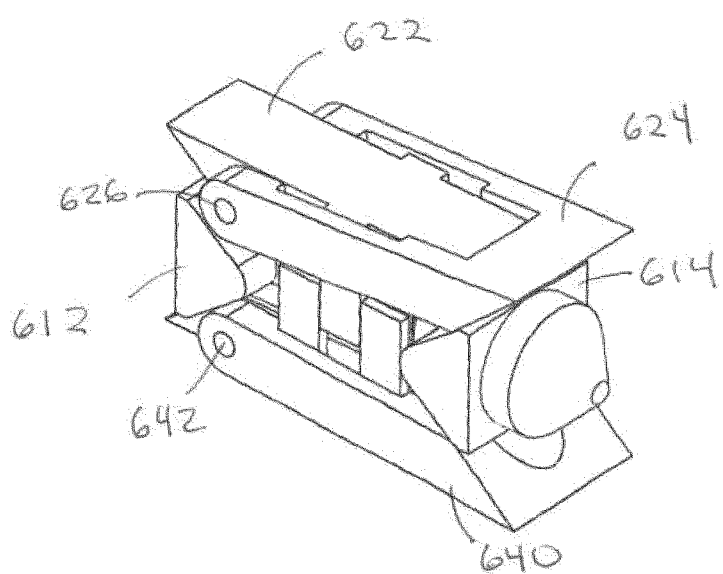
Figure 79:
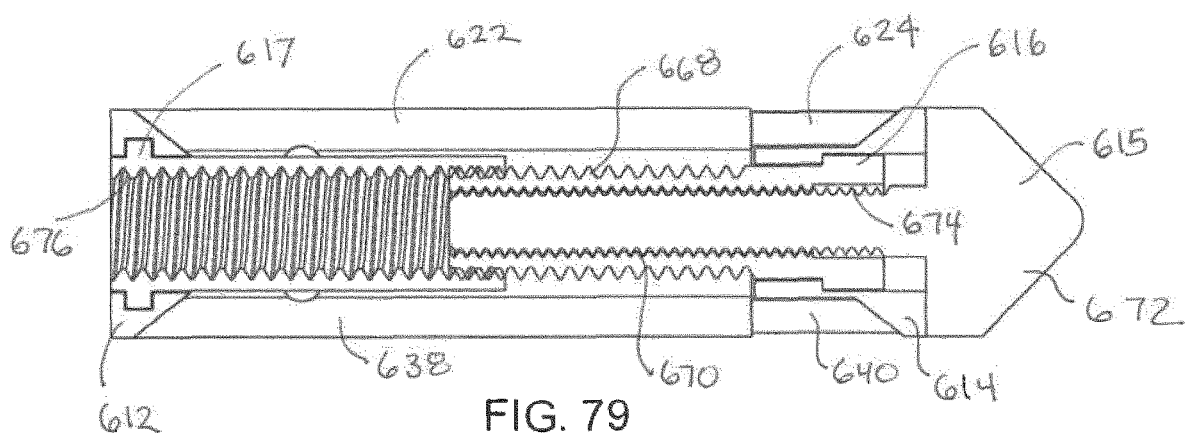
Figure 80:
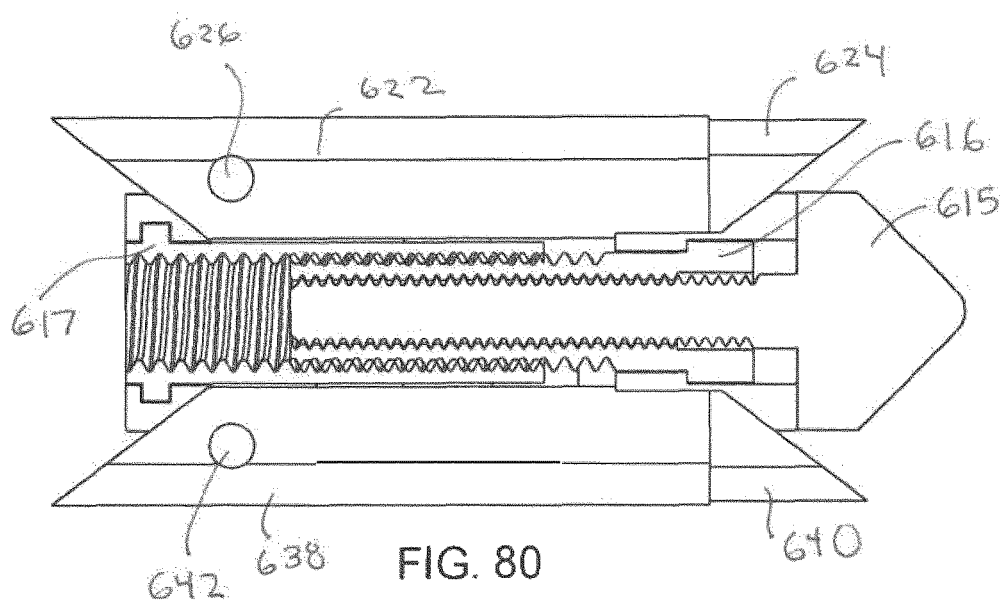
Figure 81:
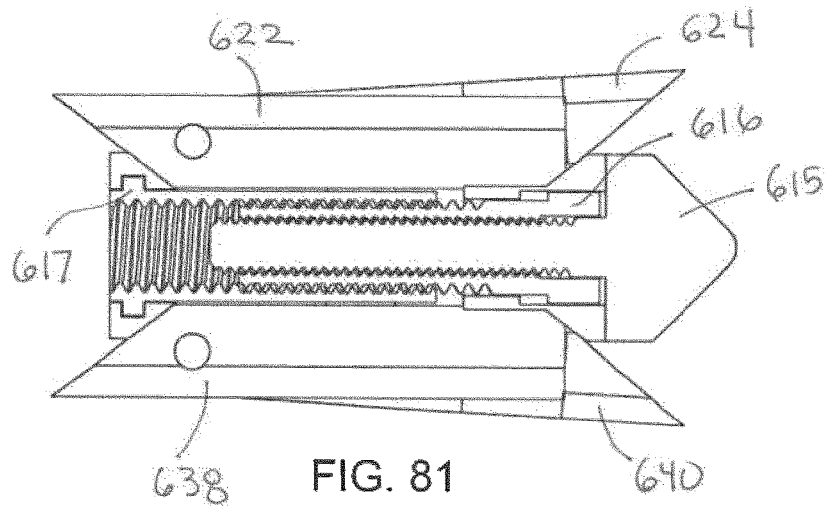
Figure 82:
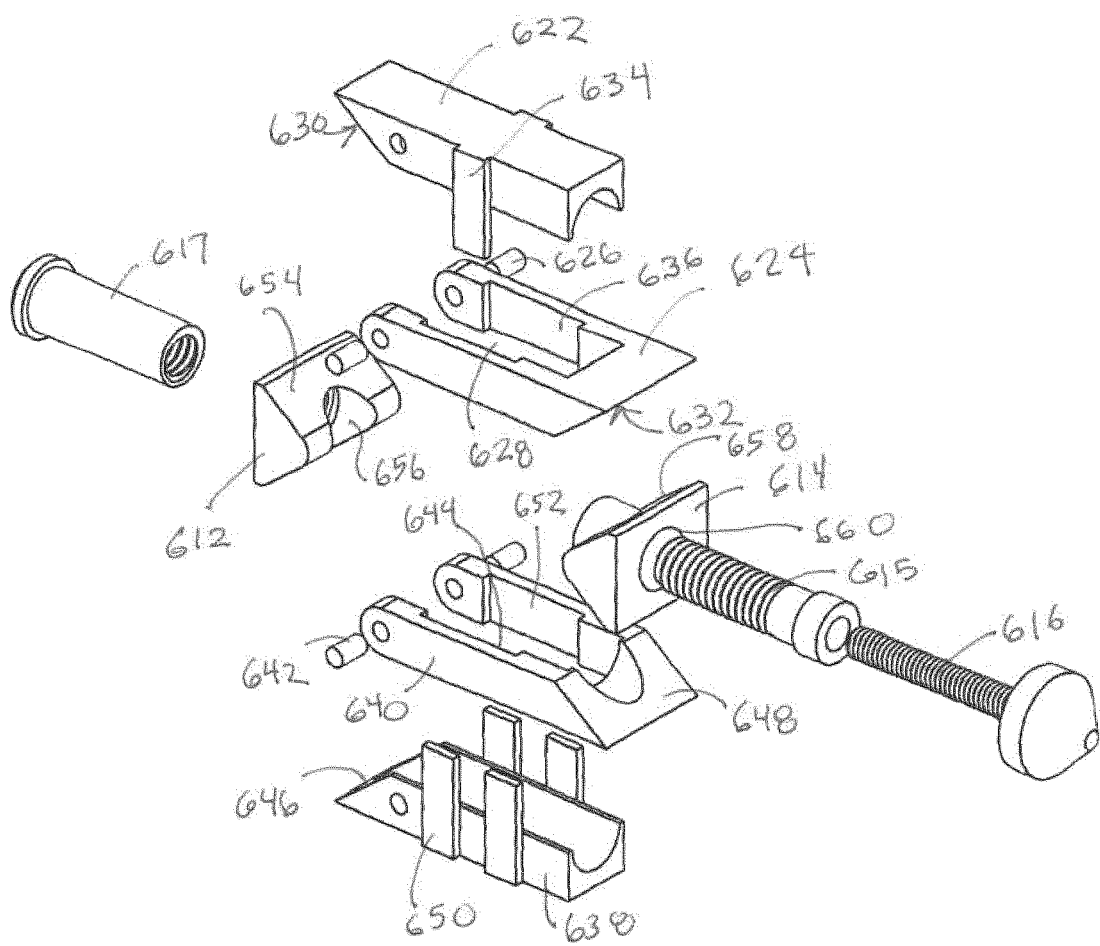
Figure 83:
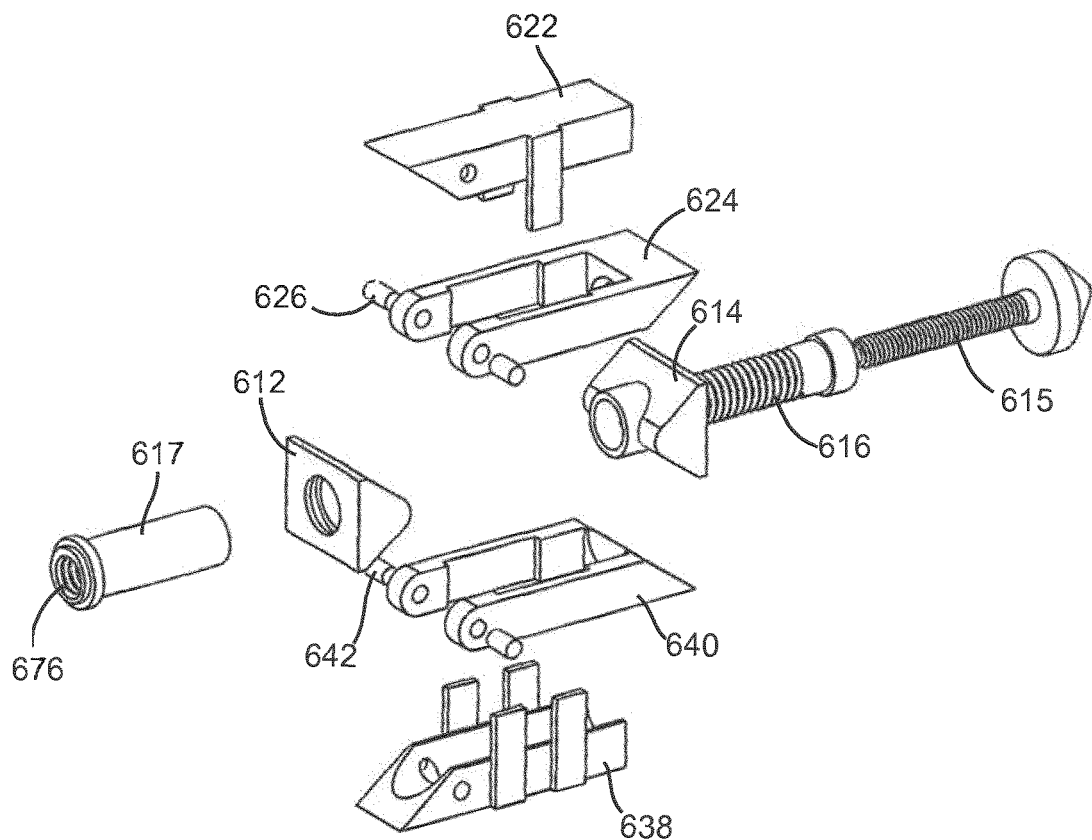

In one embodiment, implant 610 is moveable from a first, fully collapsed and aligned position, as shown in FIGS. 76 and 79, to a second, expanded and aligned position, as shown in FIGS. 77 and 80, to a third, expanded and angulated position, as shown in FIGS. 78 and 81. Implant 610 may be positioned at any desired intermediate position between the first, second, and third positions. Furthermore, the order of expansion and angulation may be reversed, or alternated, during installation.

In use, threading of outer control member 616 into (or out of) receiver 617 causes linear relative movement (e.g., expansion or contraction) of top support assembly 618 and bottom support assembly 620. For example, FIGS. 77 and 80 show implant 610 with outer control member 616 having been threaded into receiver 617 by way of threading engagement of the outer threads 668 of outer control member 616 and the inner threads 676 of receiver 617. As front portion 612 and rear portion 614 move toward/away from each other, top and bottom support assemblies 618, 620 likewise move away from/toward each other.

Threading of inner control member 615 within outer control 616 member causes second portions 624, 640 to angulate relative to first portions 622, 638. For example, FIGS. 78 and 81 show implant 610 with inner control member 615 having been threaded into outer control member 616, causing second portions 624, 640 to rotate about top and bottom pivot pins 626, 642, causing second portions 624, 640 to become angularly offset relative to first portions 622, 638.

Figure 69:
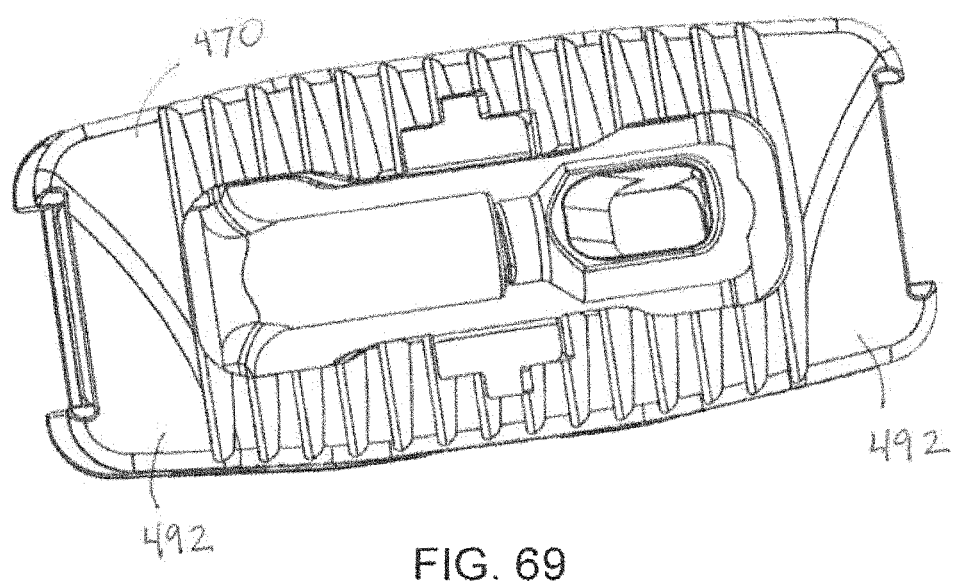

The angulation and expansion features enable a user to initially install implant 610 in a collapsed, aligned position, as shown in FIGS. 76 and 69, which may facilitate initial insertion and adjustment of the device. Once in proper position, implant 610 may be moved to a desired angulated and/or expanded configuration, as shown in FIGS. 77-78 and 80-81. In the fully expanded and angulated position, as shown in FIGS. 78 and 81, the outer surfaces (e.g., top and bottom surfaces) of second portions 624, 640 are offset (e.g. angularly offset) from the outer surfaces of first portions 622, 638, and angularly offset from the longitudinal axis of implant 610 (e.g., an axis extending along outer control member 616). The amount of angulation may be varied to suit a particular application (e.g., an amount of spinal curvature to be accommodated by the implant, etc.).

Figure 84:
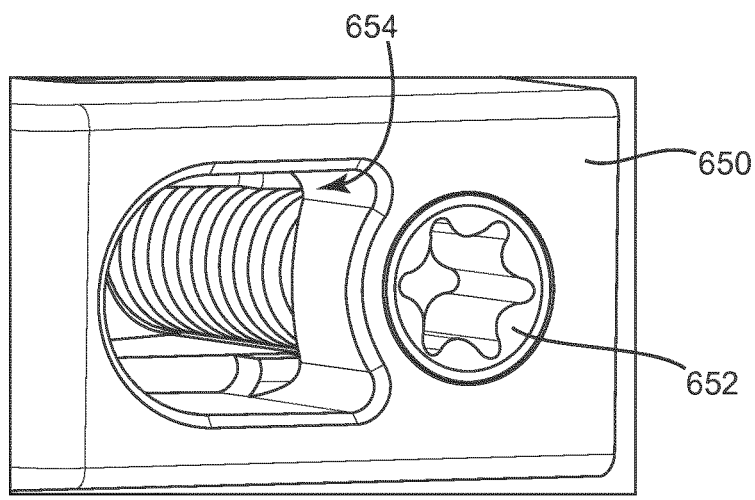
FIG. 84 shows a portion of an expandable implant according to an alternative embodiment.

Referring now to FIG. 84, a portion of an implant is shown according to an exemplary embodiment. In one embodiment, the portion includes a member 650, which may be similar to various components described with respect to the various other embodiments disclosed herein. For example, member 650 may form part of a control assembly and act as a rear member similar to rear portions 14, 114, 214, etc. As shown in FIG. 84, access to the interior of the various implants disclosed herein may be by way of member 650. Member 650 includes a control member 652 and an access aperture 654. Control member 652 acts to control expansion and contraction of the implant, and aperture 654 enables access to the interior of the implant. The access features of member 650 may be implemented in any of the implant components described herein, including the various front and rear portions, top and bottom supports, etc. All such combinations of features are to be understood to be within the scope of the present disclosure.

Referring to FIGS. 85-88, an implant 700 is shown according to an exemplary embodiment. The implant 700 is usable, for example, between and/or within vertebral bodies of the spine, and may share many of the features of the other inter/intra-body implants discussed elsewhere herein. It should be understood that the implant 700 may in some embodiments be usable in other portions of the body in addition to the spine, and all such applications are to be understood to be within the scope of the present disclosure. The implant 700 is similar to the implants 260, 410, 460, 510, and the other implants described herein, in structure and function except as discussed below. As such, the implant 700 is understood to include any or all of the features of the other implants described herein to the extent consistent with the additional features of the implant 700 described herein (e.g., retention pins, dovetail projections and ramped surfaces, alignment features, control member access port(s), etc.).

Figure 85:
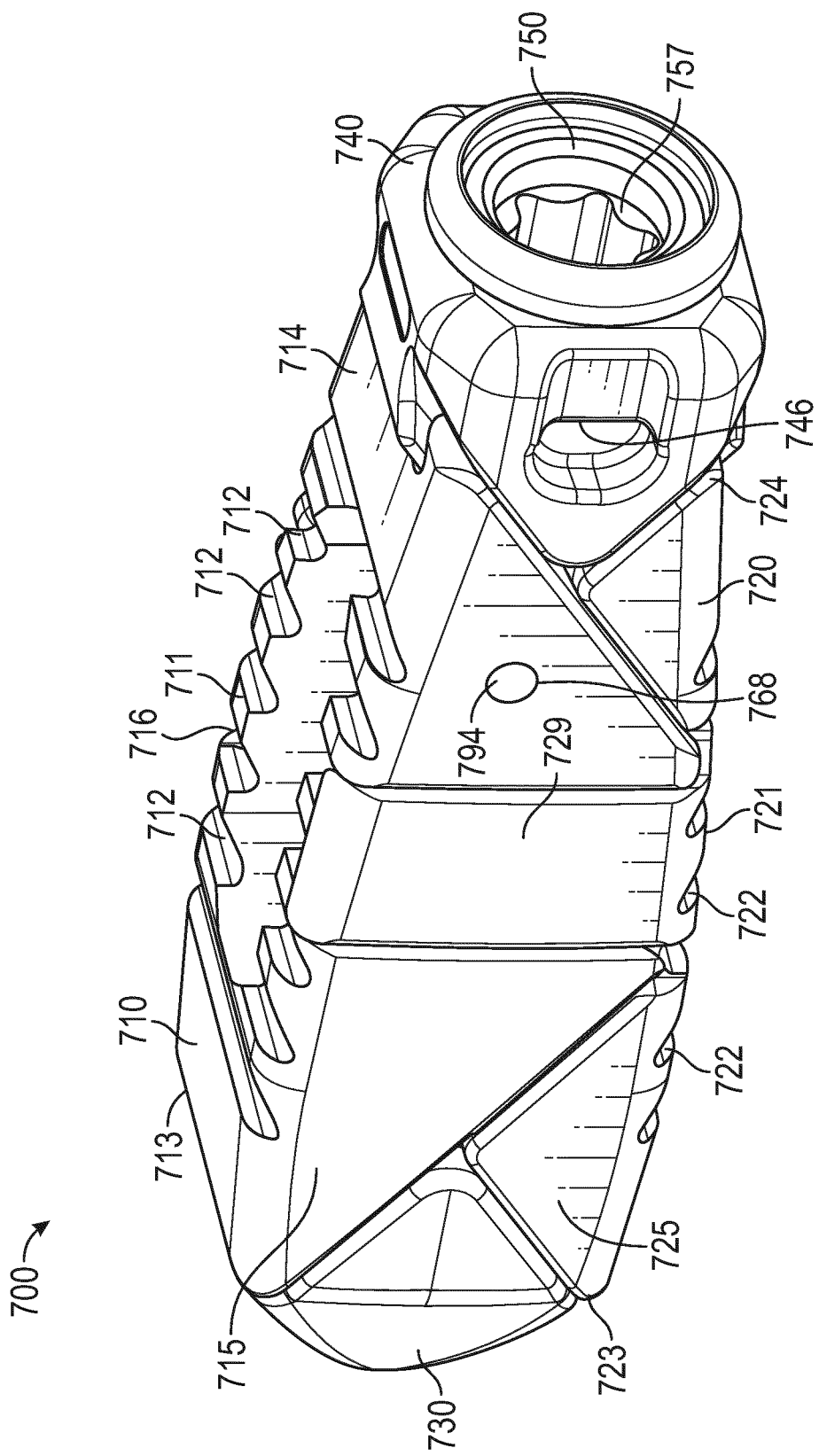
FIG. 85 shows a perspective view of an expandable implant according to an alternative embodiment.
Figure 86:
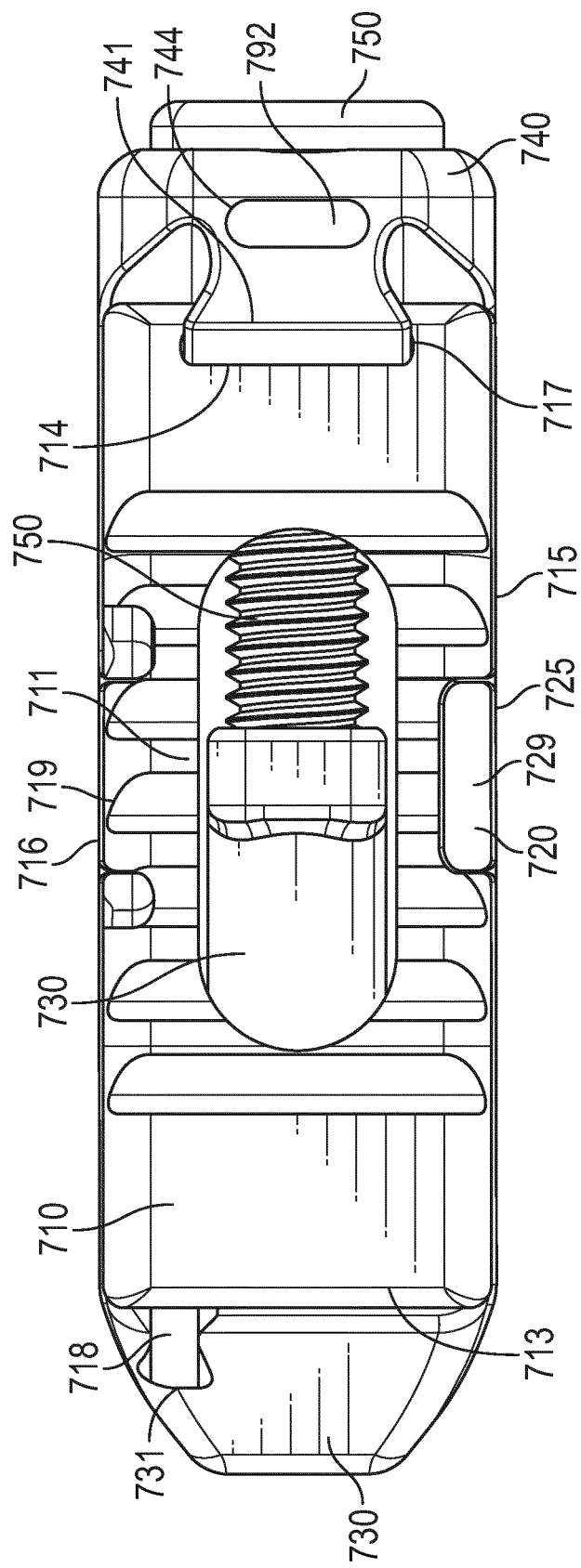
FIG. 86 shows a top view of the expandable implant of FIG. 85.
Figure 87:
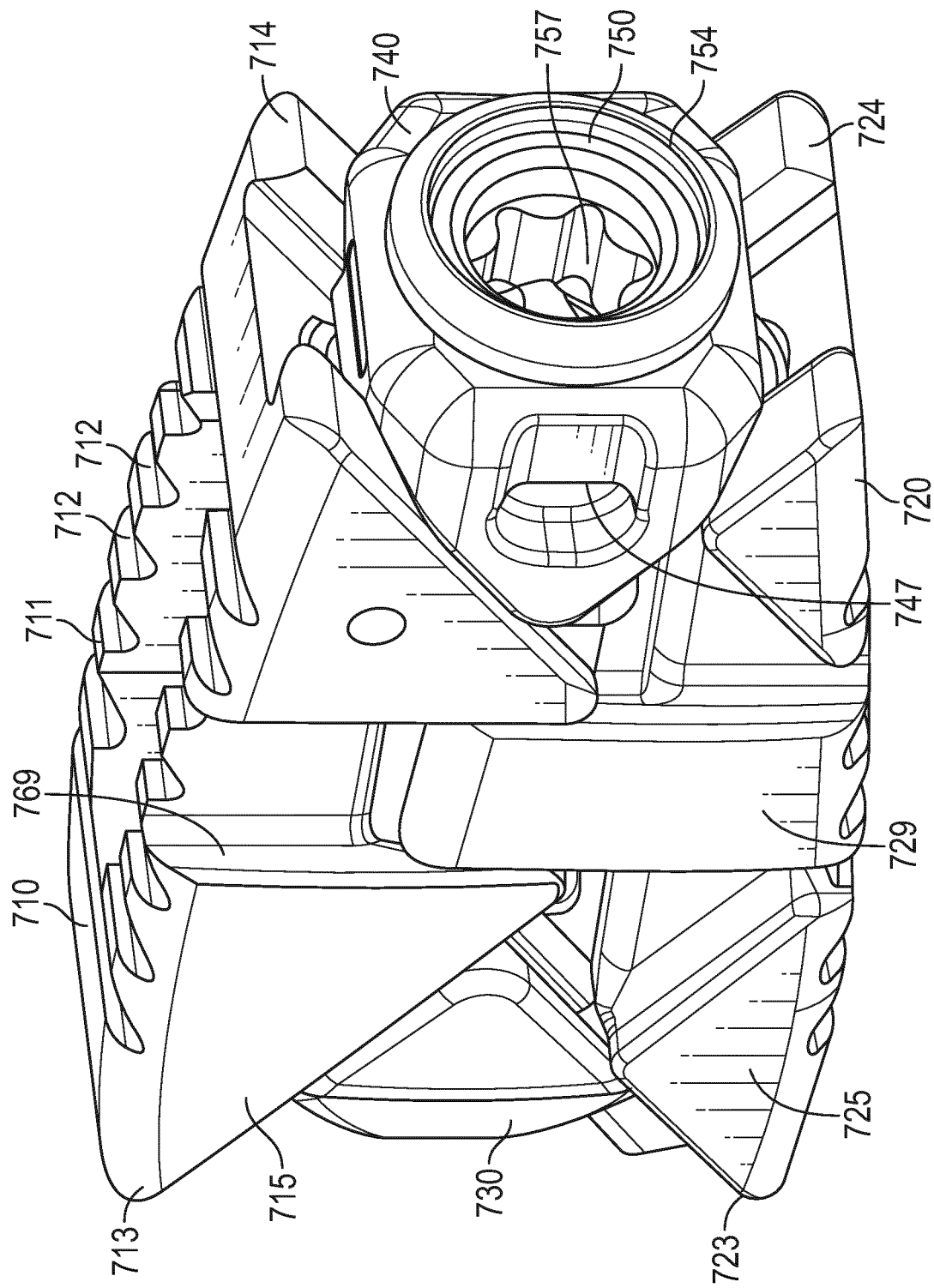
FIG. 87 shows another perspective view of the expandable implant of FIG. 85.
Figure 88:
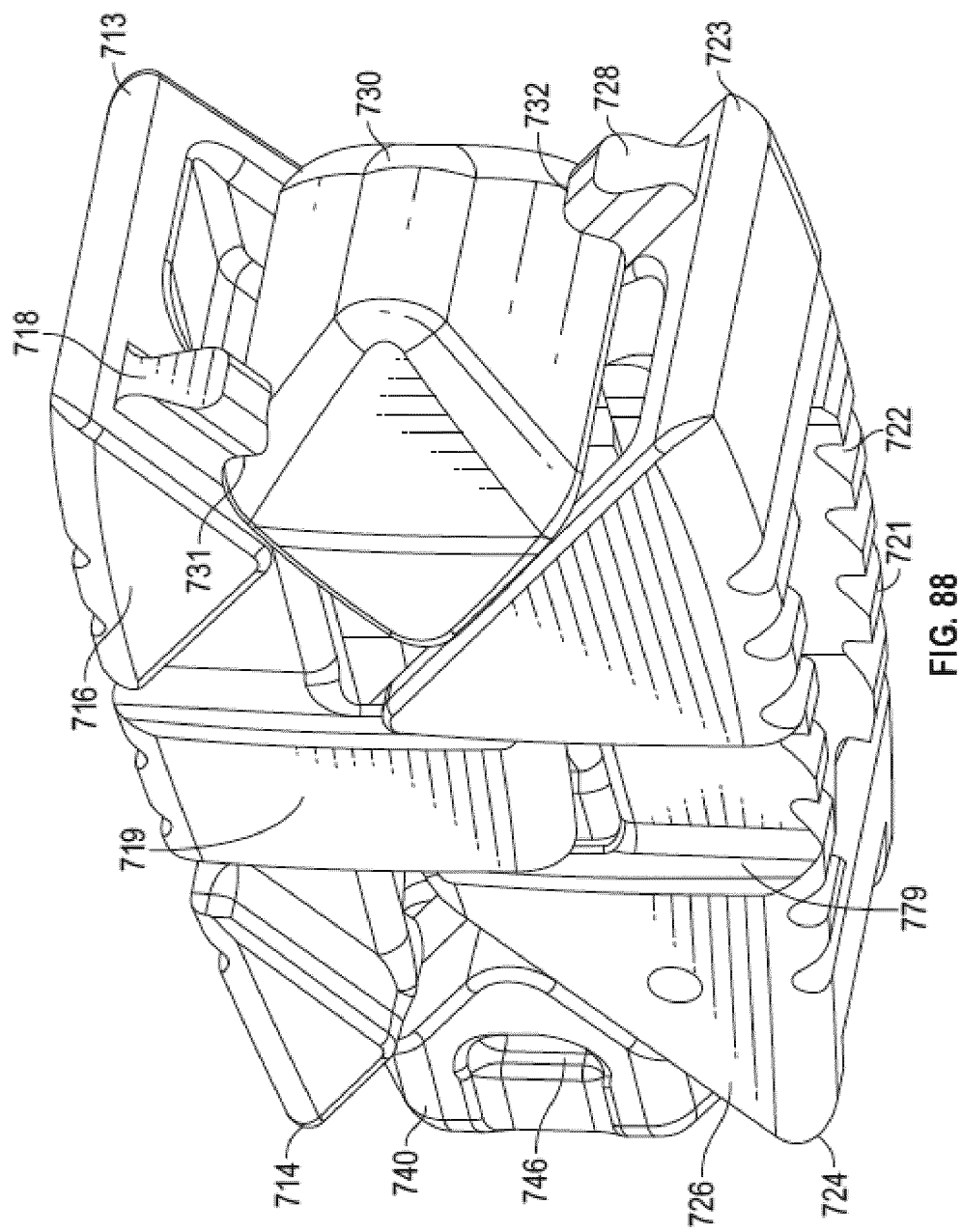
FIG. 88 shows another perspective view of the expandable implant of FIG. 85.

As will be discussed herein, the implant 700 is expandable between at least a first, collapsed orientation and a second, expanded orientation. For example, the implant 700 shown in FIGS. 85 and 86 is shown in the first, collapsed orientation according to some embodiments. Further, the implant 700 shown in FIGS. 87 and 88 is shown in the second, expanded orientation. The first, collapsed orientation does not necessarily require the implant 700 to be completely collapsed and the second, expanded orientation does not require the implant 700 to be completely expanded. Instead, the first, collapsed orientation and the second, expanded orientation may fall anywhere in-between the fully collapsed orientation and the fully expanded orientation, and including the fully collapsed orientation and the fully expanded orientation.

According to an exemplary embodiment, the implant 700 includes a first, or rear portion 740, a second, or front portion 730, and a third, intermediate, or control member or portion 750, which collectively form a control assembly 790 (see FIG. 90) that extends along a longitudinal axis of the implant 700. A first, or top portion 710 (e.g., an upper plate or support member, etc.) and a second, bottom portion 720 (e.g., a lower plate or support member), are coupled to the body or control assembly 790 and may extend generally between rear portion 740 and the front portion 730.

In some embodiments, the rear portion 740 includes an aperture 743 (see FIG. 89) configured to enable the control member 750 to extend through the rear portion 740 and into a central cavity of the implant 700. The rear portion 740 may also include a plurality of apertures configured to receive retention members. For example, the rear portion 740 may include a first aperture 744 proximate an upper portion of the rear portion 740 and a second aperture 745 proximate a lower portion of the rear portion 740 (see FIG. 89). The first aperture 744 and the second aperture 745 may be configured to individually receive a retention wedge 792 as will be discussed further herein. Further, the rear portion 740 may include an installation tool interface 746, 747. For example, the rear portion 740 may include a first installation tool interface 746 on a first side and a second installation tool interface 747 on a second side. An installation tool may be used to grab the first installation tool interface 746 and the second installation tool interface 747 in order to secure the implant 700 to the installation tool so that the implant 700 can be inserted into a person.

The top portion 710 may have an upper surface 711. In some embodiments, such as shown in FIG. 85, the upper surface 711 has a plurality of ridges and/or grooves 712. The plurality of ridges and/or grooves 712 may provide a surface roughness that will increase the stability of the implant 700 once inserted into a person. Similarly, the bottom portion 720 may have a lower surface 721. In some embodiments, such as shown in FIG. 85, the lower surface 721 has a plurality of ridges and/or grooves 722. The plurality of ridges and/or grooves 712 may provide a surface roughness that will increase the stability of the implant 700 once inserted into a person. Further, in some embodiments, the top portion 710 and the bottom portion 720 may be identical. In some embodiments, this may reduce the cost of manufacturing the implant 700.

According to an exemplary embodiment, the upper surface 711 and lower surface 721 define a height of the implant 700 (e.g., a support height defined by the vertical distance between the upper surface 711 of the top portion 710 and the lower surface 721 of the bottom portion 720). In some embodiments, the height of the implant 700 may be constant throughout the implant. However, in the embodiment shown in FIGS. 85-88, the height of the implant is generally greater near the front portion 730 than the height near the rear portion 740. In some embodiments, such as shown in FIGS. 85-88, the upper surface 711 and the lower surface 721 are generally parabolic when viewed from the side as discussed below. It should be appreciated that the height and general profile of the implant 700 may be customized based on the needs of the person the implant 700 is being inserted into.

In some embodiments, the implant 700 defines a longitudinal axis extending along the control member 750. The top portion 710 defines a rear or first end 714, a front or second end 713 opposite the rear or first end 714, a first side 715, and a second side 716 opposite the first side 715. The first end 714 and the second end 713 define an overall taper to the upper surface 711. In some embodiments, the upper surface 711 may define an arcuate shape between the rear or first end 714 and the second end 713 (e.g., such that the upper surface 711 has a slight curvature, such as a parabolic curve, between the first end 714 and the second end 713 when viewed from the first side 715). In other embodiments, the upper surface 711 may define a substantially planar surface between the first end 714 and the second end 713.

The bottom portion 720 defines a first end 724, a second end 723, a first side 725 and a second side 726. The lower surface 721 extends between the first end 724 and the second end 723. The first end 724 and the second end 723 define an overall taper to lower surface 721. In some embodiments, lower surface 821 may define an arcuate shape between the first end 724 and the second end 723 (e.g., such that the bottom surface 721 has a slight curvature, such as a parabolic curve, between the first end 724 and the second end 723 when viewed from the first side 725). In other embodiments, the bottom surface 721 may define a substantially planar surface between the first end 724 and the second end 723.

As shown in FIGS. 87 and 88, the top portion 710 and the bottom portion 720 move toward and away from each other in a linear manner, such that the degree of taper remains constant and the implant 700 expands from the first, collapsed position to the second, expanded position. In other embodiment, other configurations may be utilized to provide non-linear movement and a varying longitudinal taper. Furthermore, while FIGS. 85-88 illustrate an implant having a parabolic longitudinal taper, according to various alternative embodiments, implants may be provided having a variable longitudinal taper. Further, in various alternative embodiments, the implant may taper from the first lateral side to the second lateral side, or vice versa.

Referring now to FIG. 86, the top portion 710 may include a cutout 717 at the first end 714. In certain embodiments, the cutout 717 is generally dovetail shaped and is centered between the first side 715 and the second side 716. The cutout 717 is configured to receive a projection 741 of the rear portion 740. In certain embodiments, the projection 741 is generally dovetail shaped. As the implant 700 expands from the first, collapsed position to the second, expanded position, the projection 741 will slide within the cutout 717. Further, the top portion 710 may include a rail 718 at the second end 713. The rail 718 may be configured to be received by a groove 731 in the front portion 730. As the implant 700 expands from the first, collapsed position to the second, expanded position, the rail 718 may slide within the groove 731. In certain embodiments, the rail 718 is off-center and is closer to the second side 716 than the first side 715. In certain embodiments, the rail 718 is generally dovetail shaped and the groove 731 is generally dovetail shaped.

The top portion 710 may also include a side projection 719 on the second side 716 between the first end 714 and the second end 713. The side projection 719 may be configured to be received by a slot 779 on the first side 725 of the bottom portion 720. When the implant 700 expands from the first, collapsed position to the second, expanded position, the projection 719 may slide within the slot 779. The side projection 719 may provide the implant 700 with additional lateral stability to prevent the top portion 710 shifting laterally with respect to the bottom portion 720.

Figure 89:
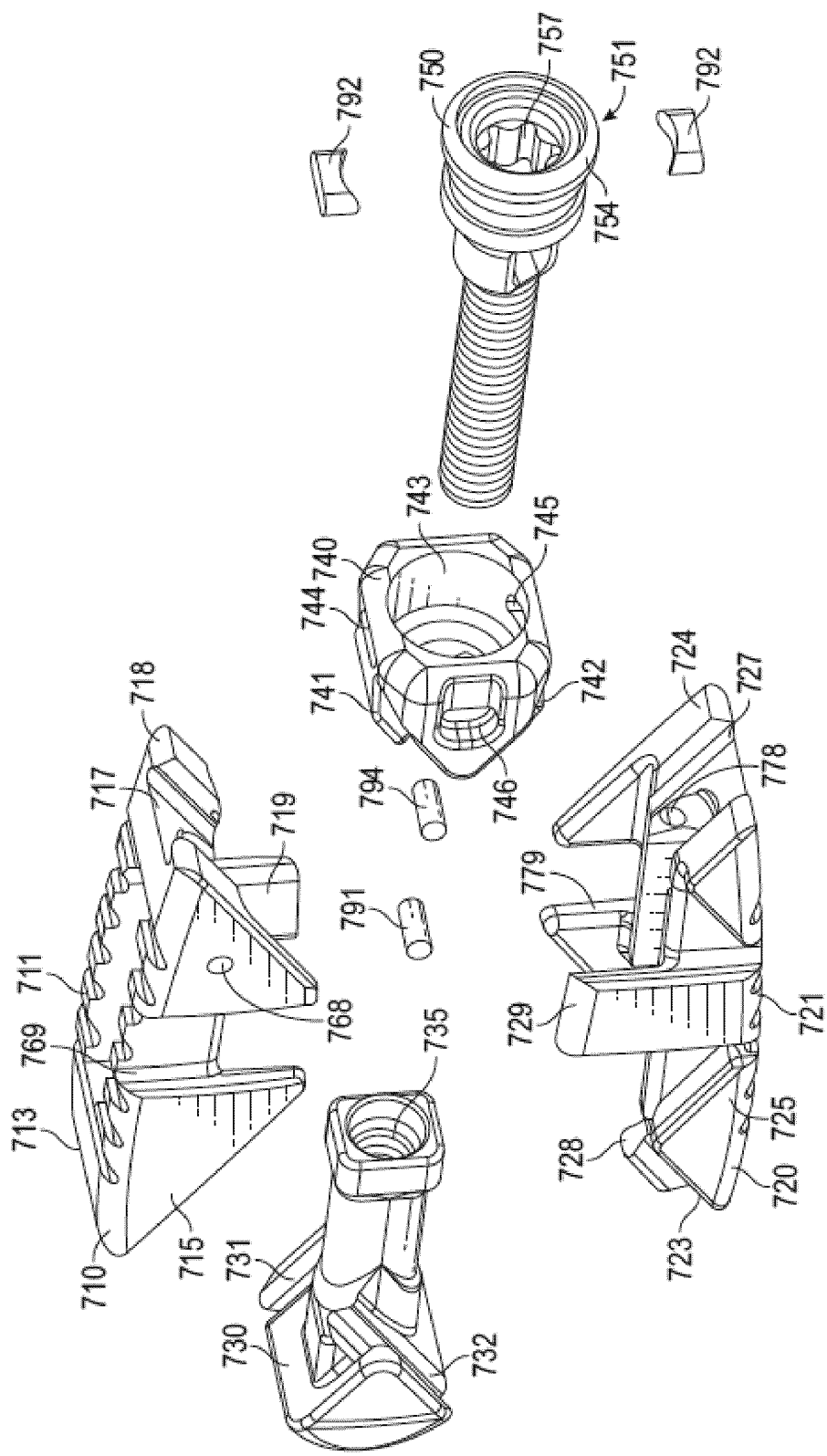
FIG. 89 shows an exploded view of the expandable implant of FIG. 85.

Referring now to FIGS. 88 and 89, the bottom portion 720 may include a cutout 727 at the first end 724. In certain embodiments, the cutout 727 is generally dovetail shaped and is centered between the first side 725 and the second side 726. The cutout 727 is configured to receive a projection 742 of the rear portion 740. In certain embodiments, the projection 742 is generally dovetail shaped. As the implant 700 expands from the first, collapsed position to the second, expanded position, the projection 742 will slide within the cutout 727. Further, the bottom portion 720 may include a rail 728 at the second end 723. The rail 728 may be configured to be received by a groove 732 in the front portion 730. As the implant 700 expands from the first, collapsed position to the second, expanded position, the rail 728 may slide within the groove 732. In certain embodiments, the rail 728 is off-center and is closer to the first side 725 than the second side 726. In certain embodiments, the rail 718 is generally dovetail shaped and the groove 731 is generally dovetail shaped.

The bottom portion 720 may also include a side projection 729 on the first side 725 between the first end 724 and the second end 723. The side projection 729 may be configured to be received by a slot 769 on the first side 715 of the top portion 710. When the implant 700 expands from the first, collapsed position to the second, expanded position, the projection 729 may slide within the slot 769. The side projection 729 may provide the implant 700 with additional lateral stability to prevent the top portion 710 shifting laterally with respect to the bottom portion 720.

Referring now to FIG. 89, in some embodiments, the implant 700 includes one or more retaining members to prevent undesired expansion and/or collapsing of the implant 700. For example, once the implant 700 is set to a desired height, a first retention pin 794 may be driven (e.g., press fit) into a first pin aperture 768 on the first side 715 of the top portion. Additionally, a second retention pin 794 may be driven (e.g., press fit) into a second pin aperture 778 on the second side 726 of the bottom portion 720. In doing so, the retention pins 794 may extend into the center cavity of the implant 700, thereby preventing the rear portion 740 from moving closer to the front portion 730, thereby preventing over expansion of the implant 700. Additionally, the retention pins 794 may prevent the implant 700 from collapsing by preventing the bottom portion 720 and the top portion 710 from returning to the first, collapsed position. In various alternative embodiments, retaining members may be used that extend through other portions, such as opposing top and bottom sides. Further, as will be discussed below, in some embodiments, the implant 700 may include additional retention members, such as the retention wedges 792.

Figure 90:
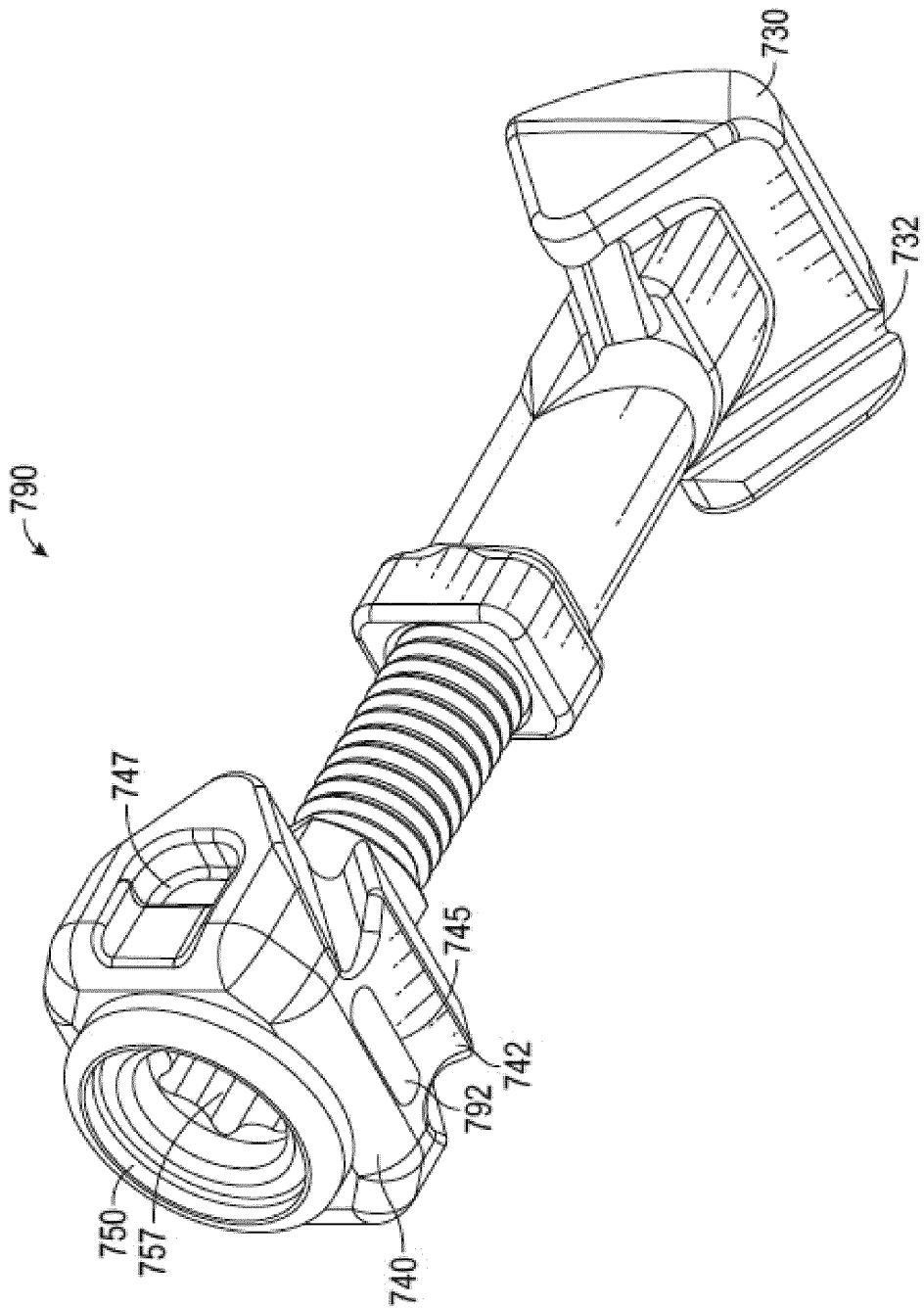
FIG. 90 shows a perspective view of a control assembly according to an example embodiment.
Figure 91:
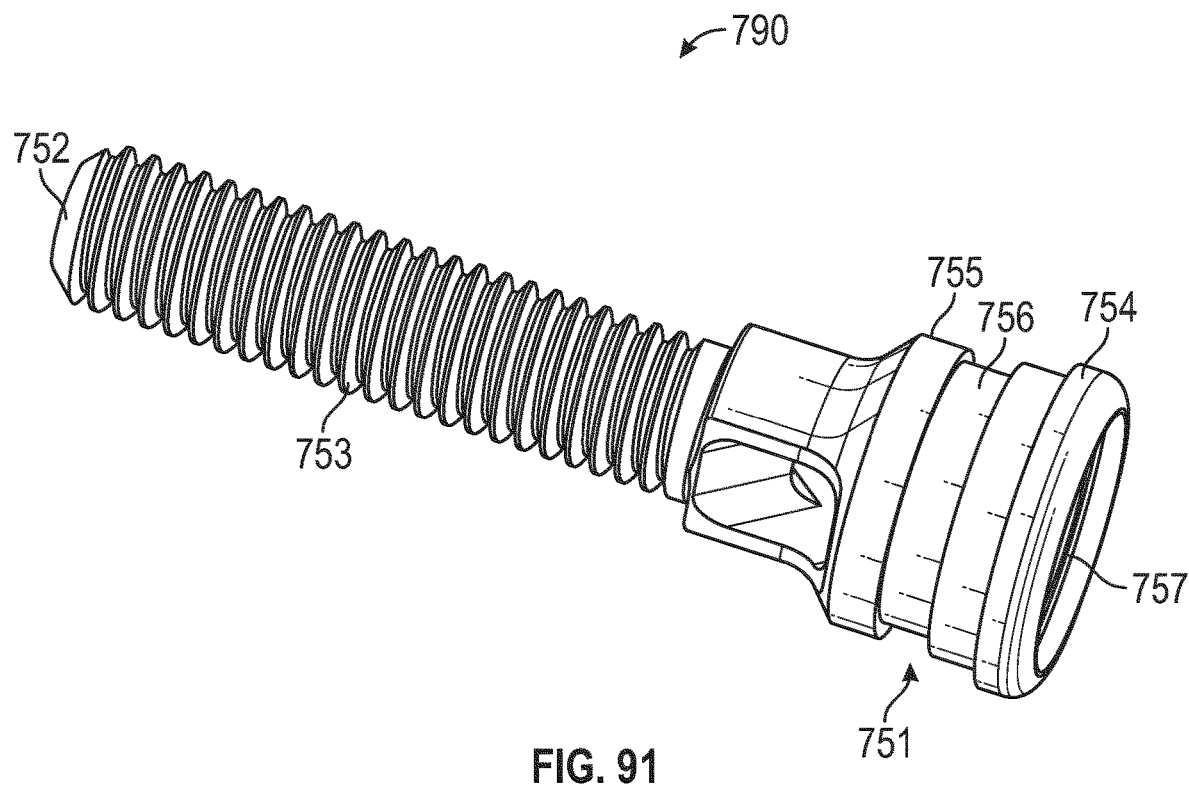
FIG. 91 shows a perspective view of a control member according to an example embodiment.

Referring now to FIGS. 90 and 91, the control assembly 790 is shown according to an example embodiment. The control assembly 790 includes the rear portion 740 adjustably coupled to the front portion 730 by the control member 750. As shown in FIG. 91, the control member 750 includes a head portion 751, a tip 752 opposite the head portion 751, and a threaded shaft 753 positioned between the head portion 751 and the tip 752. The head portion 751 further includes an outer ring 754, an access ring 755, a retention groove 756 in the access ring 755, and a tool port 757 configured to receive a tool that may be used to manipulate the control member 750 to cause expansion of the implant 700. As shown, the outer ring 754 has an exterior diameter larger than the inner diameter of the aperture 743. Therefore, as the head portion 751 moves closer to the front portion 730, the outer ring 754 will engage the rear face of the rear portion 740, thereby causing the rear portion 740 to move closer to the front portion 730, causing expansion of the implant 700. The access ring 755 may have a smaller exterior diameter than the aperture 743 so that a portion of the head portion 751 may be received by the aperture 743 while a portion of the head portion 751 (e.g., the outer ring 754) remains outside of the aperture as the implant 700 is expanded. Further, the retention groove 756 may have an exterior diameter smaller than the exterior diameter of the access ring 755 so that a retention member (e.g., retention wedge 792) may be inserted into the retention groove 756.

After the implant 700 is inserted, the control assembly 790 may be used to expand the implant 700 from the first, collapsed position to the second, expanded position. For example, a person may use an expansion tool that engages with the tool port 757 of the control member 750. For example, the expansion tool may be a torx head screwdriver. Since the outer ring 754 has a larger exterior diameter than the inner diameter of the aperture 743, the tool port 757 may provide a larger access area than a control member that does not have an outer ring with an exterior diameter larger than the inner diameter of the aperture 743. A person, such as a surgeon or doctor, may then use the expansion tool to turn the control member 750, for example, in a clockwise direction. In this example embodiment, the threaded shaft 753 is received by a threaded bore 735 of the front portion 730 (see FIG. 89). As the control member 750 is turned, the tip 752 will continue to move further into the threaded bore 735. For example, turning the control member 750 in a clockwise direction will cause the head portion 751 of the control member 750 to move in a direction towards the front portion 730. Since the diameter of the outer ring 754 is larger than the aperture 743, as the head portion 751 moves closer to the front portion 730, the rear portion 740 will also move closer to the front portion 730. As the front portion 730 and the rear portion 740 move near each other, ramped surfaces of the front portion 730 and the rear portion 740 slidably engage the top portion 710 and the bottom portion 720, thereby causing the top portion 710 and the bottom portion 720 to move linearly away from each other. It should be appreciated that, while the Figures generally show control member 750 threadingly engaging front portion 730, in other embodiments, other adjustment mechanisms may be used (e.g., ratchet mechanisms, indents/detents, etc.). In these embodiments, the control member 750 may be manipulated (e.g., urged, turned, pushed, rotated, etc.) to control relative movement between the top portion 710 and the bottom portion 720.

Further, it should be appreciated that the expansion profile of an implant may be customized in part by changing the angles of the various ramped surfaces. Using the implant in various locations may require a custom expansion profile. For example, if the implant is inserted into a patient's spine, the implant expansion profile may be customized to match the curvature of the patient's spine at the desired location that the implant is to be implanted into. In some example embodiments, the ramped surfaces of the rear portion 740 may have a much higher angle (i.e., the angle that upward angled surface and the downward angle surface form) than the ramped surfaces of the front portion 730. In this example embodiment, turning the control member 750 will cause the implant 700 to expand more near the rear portion 740 than near the front portion 730. In this example embodiment, the implant 700 height will be larger near the rear portion 740 than near the front portion 730. It should be appreciated that further customization of the expansion profile of an implant 700 may be accomplished by adjusting the angle of ramped surfaces on the rear portion 740, the front portion 730, the top portion 710, and the bottom portion 720.

Further, the retention wedge 792 may be used to prevent back-out of the control member 750. For example, if the implant 700 is compressed (i.e., a downward force on the upper surface 711 and an upward force on the lower surface 721), the control member 750 may experience forces that would force the control member 750 away from the front portion 730. To prevent this, a retention wedge 792 may be inserted into the first aperture 744 and the second aperture 745 of the rear portion 740. The retention wedges 792 may then extend into the retention groove 756 in the access ring 755 such that a portion of the retention wedge 792 is positioned within the first aperture 744 or the second aperture 745 and the retention groove 756, thereby preventing the control member 750 from backing out of the rear portion 740. In some embodiments, the surface of the retention wedge 792 that engages the retention groove 756 may have a curvature that matches the curvature of the retention groove 756, thereby allowing a greater portion of the retention wedge 792 to be positioned within the retention groove 756.

Referring to FIGS. 92-95, an implant 800 is shown according to an exemplary embodiment. The implant 800 is usable, for example, between and/or within vertebral bodies of the spine, and may share many of the features of the other inter/intra-body implants discussed elsewhere herein. It should be understood that the implant 800 may in some embodiments be usable in other portions of the body in addition to the spine, and all such applications are to be understood to be within the scope of the present disclosure. The implant 800 is similar to the implants 260, 410, 460, 510, 700, and the other implants described herein, in structure and function except as discussed below. As such, the implant 800 is understood to include any or all of the features of the other implants described herein to the extent consistent with the additional features of the implant 800 described herein (e.g., retention pins, dovetail projections and ramped surfaces, alignment features, control member access port(s), etc.).

Figure 92:
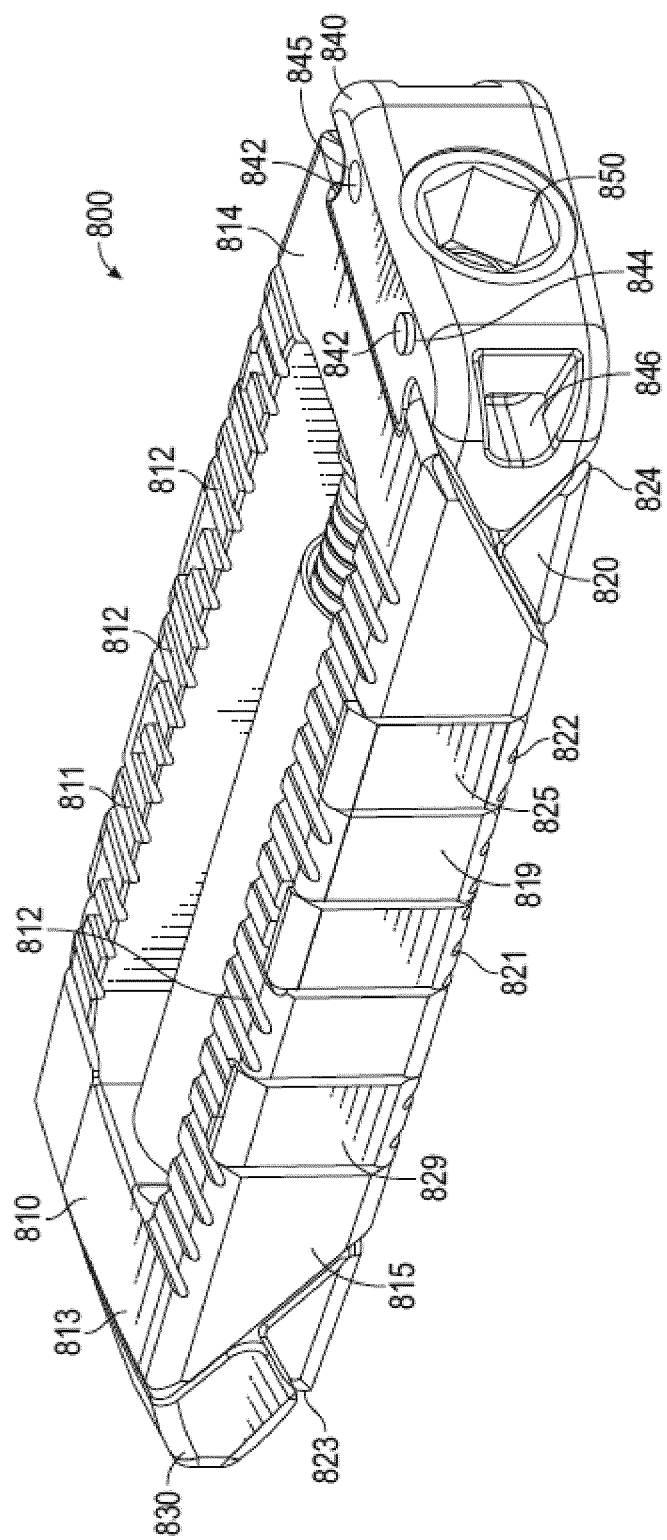
FIG. 92 shows a perspective view of an expandable implant according to an alternative embodiment.
Figure 93:
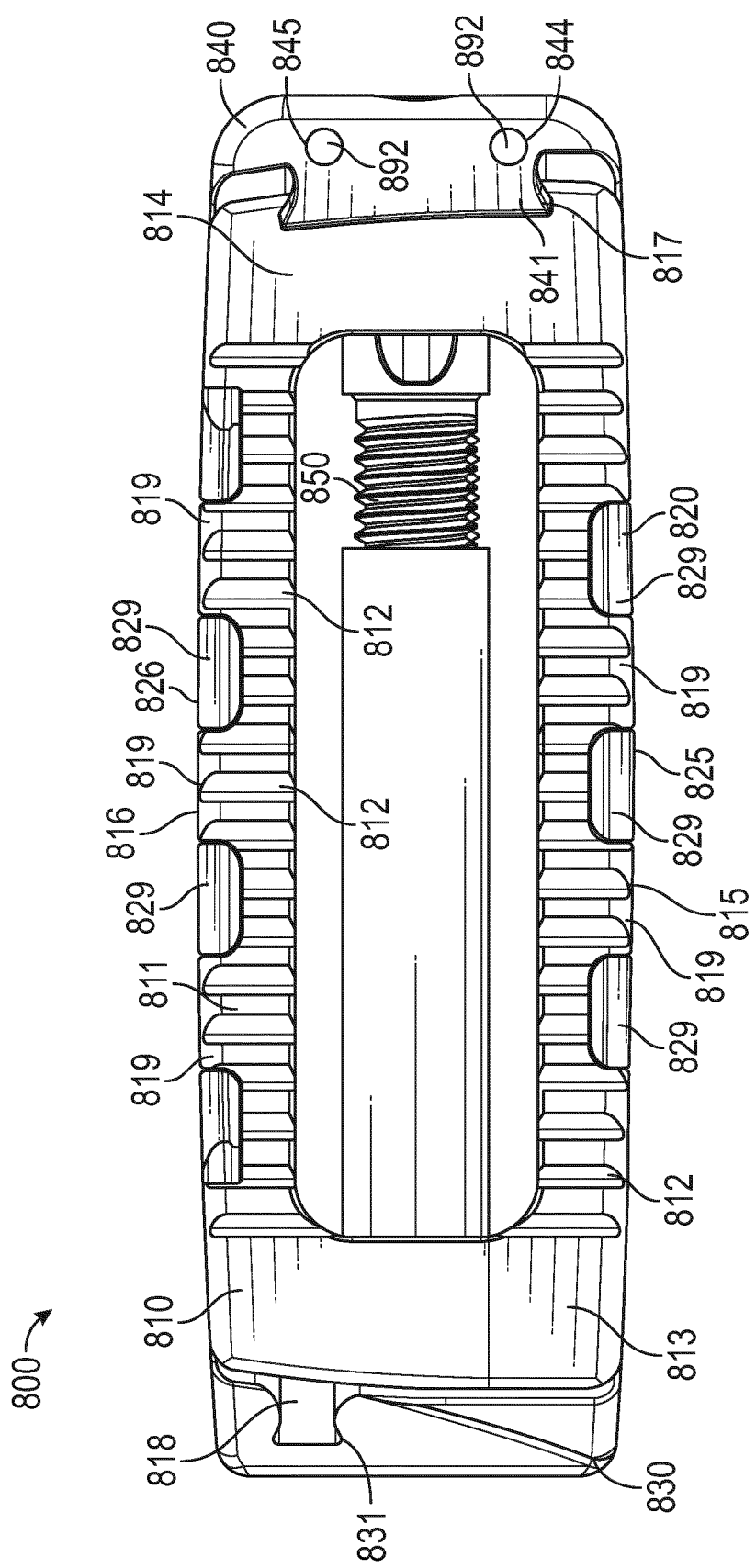
FIG. 93 shows a top view of the expandable implant of FIG. 92.
Figure 94:
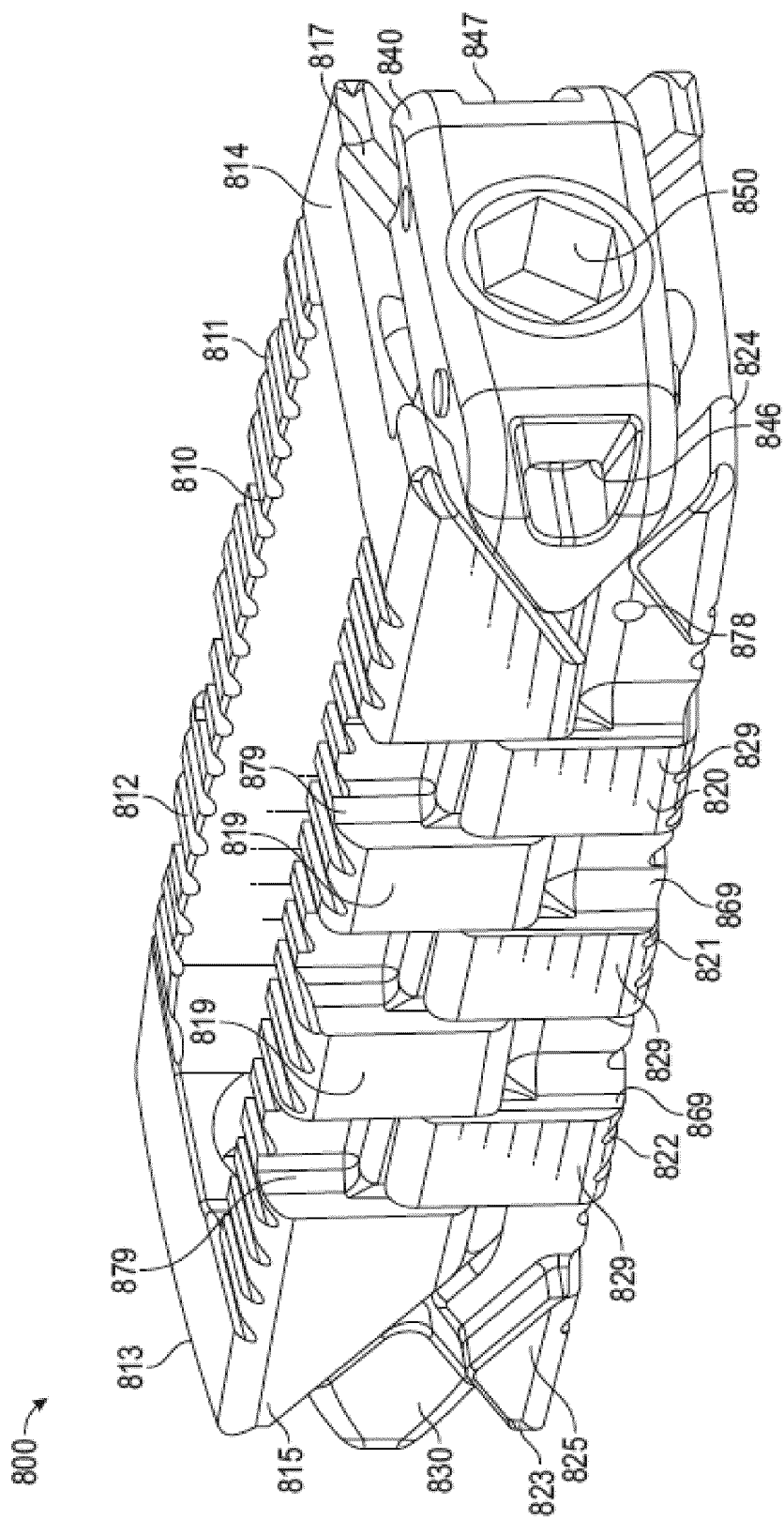
FIG. 94 shows another perspective view of the expandable implant of FIG. 92.
Figure 95:
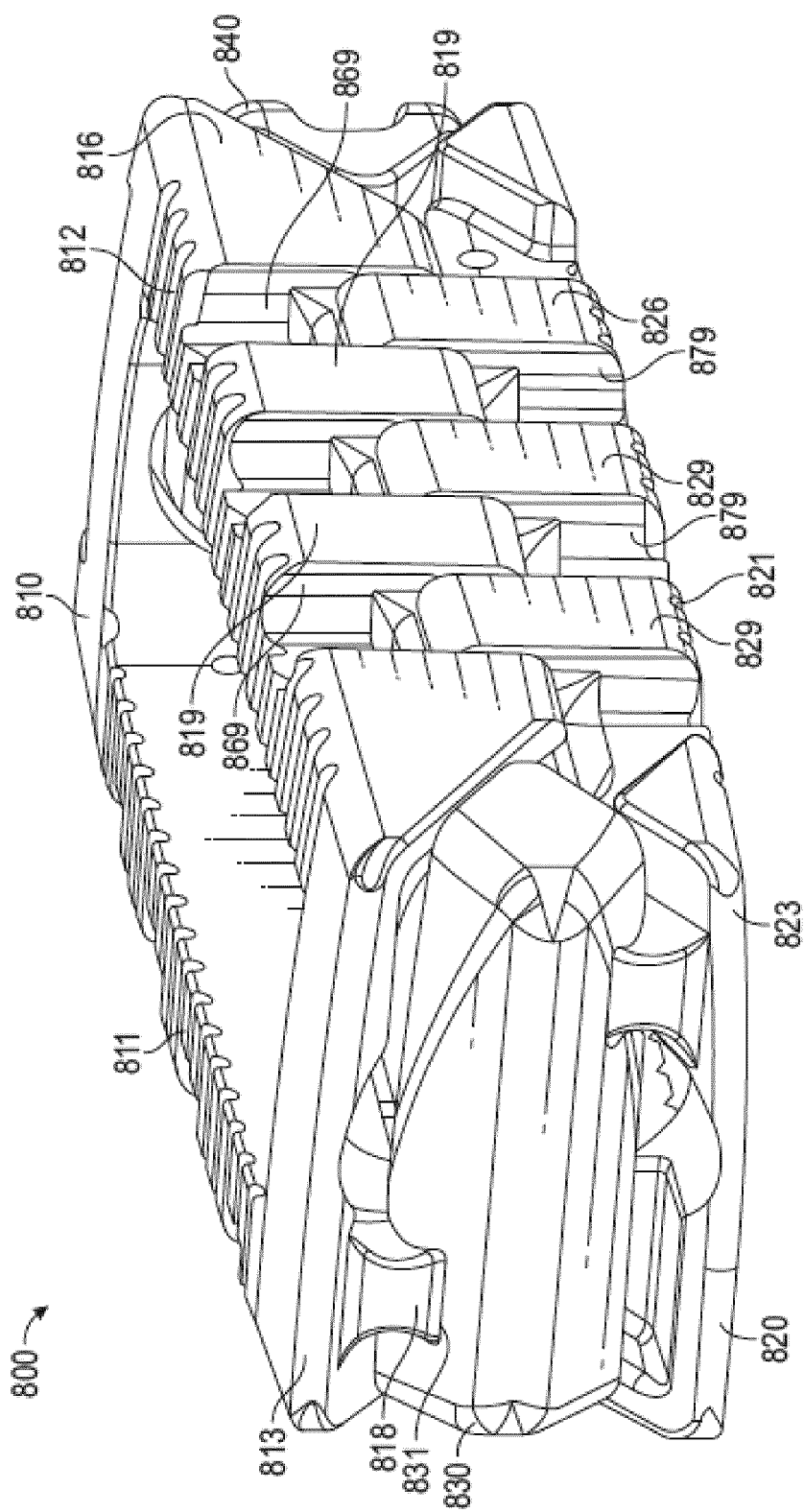
FIG. 95 shows another perspective view of the expandable implant of FIG. 92.

As will be discussed herein, the implant 800 is expandable between at least a first, collapsed orientation and a second, expanded orientation. For example, the implant 800 shown in FIGS. 92 and 93 is shown in the first, collapsed orientation according to some embodiments. Further, the implant 800 shown in FIGS. 94 and 95 is shown in the second, expanded orientation. The first, collapsed orientation does not necessarily require the implant 800 to be completely collapsed and the second, expanded orientation does not require the implant 800 to be completely expanded. Instead, the first, collapsed orientation and the second, expanded orientation may fall anywhere in-between the fully collapsed orientation and the fully expanded orientation, and including the fully collapsed orientation and the fully expanded orientation.

According to an exemplary embodiment, the implant 800 includes a first, or rear portion 840, a second, or front portion 830, and a third, intermediate, or control member or portion 850, which collectively form a control assembly 890 (see FIG. 97) that extends along a longitudinal axis of the implant 800. A first, or top portion 810 (e.g., an upper plate or support member, etc.) and a second, bottom portion 820 (e.g., a lower plate or support member), are coupled to the body or control assembly 890 and may extend generally between rear portion 840 and the front portion 830.

In some embodiments, the rear portion 840 includes an aperture 843 (see FIG. 97) configured to enable the control member 850 to extend through the rear portion 840 and into a central cavity of the implant 800. The rear portion 840 may also include a plurality of apertures configured to receive retention members. For example, the rear portion 840 may include a first aperture 844 proximate a first lateral portion of the rear portion 840 and a second aperture 845 proximate a second lateral portion of the rear portion 840 (see FIG. 97). The first aperture 844 and the second aperture 845 may extend from a top surface of the rear portion 840 to a bottom surface of the rear portion 840. The first aperture 844 and the second aperture 845 may be configured to individually receive a retention member 892 as will be discussed further herein. Further, the rear portion 840 may include an installation tool interface 846, 848. For example, the rear portion 840 may include a first installation tool interface 846 on a first side and a second installation tool interface 848 on a second side. An installation tool may be used to grab the first installation tool interface 846 and the second installation tool interface 847 in order to secure the implant 800 to the installation tool so that the implant 800 can be inserted into a person.

The top portion 810 may have an upper surface 811. In some embodiments, such as shown in FIG. 92, the upper surface 811 has a plurality of ridges and/or grooves 812. The plurality of ridges and/or grooves 812 may provide a surface roughness that will increase the stability of the implant 800 once inserted into a person. Similarly, the bottom portion 820 may have a lower surface 821. In some embodiments, such as shown in FIG. 93, the lower surface 821 has a plurality of ridges and/or grooves 822. The plurality of ridges and/or grooves 812 may provide a surface roughness that will increase the stability of the implant 800 once inserted into a person. Further, in some embodiments, the top portion 810 and the bottom portion 820 may be identical. In some embodiments, this may reduce the cost of manufacturing the implant 800.

According to an exemplary embodiment, the upper surface 811 and lower surface 821 define a height of the implant 800 (e.g., a support height defined by the vertical distance between the upper surface 811 of the top portion 810 and the lower surface 821 of the bottom portion 820). In some embodiments, the height of the implant 800 may be constant throughout the implant 800. However, in some embodiments, the height of the implant 800 is generally greater near the center of the implant 800 than the height near the rear portion 840 and the front portion 830. It should be appreciated that the height and general profile of the implant 800 may be customized based on the needs of the person the implant 800 is being inserted into.

In some embodiments, the implant 800 defines a longitudinal axis extending along the control member 850. The top portion 810 defines a rear or first end 814, a front or second end 813 opposite the rear or first end 814, a first side 815, and a second side 816 opposite the first side 815. The first end 814 and the second end 813 define an overall taper to upper surface 811. In some embodiments, the upper surface 811 may define an arcuate shape between the first end 814 and the second end 813 (e.g., such that the upper surface 811 has a slight curvature, such as a parabolic curve, between the first end 814 and the second end 813 when viewed from the first side 815). In other embodiments, the upper surface 811 may define a substantially planar surface between the first end 814 and the second end 813.

The bottom portion 820 defines a first end 824, a second end 823, a first side 825 and a second side 826. The lower surface 821 extends between the first end 824 and the second end 823. The first end 824 and the second end 823 define an overall taper to lower surface 821. In some embodiments, lower surface 821 may define an arcuate shape between the first end 824 and the second end 823 (e.g., such that the lower surface 821 has a slight curvature, such as a parabolic curve, between the first end 824 and the second end 823 when viewed from the first side 825). In other embodiments, the lower surface 821 may define a substantially planar surface between the first end 824 and the second end 823.

As shown in FIGS. 92-95, the top portion 810 and the bottom portion 820 move toward and away from each other in a linear manner, such that the degree of taper remains constant and the implant 800 expands from the first, collapsed position to the second, expanded position. In other embodiment, other configurations may be utilized to provide non-linear movement and a varying longitudinal taper.

Referring now to FIG. 93, the top portion 810 may include a cutout 817 at the first end 814. In certain embodiments, the cutout 817 is generally dovetail shaped and is centered between the first side 815 and the second side 816. The cutout 817 is configured to receive a projection 841 of the rear portion 840. In certain embodiments, the projection 841 is generally dovetail shaped. As the implant 800 expands from the first, collapsed position to the second, expanded position, the projection 841 will slide within the cutout 817. Further, the top portion 810 may include a rail 818 at the second end 813. The rail 818 may be configured to be received by a groove 831 in the front portion 830. As the implant 800 expands from the first, collapsed position to the second, expanded position, the rail 818 may slide within the groove 831. In certain embodiments, the rail 818 is off-center and is closer to the second side 816 than the first side 815. In certain embodiments, the rail 818 is generally dovetail shaped and the groove 831 is generally dovetail shaped.

The top portion 810 may also include a plurality of side projections 819 on the first side 815 and the second side 816 between the first end 814 and the second end 813. For example, in the embodiment shown in FIGS. 92-85, the top portion 810 has two projections 819 on the first side 815 and 3 projections 819 on the second side. The side projections 819 may be configured to be received by a plurality of corresponding slots 879 on the first side 825 and the second side 826 of the bottom portion 820. When the implant 800 expands from the first, collapsed position to the second, expanded position, the projections 819 may slide within the slots 879. The side projections 819 may provide the implant 800 with additional lateral stability to prevent the top portion 810 shifting laterally with respect to the bottom portion 820.

Figure 96:
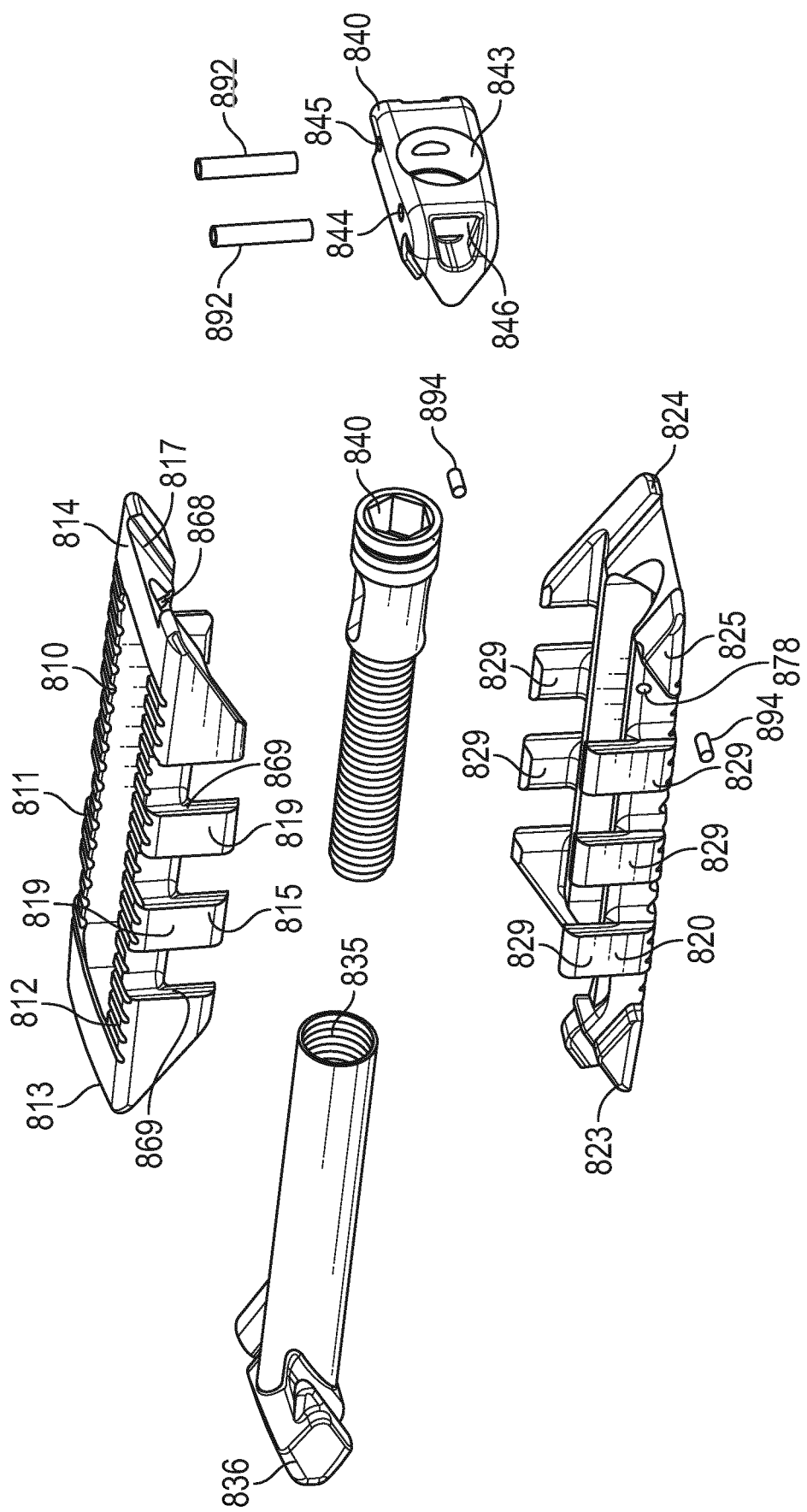
FIG. 96 shows an exploded view of the expandable implant of FIG. 92.

Referring now to FIGS. 94 and 96, the bottom portion 820 may include a cutout 827 at the first end 824. In certain embodiments, the cutout 827 is generally dovetail shaped and is centered between the first side 825 and the second side 826. The cutout 827 is configured to receive a projection 842 of the rear portion 840. In certain embodiments, the projection 842 is generally dovetail shaped. As the implant 800 expands from the first, collapsed position to the second, expanded position, the projection 842 will slide within the cutout 827. Further, the bottom portion 820 may include a rail 828 at the second end 823. The rail 828 may be configured to be received by a groove 832 in the front portion 830. As the implant 800 expands from the first, collapsed position to the second, expanded position, the rail 828 may slide within the groove 832. In certain embodiments, the rail 828 is off-center and is closer to the first side 825 than the second side 826. In certain embodiments, the rail 828 is generally dovetail shaped and the groove 831 is generally dovetail shaped.

The bottom portion 820 may also include a plurality of side projections 829 on the first side 825 and the second side 826 between the first end 824 and the second end 823. The side projections 829 may be configured to be received by a plurality of slots 869 on the first side 815 and the second side 816 of the top portion 810. When the implant 800 expands from the first, collapsed position to the second, expanded position, the projections 829 may slide within the slots 869. The side projections 829 may provide the implant 800 with additional lateral stability to prevent the top portion 810 shifting laterally with respect to the bottom portion 820.

Referring now to FIG. 96, in some embodiments, the implant 800 includes one or more retaining members to prevent undesired expansion and/or collapsing of the implant 800. For example, once the implant 800 is set to a desired height, a first retention member 894 may be driven (e.g., press fit) into a first pin aperture 868 on the second side 816 of the top portion. Additionally, a second retention member 894 may be driven (e.g., press fit) into a second pin aperture 878 on the first side 825 of the bottom portion 820. In doing so, the retention members 894 may extend into the center cavity of the implant 800, thereby preventing the rear portion 840 from moving closer to the front portion 830, thereby preventing over expansion of the implant 800. Additionally, the retention members 894 may prevent the implant 800 from collapsing by preventing the bottom portion 820 and the top portion 810 from returning to the first, collapsed position. In various alternative embodiments, retaining members may be used that extend through other portions, such as opposing top and bottom sides. Further, as will be discussed below, in some embodiments, the implant 800 may include additional retention members, such as the retention members 892.

Figure 97:
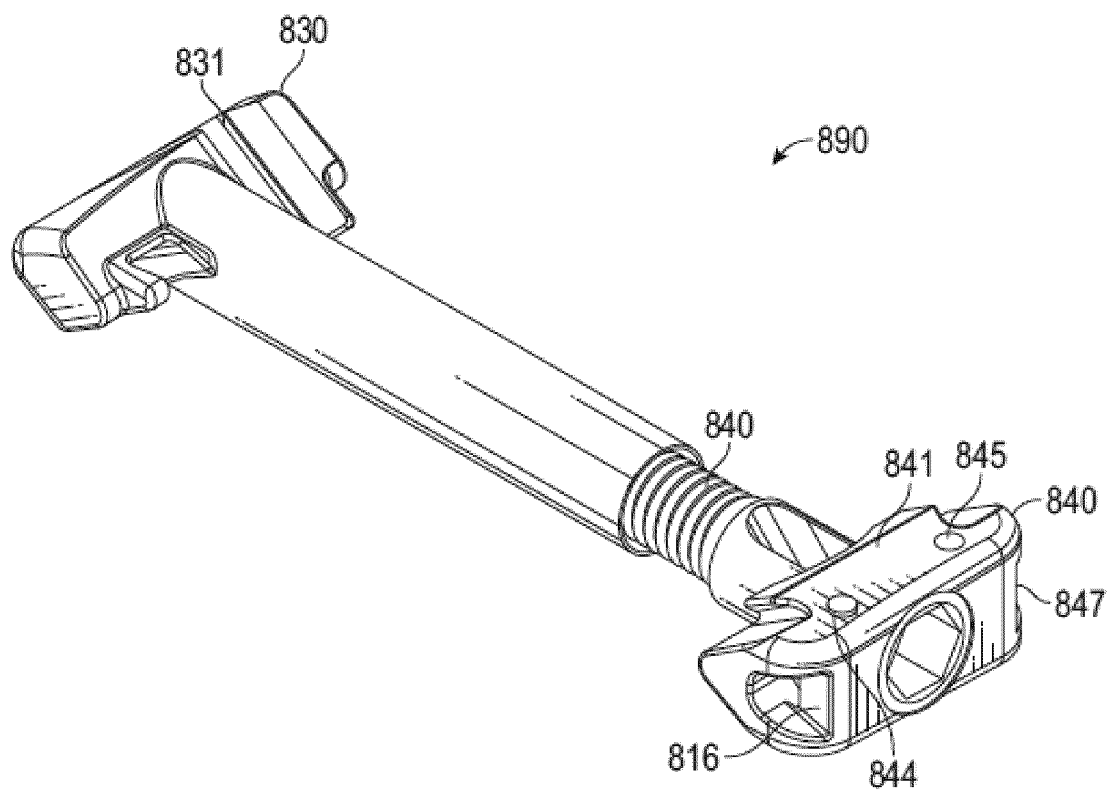
FIG. 97 shows a perspective view of a control assembly according to an example embodiment.
Figure 98:
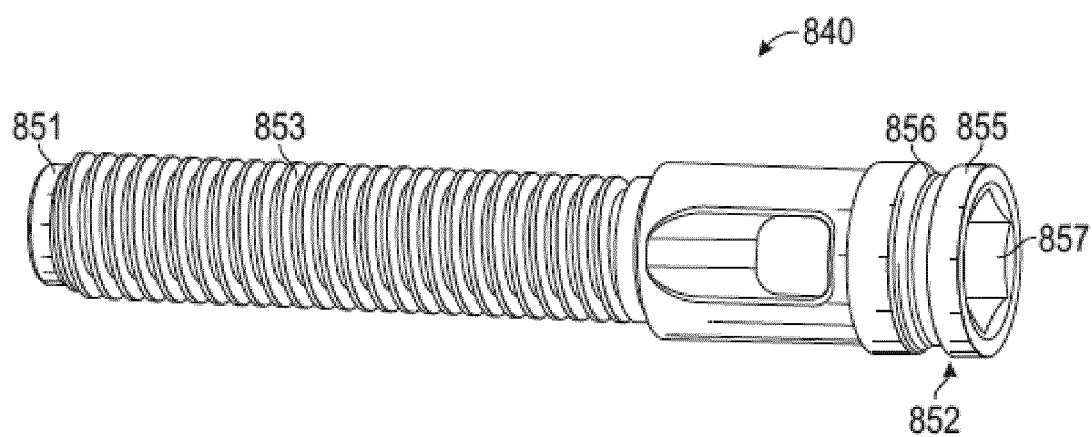
FIG. 98 shows a perspective view of a control member according to an example embodiment.

Referring now to FIG. 97, the control assembly 890 is shown according to an example embodiment. The control assembly includes the rear portion 840 adjustably coupled to the front portion 830 by the control member 850. As shown in FIG. 98, the control member 850 includes a head portion 851, a tip 852 opposite the head portion 851, and a threaded shaft 853 positioned between the head portion 851 and the tip 852. The head portion 851 further includes an access ring 855, a retention groove 856 in the access ring 855, and a tool port 857 configured to receive a tool that may be used to manipulate the control member 850 to cause expansion of the implant 800. The access ring 855 may have a smaller exterior diameter than the inner diameter of the aperture 843 so that a portion of the head portion 851 may be received by the aperture 843. Further, the retention groove 856 may have an exterior diameter smaller than the exterior diameter of the access ring 855 so that a retention member (e.g., retention member 892) may be inserted into the retention groove 856.

After the implant 800 is inserted, the control assembly 890 may be used to expand the implant 800 from the first, collapsed position to the second, expanded position. For example, a person may use an expansion tool that engages with the tool port 857 of the control member 850. For example, the expansion tool may be a hex head screwdriver. A person, such as a surgeon or doctor, may then use the expansion tool to turn the control member 850, for example, in a clockwise direction. In this example embodiment, the threaded shaft 853 is received by a threaded bore 835 of the front portion 830 (see FIG. 96). As the control member 850 is turned, the tip 852 will continue to move further into the threaded bore 835. For example, turning the control member 850 in a clockwise direction will cause the head portion 851 of the control member 850 to move in a direction towards the front portion 830. Since the retention members 892 couple the rear portion 840 to the control member 850, as the head portion 851 moves closer to the front portion 830, the rear portion 840 will also move closer to the front portion 830. As the front portion 830 and the rear portion 840 move near each other, ramped surfaces of the front portion 830 and the rear portion 840 slidably engage the top portion 810 and the bottom portion 820, thereby causing the top portion 810 and the bottom portion 820 to move linearly away from each other. It should be appreciated that, while the Figures generally show control member 850 threadingly engaging front portion 830, in other embodiments, other adjustment mechanisms may be used (e.g., ratchet mechanisms, indents/detents, etc.). In these embodiments, the control member 850 may be manipulated (e.g., urged, turned, pushed, rotated, etc.) to control relative movement between the top portion 810 and the bottom portion 820.

Further, it should be appreciated that the expansion profile of an implant may be customized in part by changing the angles of the various ramped surfaces. Using the implant in various locations may require a custom expansion profile. For example, if the implant is inserted into a patient's spine, the implant expansion profile may be customized to match the curvature of the patient's spine at the desired location that the implant is to be implanted into. In some example embodiments, the ramped surfaces of the rear portion 840 may have a much higher angle (i.e., the angle that upward angled surface and the downward angle surface form) than the ramped surfaces of the front portion 830. In this example embodiment, turning the control member 850 will cause the implant 800 to expand more near the rear portion 840 than near the front portion 830. In this example embodiment, the implant 800 height will be larger near the rear portion 840 than near the front portion 830. It should be appreciated that further customization of the expansion profile of an implant 800 may be accomplished by adjusting the angle of ramped surfaces on the rear portion 840, the front portion 830, the top portion 810, and the bottom portion 820.

Further, retention members 892 may be used to prevent back-out of the control member 850. For example, if the implant 800 is compressed (i.e., a downward force on the upper surface 811 and an upward force on the lower surface 821), the control member 850 may experience forces that would force the control member 850 away from the front portion 830. To prevent this, a retention member 892 may be inserted into the first aperture 844 and the second aperture 845 of the rear portion 840. A portion of the retention members 892 may then be positioned within the retention groove 856 in the access ring 855 such that a portion of the retention members 892 is positioned within the first aperture 844 or the second aperture 845 and the retention groove 856, thereby preventing the control member 850 from backing out of the rear portion 840.

Referring now to FIGS. 99-104, an implant 900 is shown according to an exemplary embodiment. The implant 900 is usable, for example, between and/or within vertebral bodies of the spine, and may share many of the features of the other inter/intra-body implants discussed elsewhere herein. It should be understood that the implant 900 may in some embodiments be usable in other portions of the body in addition to the spine, and all such applications are to be understood to be within the scope of the present disclosure. The implant 900 is similar to the implants 260, 410, 460, 510, 700, and 800 and the other implants described herein, in structure and function except as discussed below. As such, the implant 900 is understood to include any or all of the features of the other implants described herein to the extent consistent with the additional features of the implant 900 described herein (e.g., retention pins, dovetail projections and ramped surfaces, alignment features, control member access port(s), etc.).

As will be discussed herein, the implant 900 is expandable between at least a first, collapsed orientation and a second, expanded orientation. For example, the implant 900 shown in FIGS. 99-104 is shown in the second, expanded orientation. The first, collapsed orientation does not necessarily require the implant 900 to be completely collapsed and the second, expanded orientation does not require the implant 900 to be completely expanded. Instead, the first, collapsed orientation and the second, expanded orientation may fall anywhere in-between the fully collapsed orientation and the fully expanded orientation, and including the fully collapsed orientation and the fully expanded orientation.

According to an exemplary embodiment, the implant 900 includes a first, or rear portion 940, a second, or front portion 930, and a third, intermediate, or control member or portion 950, which collectively form a control assembly that extends along a longitudinal axis of the implant 900. A first, or top portion 910 (e.g., an upper plate or support member, etc.) and a second, bottom portion 920 (e.g., a lower plate or support member), are coupled to the body or control assembly and may extend generally between rear portion 940 and the front portion 930.

In some embodiments, the rear portion 940 includes an aperture 943 (see FIG. 105) configured to enable the control member 950 to extend through the rear portion 940 and into a central cavity of the implant 900. The rear portion 940 may also include a one or more apertures configured to receive retention members, such as a retention pin 992. For example, the rear portion 740 may include a first aperture 944 proximate a first lateral side of the rear portion 940. The first aperture 944 may be configured to receive a retention pin 992 as will be discussed further herein. The rear portion 740 may include a second aperture 944 proximate a second lateral side of the rear portion 940. The second aperture 944 may be configured to receive a retention pin 992 as will be discussed further herein. Further, the rear portion 940 may include an installation tool interface 946, 947. For example, the rear portion 940 may include a first installation tool interface 946 on a first lateral side and a second installation tool interface 947 on a second side. An installation tool may be used to grab the first installation tool interface 946 and the second installation tool interface 947 in order to secure the implant 900 to the installation tool so that the implant 900 can be inserted into a person.

Figure 102:
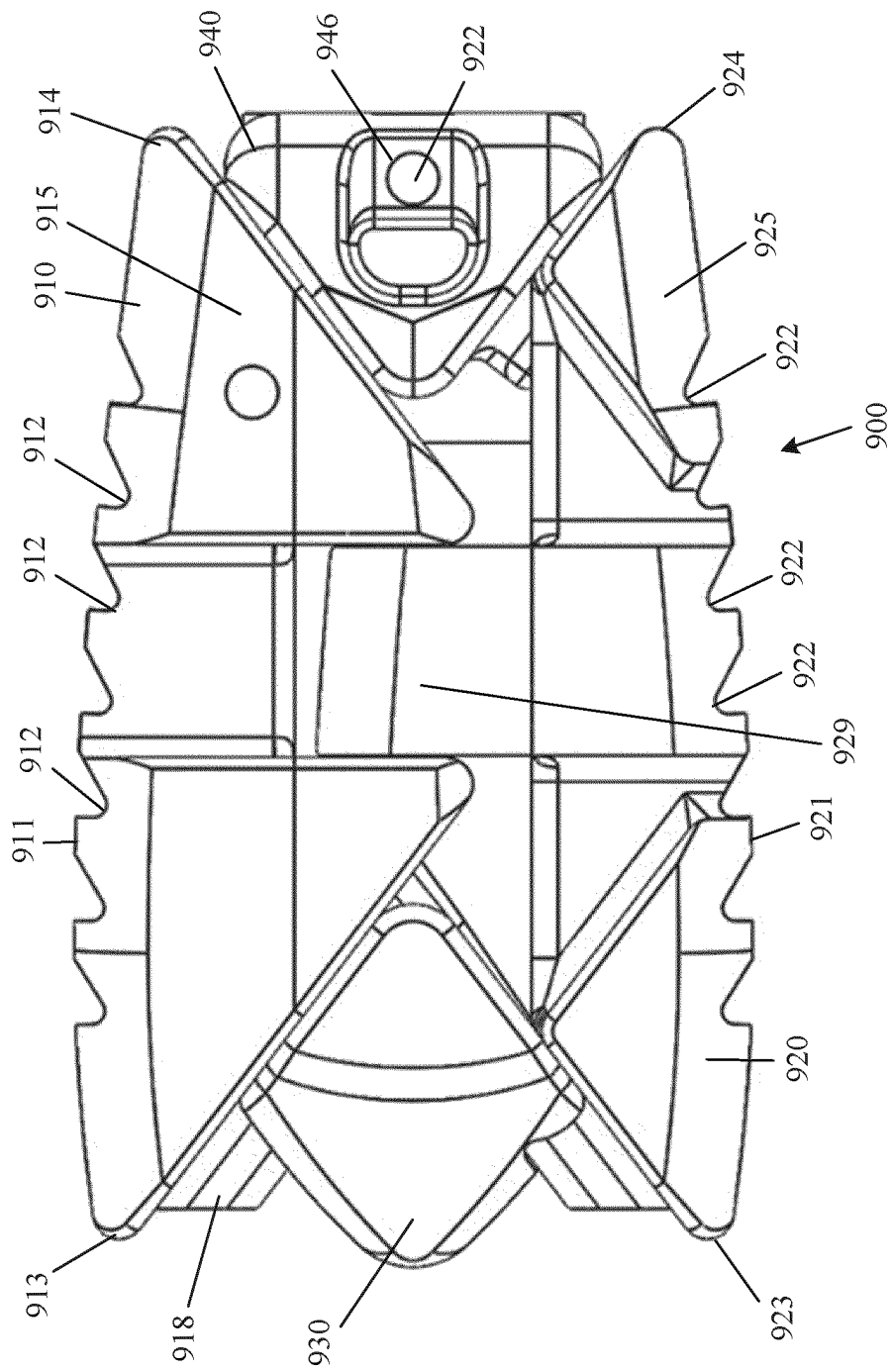
FIG. 102 shows another perspective view of the implant of FIG. 99 according to an example embodiment.

The top portion 910 may have an upper surface 911. In some embodiments, such as shown in FIG. 102, the upper surface 911 has a plurality of ridges and/or grooves 912. The plurality of ridges and/or grooves 912 may provide a surface roughness that will increase the stability of the implant 900 once inserted into a person. Similarly, the bottom portion 920 may have a lower surface 921. In some embodiments, such as shown in FIG. 102, the lower surface 921 has a plurality of ridges and/or grooves 922. The plurality of ridges and/or grooves 912 may provide a surface roughness that will increase the stability of the implant 900 once inserted into a person. Further, in some embodiments, the top portion 910 and the bottom portion 920 may be identical. In some embodiments, this may reduce the cost of manufacturing the implant 900.

According to an exemplary embodiment, the upper surface 911 and lower surface 921 define a height of the implant 900 (e.g., a support height defined by the vertical distance between the upper surface 911 of the top portion 910 and the lower surface 921 of the bottom portion 920). In some embodiments, the height of the implant 900 may be constant throughout the implant. However, in the embodiment shown in FIG. 102, the height of the implant is generally greater near the center of the implant 900 than the height near the front portion 930 and the height near the rear portion 940. In some embodiments, such as shown in FIG. 102, the upper surface 911 and the lower surface 921 are generally arched when viewed from the side. It should be appreciated that the height and general profile of the implant 900 may be customized based on the needs of the person the implant 900 is being inserted into.

In some embodiments, the implant 900 defines a longitudinal axis extending along the control member 950. The top portion 910 defines a rear or first end 914, a front or second end 913 opposite the rear or first end 914, a first lateral side 915, and a second lateral side 916 opposite the first side 915. The first end 914 and the second end 913 define an overall taper to the upper surface 911. In some embodiments, the upper surface 911 may define an arcuate shape between the rear or first end 914 and the second end 913 (e.g., such that the upper surface 911 has a slight curvature, such as a parabolic curve, between the first end 914 and the second end 913 when viewed from the first lateral side 915). In other embodiments, the upper surface 911 may define a substantially planar surface between the first end 914 and the second end 913.

The bottom portion 920 defines a first end 924, a second end 923, a first side 925 and a second side 926. The lower surface 921 extends between the first end 924 and the second end 923. The first end 924 and the second end 923 define an overall taper to lower surface 921. In some embodiments, lower surface 921 may define an arcuate shape between the first end 924 and the second end 923 (e.g., such that the bottom surface 921 has a slight curvature, such as a parabolic curve, between the first end 924 and the second end 923 when viewed from the first side 925). In other embodiments, the bottom surface 921 may define a substantially planar surface between the first end 924 and the second end 923.

In use, the top portion 910 and the bottom portion 920 are configured to move toward and away from each other in a linear manner, such that the degree of taper remains constant and the implant 900 expands from the first, collapsed position to the second, expanded position. In other embodiment, other configurations may be utilized to provide non-linear movement and a varying longitudinal taper. Furthermore, while FIGS. 99-104 illustrate an implant having a parabolic longitudinal taper, according to various alternative embodiments, implants may be provided having a variable longitudinal taper. Further, in various alternative embodiments, the implant may taper from the first lateral side to the second lateral side, or vice versa.

Figure 104:
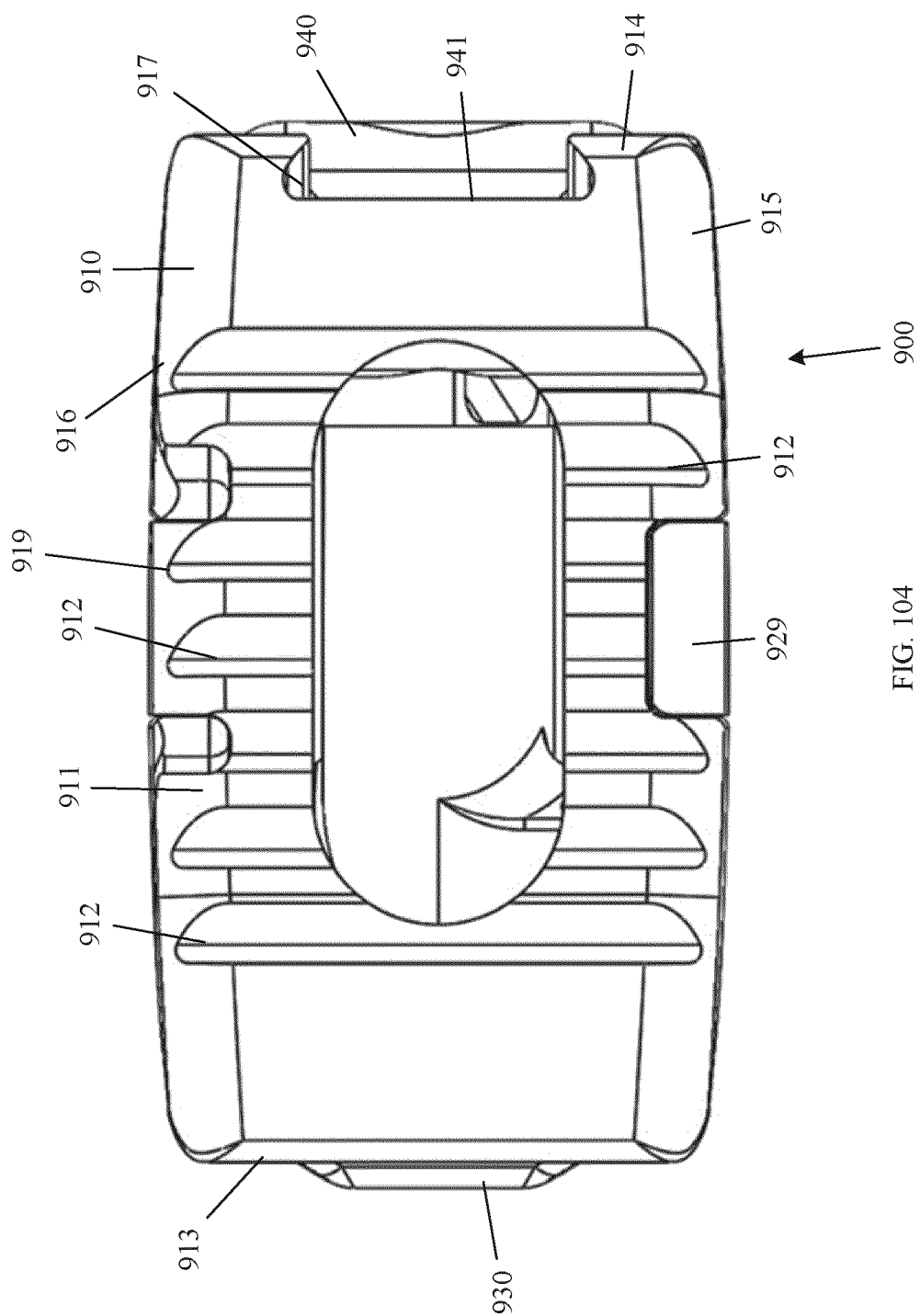
FIG. 104 shows another perspective view of the implant of FIG. 99 according to an example embodiment.
Figure 105:
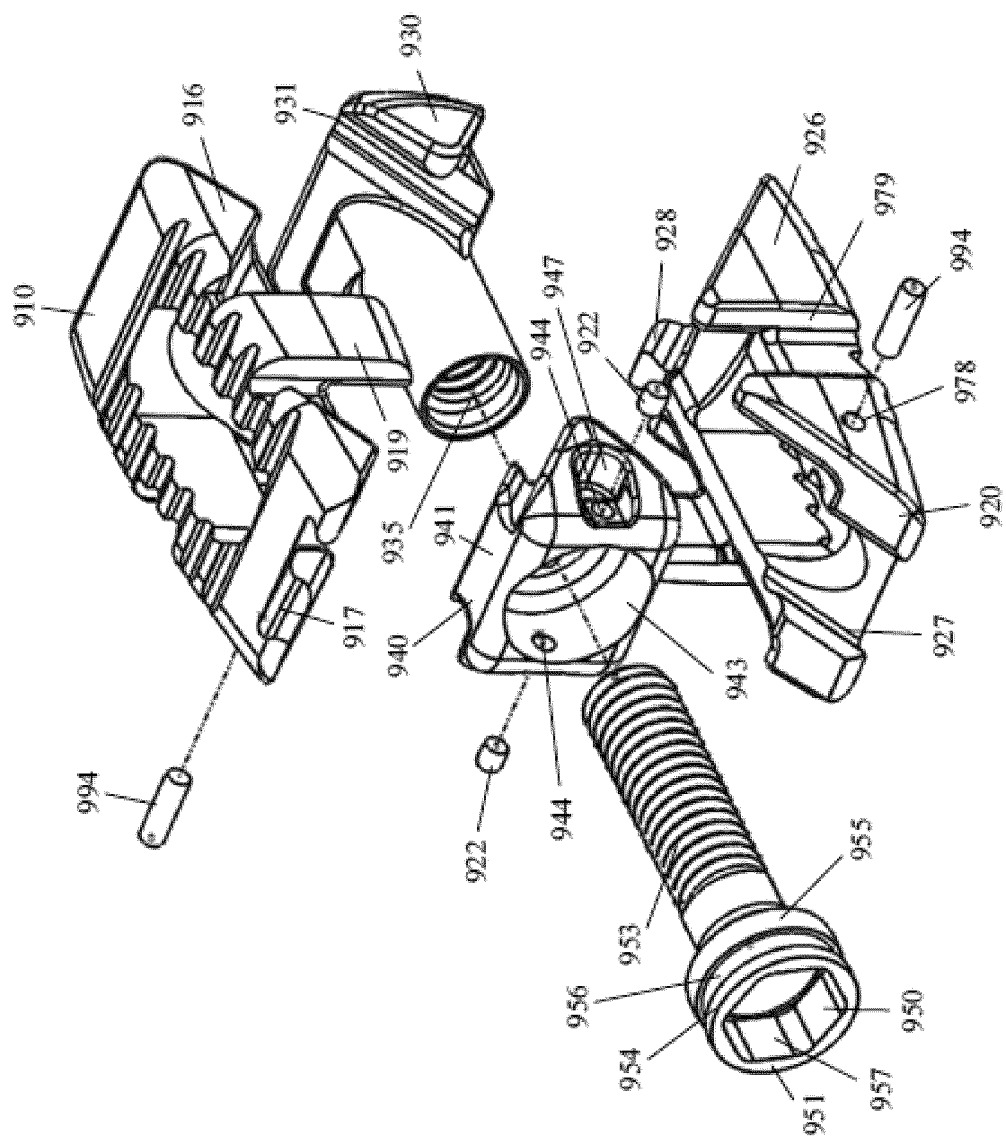
FIG. 105 shows an exploded view of the implant of FIG. 99 according to an example embodiment.

Referring now to FIGS. 104 and 105, the top portion 910 may include a cutout 917 at the first end 914. In certain embodiments, the cutout 917 is generally dovetail shaped and is centered between the first side 915 and the second side 916. The cutout 917 is configured to receive a projection 941 of the rear portion 940. In certain embodiments, the projection 941 is generally dovetail shaped. As the implant 900 expands from the first, collapsed position to the second, expanded position, the projection 941 will slide within the cutout 917.

Figure 100:
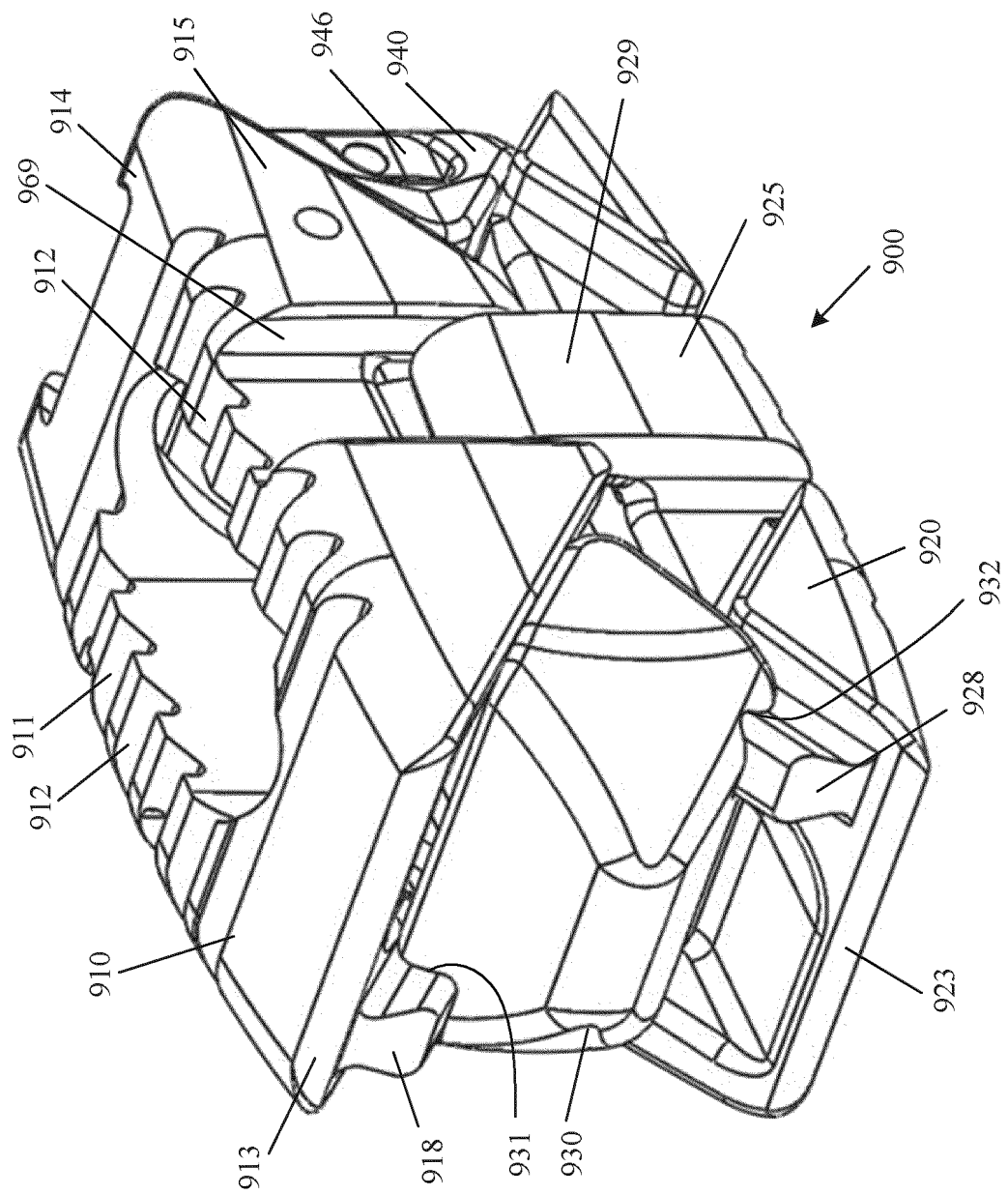
FIG. 100 shows another perspective view of the implant of FIG. 99 according to an example embodiment.
Figure 101:
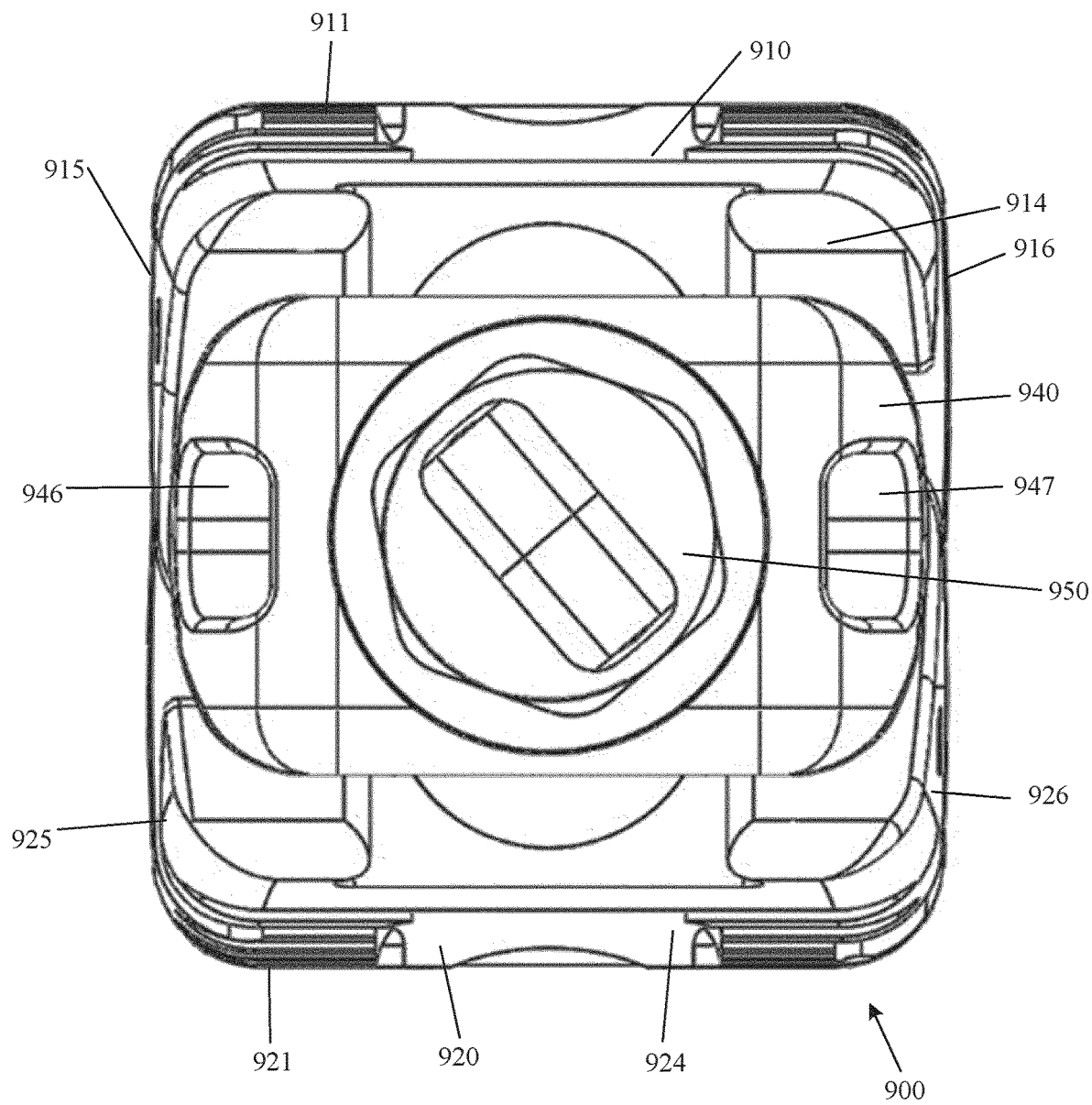
FIG. 101 shows another perspective view of the implant of FIG. 99 according to an example embodiment.

Referring now to FIG. 100, the top portion 910 may include a rail 918 at the second end 913. The rail 918 may be configured to be received by a groove 931 in the front portion 930. As the implant 900 expands from the first, collapsed position to the second, expanded position, the rail 918 may slide within a groove 931 in the front portion 930. In certain embodiments, the rail 918 is off-center and is closer to the second side 916 than the first side 915. In certain embodiments, the rail 918 is generally dovetail shaped and the groove 931 is generally dovetail shaped.

Referring now to FIGS. 104 and 105, the top portion 910 may also include a side projection 919 on the second lateral side 916 between the first end 914 and the second end 913. The side projection 919 may be configured to be received by a slot 979 on the first side 925 of the bottom portion 920. When the implant 900 expands from the first, collapsed position to the second, expanded position, the projection 919 may slide within the slot 979. The side projection 919 may provide the implant 900 with additional lateral stability to prevent the top portion 910 shifting laterally with respect to the bottom portion 920.

Figure 106:
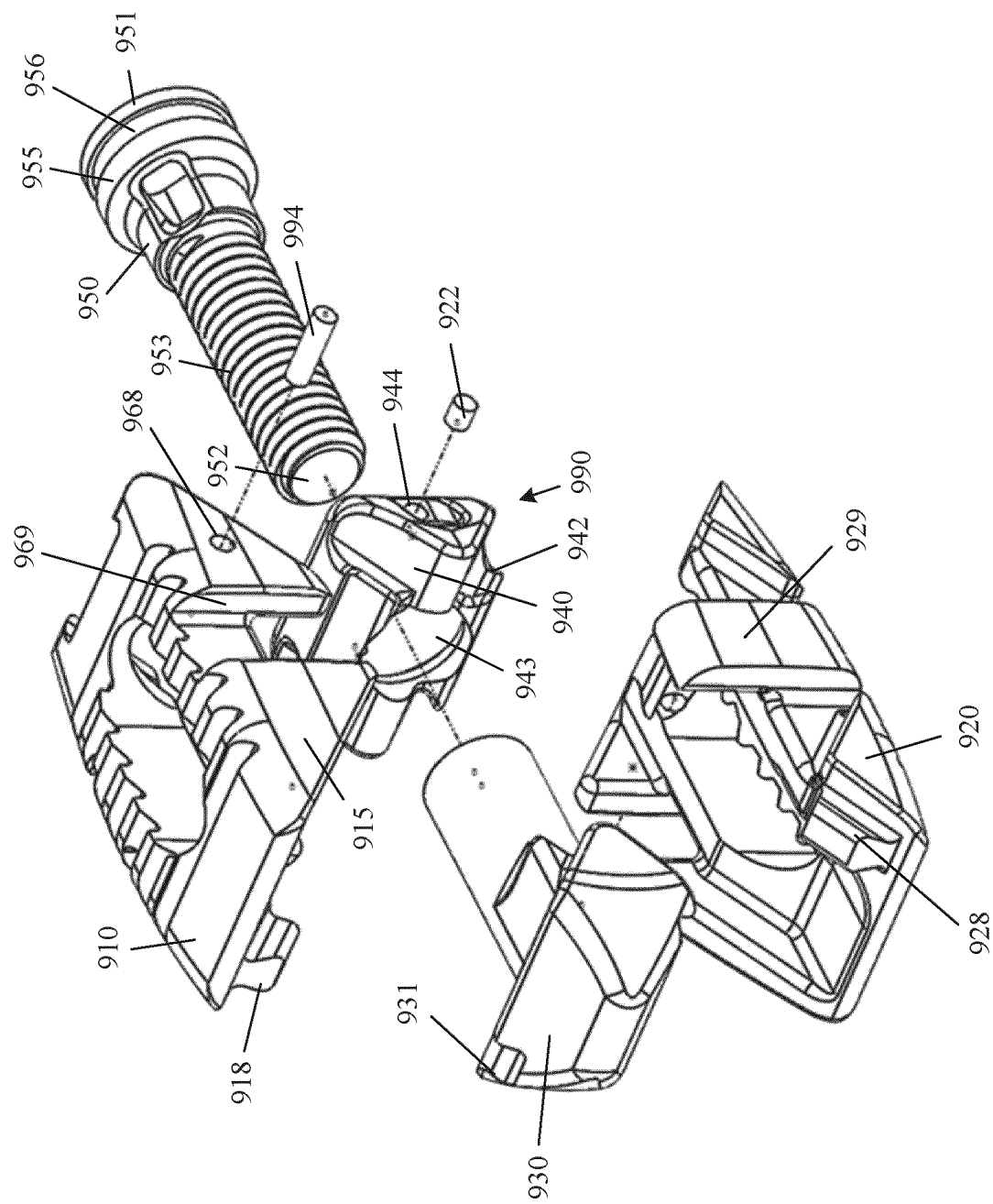
FIG. 106 shows a perspective view of the implant of FIG. 99 according to an example embodiment.

Referring now to FIGS. 105 and 106, the bottom portion 920 may include a cutout 927 at the first end 924. In certain embodiments, the cutout 927 is generally dovetail shaped and is centered between the first side 925 and the second side 926. The cutout 927 is configured to receive a projection 942 of the rear portion 940. In certain embodiments, the projection 942 is generally dovetail shaped. As the implant 900 expands from the first, collapsed position to the second, expanded position, the projection 942 will slide within the cutout 927.

Figure 103:
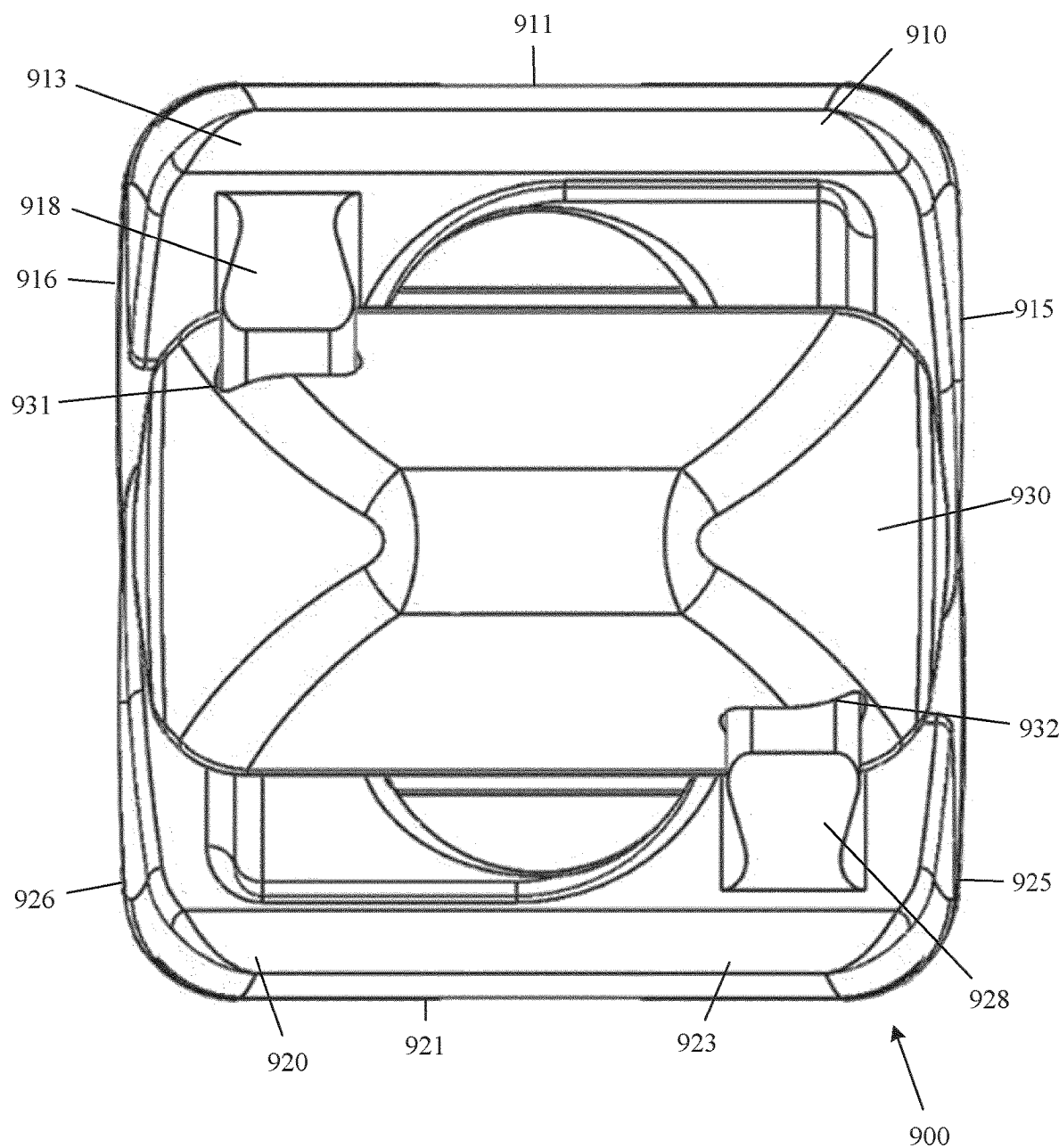
FIG. 103 shows another perspective view of the implant of FIG. 99 according to an example embodiment.

Referring now to FIGS. 103 and 106, the bottom portion 920 may include a rail 928 at the second end 923. The rail 928 may be configured to be received by a groove 932 in the front portion 930. As the implant 900 expands from the first, collapsed position to the second, expanded position, the rail 928 may slide within the groove 932. In certain embodiments, the rail 928 is off-center and is closer to the first side 925 than the second side 926. In certain embodiments, the rail 928 is generally dovetail shaped and the groove 932 is generally dovetail shaped.

Figure 99:
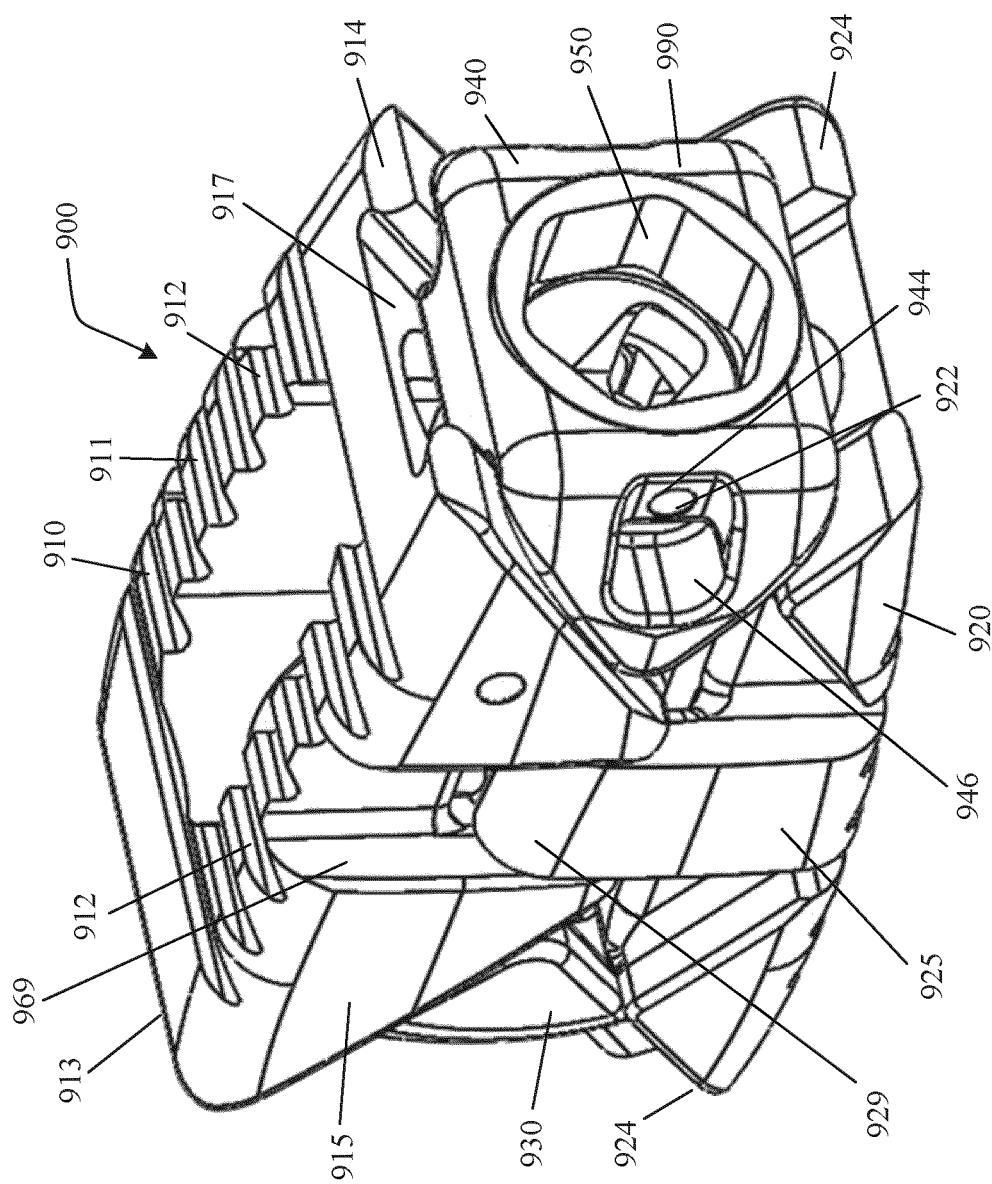
FIG. 99 shows a perspective view of an implant according to another example embodiment.

Referring now to FIGS. 99 and 106, the bottom portion 920 may also include a side projection 929 on the first side 925 between the first end 924 and the second end 923. The side projection 929 may be configured to be received by a slot 969 on the first side 915 of the top portion 910. When the implant 900 expands from the first, collapsed position to the second, expanded position, the projection 929 may slide within the slot 969. The side projection 929 may provide the implant 900 with additional lateral stability to prevent the top portion 910 shifting laterally with respect to the bottom portion 920.

Referring now to FIGS. 105 and 106, in some embodiments, the implant 900 includes one or more retaining members to prevent undesired expansion and/or collapsing of the implant 900. For example, once the implant 900 is set to a desired height, a first retention pin 994 may be driven (e.g., press fit) into a first pin aperture 968 on the first side 915 of the top portion. Additionally, a second retention pin 994 may be driven (e.g., press fit) into a second pin aperture 978 on the second side 926 of the bottom portion 920. In doing so, the retention pins 994 may extend into the center cavity of the implant 900, thereby preventing the rear portion 940 from moving closer to the front portion 930, thereby preventing over expansion of the implant 900. Additionally, the retention pins 994 may prevent the implant 900 from collapsing by preventing the bottom portion 920 and the top portion 910 from returning to the first, collapsed position. In various alternative embodiments, retaining members may be used that extend through other portions, such as opposing top and bottom sides. Further, as will be discussed below, in some embodiments, the implant 900 may include additional retention members.

The control assembly includes the rear portion 940 adjustably coupled to the front portion 930 by the control member 950. As shown in FIGS. 105 and 106, the control member 950 includes a head portion 951, a tip 952 opposite the head portion 951, and a threaded shaft 953 positioned between the head portion 951 and the tip 952. The head portion 951 further includes an outer ring 954, an access ring 955, a retention groove 956 in the access ring 955, and a tool port 957 configured to receive a tool that may be used to manipulate the control member 950 to cause expansion of the implant 900. As shown, the outer ring 954 has an exterior diameter smaller than the inner diameter of the aperture 943. Therefore, as the head portion 951 moves closer to the front portion 930, the outer ring 954 will enter the aperture 943 of the rear portion 940, thereby causing the rear portion 940 to move closer to the front portion 930, causing expansion of the implant 900. The access ring 955 may have a smaller exterior diameter than the aperture 943. Further, the retention groove 956 may have an exterior diameter smaller than the exterior diameter of the access ring 955 so that a retention member (e.g., the retention pin 922) may be inserted into the retention groove 956. When the retention pin 922 is inserted into the retention groove 956, the retention pin 922 may prevent the control member 950 from backing out of the aperture 943.

After the implant 900 is inserted, the control assembly 990 may be used to expand the implant 900 from the first, collapsed position to the second, expanded position. For example, a person may use an expansion tool that engages with the tool port 957 of the control member 950. For example, the expansion tool may be a hex head screwdriver. A person, such as a surgeon or doctor, may then use the expansion tool to turn the control member 950, for example, in a clockwise direction. In this example embodiment, the threaded shaft 953 is received by a threaded bore 935 of the front portion 930 (see FIG. 105). As the control member 950 is turned, the tip 952 will continue to move further into the threaded bore 935. For example, turning the control member 950 in a clockwise direction may cause the head portion 951 of the control member 950 to move in a direction towards the front portion 930. Since the retention pins 922 are positioned within the aperture 944 and within the retention groove 956, the head 951 is secured within the aperture 943. Therefore, as the control member 950 moves towards the front member 930, the rear portion 940 will also move towards the front portion 930. As the front portion 930 and the rear portion 940 move near each other, ramped surfaces of the front portion 930 and the rear portion 940 slidably engage the top portion 910 and the bottom portion 920, thereby causing the top portion 910 and the bottom portion 920 to move linearly away from each other. It should be appreciated that, while the Figures generally show control member 950 threadingly engaging front portion 930, in other embodiments, other adjustment mechanisms may be used (e.g., ratchet mechanisms, indents/detents, etc.). In these embodiments, the control member 950 may be manipulated (e.g., urged, turned, pushed, rotated, etc.) to control relative movement between the top portion 910 and the bottom portion 920.

Further, it should be appreciated that the expansion profile of an implant may be customized in part by changing the angles of the various ramped surfaces. Using the implant in various locations may require a custom expansion profile. For example, if the implant is inserted into a patient's spine, the implant expansion profile may be customized to match the curvature of the patient's spine at the desired location that the implant is to be implanted into. In some example embodiments, the ramped surfaces of the rear portion 940 may have a much higher angle (i.e., the angle that upward angled surface and the downward angle surface form) than the ramped surfaces of the front portion 930. In this example embodiment, turning the control member 950 will cause the implant 900 to expand more near the rear portion 940 than near the front portion 930. In this example embodiment, the implant 900 height will be larger near the rear portion 940 than near the front portion 930. It should be appreciated that further customization of the expansion profile of an implant 900 may be accomplished by adjusting the angle of ramped surfaces on the rear portion 940, the front portion 930, the top portion 910, and the bottom portion 920.

Further, the retention pins 922 may be used to prevent back-out of the control member 950. For example, if the implant 900 is compressed (i.e., a downward force on the upper surface 911 and an upward force on the lower surface 921), the control member 950 may experience forces that would force the control member 950 away from the front portion 930. To prevent this, a retention pin 922 may be inserted into the first aperture 944 and the second aperture 944 of the rear portion 940. The retention pins 922 may then extend into the retention groove 956 such that a portion of the retention pin 922 is positioned within the first aperture 944 or the second aperture 944 and the retention groove 956, thereby preventing the control member 950 from backing out of the rear portion 940.

Referring now to the Figures generally, the various embodiments disclosed herein provide expandable implants including a lower support and an upper support adjustably coupled to the lower support and movable between a first, collapsed position, and a second, expanded position. Further, a front component and a control shaft rotatably received by the front component is disclosed, where rotation of the control shaft causes relative movement of a rear portion relative to the front component.

In some embodiments, the upper support moves in a linear fashion relative to the lower support. In other embodiments, the upper support may move in a non-linear fashion relative to the lower support. In some embodiments, a single control member and control shaft are utilized. In other embodiments, multiple (e.g., 2) control members and control shafts are utilized. In some embodiments, the multiple control channels are parallel and straight. In other embodiments, the control channels are non-parallel and straight (e.g., angled toward each other). In further embodiments, the control channels are non-parallel and non-straight such that the adjustable member moves in a non-linear fashion relative to the base member.

In some embodiments, the control shaft includes a control thread corresponding to each control member. As such, while in some embodiments the control shaft includes a single control thread, in other embodiments the control shaft includes multiple (e.g., first and second) control threads. In some embodiments, the control threads are like-threaded. In other embodiments, the control threads have different threads. For example, in some embodiments, a first control thread is opposite-handed from a second control thread. In further embodiments, a first control thread has a different pitch from a second control thread. In yet further embodiments, a first control thread is different handed and has a different pitch from a second control thread.

In some embodiments, one or both of the lower support and the upper support include projections/grooves to provide a gripping surface intended to facilitate gripping adjacent portions of bone. In further embodiments, one or both of the lower support and the upper support include one or more apertures and/or cavities configured to promote bone growth in and around the lower support and the upper support. In some embodiments, the apertures extend from a top, bottom, and/or side surface of the lower support and the upper support and to a central cavity of the implant.

According to any of the embodiments disclosed herein, one or more bone screws may be included and positioned to extend through one or both of the lower support and the upper support and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of the rear face of the implant defined by one or both of the adjustable member and the base member. A head and tool port of the control shaft may further be accessible by way of the rear face of the implant.

In various embodiments, any suitable configuration of the control shaft/control member(s)/control channel(s) may be utilized. In some embodiments, an at least partially spherical control member threadingly engages a threaded control shaft and translates both along the control shaft and within the control channel. In other embodiments, the control member is non-spherical and is received at least partially on or in a control rail or control channel provided by the adjustable member, such that the control member translates along both the control shaft and the control channel or control rail.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of some features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure.

What is claimed is:

1. An expandable implant comprising:
    an upper portion configured to engage a first portion of bone;
    a bottom portion configured to engage a second portion of bone; and
    a control assembly coupled to the upper portion and the bottom portion and configured to control relative movement between the upper portion and the bottom portion, wherein the control assembly includes:

a front portion;
a rear portion defining a rear portion aperture; and
a control shaft coupled to the front portion and extending through the rear portion aperture in the rear portion, where the control shaft includes a first end having a head portion, the head portion configured to engage a rearmost exterior face of the rear portion such that the head portion is at least partially located outside of the rear portion aperture and extends beyond the rearmost exterior face of the rear portion.

2. The implant of claim 1, wherein the rear portion is longitudinally fixed relative to the control shaft, and the front portion is configured to move longitudinally relative to the control portion.

3. The implant of claim 1, wherein the rear portion aperture has a first interior diameter;
wherein the head portion includes an outer ring having a second exterior diameter, larger than the first interior diameter; and
wherein the head portion includes an access ring having a third exterior diameter, smaller than the first interior diameter.

4. The implant of claim 3, wherein the access ring has a retention groove having a fourth exterior diameter smaller than the third exterior diameter, wherein the retention groove is configured to receive a retention member.

5. The implant of claim 4, wherein the head further comprises a recess configured to receive an expansion tool.

6. The implant of claim 5, wherein the recess is positioned within the rear portion aperture as the implant is expanded from the first, collapsed position to the second, expanded position.

7. The implant of claim 4, wherein the rear portion has a retention slot configured to receive the retention member, such that a first portion of the retention member is positioned within the retention groove and a second portion of the retention member is positioned within the retention slot.

8. The implant of claim 1, wherein the upper portion includes a first end having a first cutout and a second end having a first rail offset from a lateral center of the implant, wherein the rear portion includes a second rail received in the first cutout, and the front portion includes a second cutout configured to receive the first rail.

9. A method of installing an expandable implant, comprising:
inserting the implant into a desired location; wherein the implant comprises:
an upper support configured to engage a first portion of bone, wherein the upper support includes a first rail;
a lower support configured to engage a second portion of bone, wherein the second support includes a second rail; and
a control assembly comprising a control member including a head, a rear portion, and a front portion, the rear portion including an aperture extending through the rear portion between a top surface and a bottom surface of the rear portion and configured to receive the control member, the rear portion further comprising a retention hole extending from the top surface to the bottom surface and a retention member received within the retention hole, and wherein the control assembly is configured to control relative movement between the upper support and the lower support; and
manipulating the control member to cause relative sliding movement between the rear portion and both the upper support and the lower support, and the front portion and both the upper support and the lower support, to expand the implant to a desired height;
wherein the front portion includes a first groove configured to slidably engage the first rail and a second groove configured to slidably engage the second rail.

10. The method of claim 9, wherein the front portion is configured to receive a tip of the control member, wherein the control member is configured to control relative movement of the rear portion and the front portion.

11. The method of claim 9, wherein
the aperture has a first interior diameter;
the head includes an outer ring having a second exterior diameter, larger than the first interior diameter; and
the head includes an access ring having a third exterior diameter, smaller than the first interior diameter.

12. The method of claim 11, wherein the access ring has a retention groove having a fourth exterior diameter smaller than the third exterior diameter, wherein the retention groove is configured to receive a retention member.

13. The method of claim 12, wherein the head further comprises a recess configured to receive an expansion tool.

14. The method of claim 13, wherein the recess is positioned within the aperture as the implant is expanded from the first, collapsed position to the second, expanded position.

15. The method of claim 12, wherein the rear portion has a retention slot configured to receive the retention member, such that a portion of the retention member is positioned within the retention groove and a portion of the retention member is positioned within the retention slot.

16. An implant comprising:
an upper support configured to engage a first portion of bone;
a lower support configured to engage a second portion of bone;
a control assembly configured to control relative movement between the upper support and the lower support, the control assembly comprising:
a rear portion configured to engage the upper support at a first end of the upper support, the rear portion including a rear portion aperture extending through the rear portion between a top surface of the rear portion and a bottom surface of the rear portion;
a front portion configured to engage the upper support at a second end of the upper support, the second end being opposite the first end; and
a control member positioned at least partially within the rear portion aperture and adjustably engaging the rear portion and the front portion; and
wherein the upper support and the lower support are identical, and wherein the rear portion has a retention hole extending from the top surface to the bottom surface, and a retention member received within the retention hole.

17. The implant of claim 16, wherein the control member includes a retention slot configured to engage a portion of the retention member.

18. The implant of claim 16, wherein manipulation of the control member causes the front portion to move towards the rear portion and causes the upper support to move away from the lower support.

19. The implant of claim 16, wherein the control member comprises a head, wherein a portion of the head is positioned outside of the rear portion.

20. The implant of claim 16, wherein the retention member extends between the top surface and the bottom surface through the rear portion aperture.

* * * * *